US007820649B2

(12) United States Patent
Letourneau et al.

(10) Patent No.: US 7,820,649 B2
(45) Date of Patent: Oct. 26, 2010

(54) QUINAZOLINONE AND ISOQUINOLINONE ACETAMIDE DERIVATIVES

(75) Inventors: Jeffrey Letourneau, East Windsor, NJ (US); Patrick Jokiel, Princeton, NJ (US); Susan Elizabeth Napier, Newhouse (GB); Koc-Kan Ho, West Windsor, NJ (US); Michael Ohlmeyer, Plainsboro, NJ (US); Duncan Robert McArthur, Newhouse (GB); Fiona Jeremiah, Newhouse (GB); Paul David Ratcliffe, Newhouse (GB); Jurgen Schulz, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/852,762

(22) Filed: Sep. 10, 2007

(65) Prior Publication Data

US 2008/0090802 A1    Apr. 17, 2008

Related U.S. Application Data

(60) Provisional application No. 60/843,718, filed on Sep. 11, 2006.

(51) Int. Cl.
C07D 239/88 (2006.01)
(52) U.S. Cl. .................. 514/218; 540/575; 544/289; 546/141
(58) Field of Classification Search .......... 544/289; 546/141
See application file for complete search history.

(56) References Cited

U.S. PATENT DOCUMENTS

| 4,438,121 | A | 3/1984 | Obitz |
| 6,730,695 | B2 | 5/2004 | Roux |
| 7,202,267 | B2 | 4/2007 | Aulombard et al. |

FOREIGN PATENT DOCUMENTS

| WO | WO 01/55130 | 8/2001 |
| WO | WO 2004/009585 | 1/2004 |
| WO | WO 2006/095014 A1 | 9/2006 |

OTHER PUBLICATIONS

West, Anthony R., Solid State Chemistry and its Applications, Wiley, New York, 1988, pp. 358 and 365.*
Bernardini et al., "In vivo and in vitro Effects of Arginine-Vasopressin Receptor Antagonists on the Hypothalamic-Pituitary-Adrenal Axis in the Rat," *Neuroendocrinology* 60 (1994) 503-508.
De Bold et al., "Arginine Vasopressin Potentiates Adrenocorticotropin Release Induced by Ovine Corticotropin-releasing Factor," *J. Clin. Invest.* 73 (1984) 533-538.
De Goeij et al., "Repeated Stress-Induced Activation of Corticotropin-Releasing Factor Neurons Enhances vasopressin Stores and Colocalization with Corticotrophin-Releasing Factor in the Median Eminence of Rats," *Neuroendocrinology* 53 (1991) 150-159.
Freidinger et al., "Small Molecule Ligands for Oxytocin and Vasopressin Receptors," *Medicinal Research Reviews* 17 (1997) 1-16.
Holsboer et al., "Human Corticotropin-Releasing Hormone in Depression-Correlation with Thyrotropin Secretion following Thyrotropin-Releasing Hormone," *Biol. Psychiatry* 21 (1986) 601-611.
Moss et al., "Catalytic cleavage of active phosphate and ester substrates by iodoso- and iodoxybenzoates," *J. Am. Chem. Soc.* 106 (1984) 2651-2655.
Plotsky et al., "Early, postnatal experience alters hypothalamic corticotropin-releasing factor (CRF) mRNA, median eminence CRF content and stress-induced release in adult rats," *Mol. Brain Res.* 18 (1993) 195-200.
Rivier et al., "Modulation of stress-induced ACTH release by corticotrophin-releasing factor, catecholamines and vasopressin," *Nature* 305 (1983) 325-327.
Scott et al., "Vasopressin and the Regulation of Hypothalamic-Pituitary-Adrenal Axis Function: Implications for the Pathophysiology of Depression," *Life Sciences* 62 (1998) 1985-1988.
Sugimoto et al., "Molecular Cloning and Functional Expression of a cDNA Encoding the Human $V_{1b}$ Vasopressin Recepto," *J. Biol. Chem.* 269 (1994) 27088-27092.
International Search Report and Written Opinion dated Jul. 4, 2006 for related International Application No. PCT/EP2006/060612.
Balawant et al., "Synthesis of Pratorimine," *Journal of Natural Product* 49:445-448 (1986).
Borcherding et al., "Carbocyclic Nucleosides as Inhibitors of Human Tumor Necrosis Factor-α Production: Effects of the Stereoisomers of (3-Hydroxycyclopentyl)adenines," *J. Med. Chem.* 39:2615-2620 (1996).

(Continued)

*Primary Examiner*—James O Wilson
*Assistant Examiner*—Brian McDowell
(74) *Attorney, Agent, or Firm*—Susan L. Hess

(57) ABSTRACT

Disclosed herein are quinazolinone or isoquinolinone derivatives of formula I,

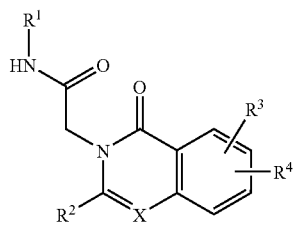

formula I or pharmaceutically acceptable salts or solvates thereof, wherein each of the substituents is given the definition as set forth in the specification and claims. Also disclosed are pharmaceutical compositions comprising quinazolinone or isoquinolinone according to the present invention and its use in therapy.

11 Claims, No Drawings

OTHER PUBLICATIONS

Jordan, V. Craig, "Tamoxifen: a most unlikely pioneering medicine", *Nature Reviews: Drug Discovery* 2(14):205 (2003).

Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo2[,1-b]lquinazoline," *J. Med. Chem.* 31:2136-2145 (1988).

Vippagunta et al., "Crystalline Solids", *Advanced Drug Delivery Reviews*, 48(1):3-26 (May 16, 2001).

International Search Report and Written Opinion dated Oct. 3, 2008 for corresponding International Application No. PCT/US07/78022.

International Search Report and Written Opinion dated Oct. 7, 2008 for related International Application No. PCT/US07/77999.

West, Anthony R., "Chapter 10. Solid Solutions", *Solid State Chemistry and Its Applications*, pp. 358 and 365; John Wiley & Sons, Pub., New York (1988).

* cited by examiner

QUINAZOLINONE AND ISOQUINOLINONE ACETAMIDE DERIVATIVES

The present invention relates to quinazolinone and isoquinolinone derivatives, to pharmaceutical compositions comprising these compounds and to their use in therapy, in particular to their use for the manufacture of a medicament for the treatment or prevention of disorders or diseases influenced by modulation of the activity of the HPA axis.

The hypothalamo-pituitary-adrenal (HPA) axis is the major stress axis in humans and other mammals. A variety of stressors (and multiple other classes of stimuli) cause release of the hormone ACTH (adrenocorticotropic hormone) from the anterior pituitary gland. ACTH enters the systemic circulation and acts on the adrenal cortex to promote synthesis and release of glucocorticoid hormone (the major endogenous glucocorticoid being cortisol in humans and corticosterone in rodents). The glucocorticoids exert a broad spectrum of effects, the main purpose of which is to mobilise energy sources for successful responsiveness and eventual adaptation to the stressor.

Abnormally elevated HPA axis activity in man is associated with the development of a variety of psychiatric disturbances, some of which are stress-related in aetiology. Elevated cortisol levels, which are indicative of HPA axis hyperactivity and loss of normal negative feedback regulatory processes, are a common finding in affective disorders and various other psychiatric disturbances, and are widely utilised as a diagnostic tool (Holsboer et al., *Biol. Psych.*, 1986, 21, 601-611). It is generally considered that dysregulation of the HPA axis is a relection of enhanced vulnerability and poor adaptation to chronic stress and that chronic stress therefore plays a major role in the development of affective illness (Sperry and Carlson, DSM-IV diagnosis to treatment, 2$^{nd}$ Edition, Taylor & Francis, 1996). This central concept is supported by experimental evidence utilising animal models of chronic stress, where abherent HPA function closely resembles that seen in clinical settings (De Goeij et al., *Neuroendocrinology*, 1991, 53, 150-159; Plotsky and Meaney, *Mol. Brain Res.*, 1993, 18, 195-200).

The major secretagogues for ACTH in humans and rats are CRH (corticotropin releasing hormone) and AVP (arginine vasopressin). Within the HPA axis these peptide hormones are synthesised by the parvocellular neurones of the paraventricular nucleus (PVN) of the hypothalamus. The axons of these neurones project to the external zone of the median eminence, from where the hormone products enter the hypophysial portal system to bathe the corticotrope cells that manufacture ACTH. CRH and AVP act synergistically at the corticotrope to regulate ACTH secretion in both rats (Rivier and Vale, *Nature*, 1983, 305, 325-327) and in man (De Bold et al., *J. Clin. Invest.*, 1984, 73, 533-538).

The actions of AVP at the pituitary corticotrope are mediated by the vasopressin $V_3$ (or $V_{1b}$) receptor, which is known and has been cloned (human receptor: Sugimoto et al., *J. Biol. Chem.*, 1994, 269, 27088-27092). A report of clinical studies in depressed patients in which blunted ACTH responses to CRH could be restored by concomitant administration of desmopressin (dDAVP, an AVP agonist with $V_3$ affinity) confirms the involvement of the $V_3$ receptor in depression (Scott and Dinan, *Life Sciences*, 1998, 62, 1985-1988). A study in rodents with non-selective peptide $V_3$ antagonists indicates that the $V_3$ receptor does play a functional role in control of pituitary ACTH release (Bernardini et al., *Neuroendocrinology*, 1994, 60, 503-508). Vasopressin antagonists are thus utilised to modulate and normalise pituitary ACTH release and subsequent HPA axis dysfunction in CNS disorders which are characterised by abnormal HPA axis negative feedback mechanisms.

In addition to the $V_3$ receptor, vasopressin also activates peripheral receptors, i.e., the $V_{1a}$ receptor, predominantly found on liver and vascular tissue and the $V_2$ receptor, predominantly found on kidney tissue. Interaction at these receptors mediate the pressor and antidiuretic actions of AVP.

Whilst there are several non-peptide low-molecular weight antagonists known which are selective for the $V_{1a}$ or the $V_2$ receptor (for a recent review see Freidinger and Pettibone, *Medicinal Research Reviews*, 1997, 17, 1-16), there are only a small number of non-peptide ligands known with selectivity for the $V_3$ receptor (see for example, WO 01/55130 and WO 04/009585). There exists therefore a need for further non-peptide $V_3$ selective antagonists which are both safe and effective.

In a first aspect, the present invention provides a quinazolinone or isoquinolinone derivative of formula I

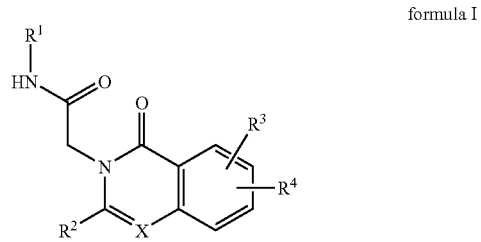

formula I wherein
$R^1$ is $C_{1-6}$alkyl, $C_{3-6}$cycloalkyl, $C_{3-6}$cycloalkyl$C_{1-3}$alkyl, $C_{2-6}$alkenyl, $C_{2-6}$alkynyl, said $C_{1-6}$alkyl, $C_{3-6}$cycloalkyl and $C_{3-6}$cycloalkyl$C_{1-3}$alkyl being optionally substituted with hydroxy, $C_{1-6}$ alkyloxy, cyano or more halogens;
$R^2$ is $C_{6-10}$aryl optionally substituted with one to three substituents selected from halogen, hydroxy, cyano, $C_{1-6}$alkyl, $C_{3-6}$cycloalkyl, $C_{1-6}$alkyloxy and $C_{3-6}$cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens;
or $R^2$ is a 5-10 membered heteroaryl ring system comprising a heteroatom selected from N, O and S and optionally substituted with a substituent selected from methyl, $C_{1-6}$alkyloxy and halogen;
or $R^2$ is $C_{4-7}$cycloalkyl;
$R^3$ is an optional substituent selected from $C_{1-6}$alkyl, $C_{1-6}$alkyloxy and halogen, said $C_{1-6}$alkyl and $C_{1-6}$alkyloxy being optionally substituted with one or more halogens;
$R^4$ is a group located at the 6- or 7-position of the quinazolinone or isoquinolinone ring having the formula II

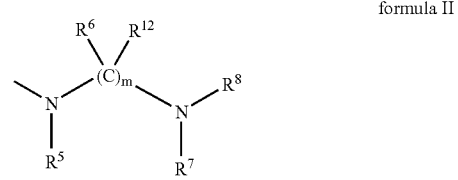

formula II wherein
$R^5$ together with one of $R^6$ forms a 4-8 membered saturated or unsaturated heterocyclic ring optionally comprising a further heteroatomic moiety selected from O, S and $NR^9$, said heterocyclic ring being optionally substituted with one or two substituents selected from methyl, halogen, hydroxy and oxo or $R^5$ together with one of $R^7$ and $R^8$ forms a 6-8 membered heterocyclic ring optionally substituted with one or two substituents selected from methyl, halogen, hydroxy and oxo;

Each $R^6$ is independently H, halogen or $C_{1-4}$alkyl optionally substituted with halogen or $SO_2CH_3$ or one of $R^6$ together with $R^5$ forms a 4-8 membered saturated or unsaturated heterocyclic ring optionally comprising a further heteroatomic moiety selected from O, S and $NR^9$, said heterocyclic ring being optionally substituted with one or two substituents selected from methyl, halogen, hydroxy and oxo;

$R^7$ and $R^8$ are independently H, $C_{1-6}$alkyl, $C_{3-6}$cycloalkyl, $C_{3-6}$cycloalkyl$C_{1-3}$alkyl, cyano$C_{1-3}$alkyl, $C_{6-10}$aryl, $C_{6-10}$aryl$C_{1-3}$alkyl, $C_{1-3}$alkyloxy$C_{1-3}$alkyl or $C_{1-6}$acyl said $C_{1-6}$alkyl, $C_{3-6}$cycloalkyl and $C_{3-6}$cycloalkyl$C_{1-3}$alkyl being optionally substituted with hydroxy, 1 or more halogens or di$C_{1-2}$alkylamino;

or $R^7$ and $R^3$ together with the nitrogen to which they are bonded form a 4-8 membered saturated or unsaturated heterocyclic ring optionally comprising a further heteroatomic moiety selected from O, S and $NR^{10}$, said heterocyclic ring being optionally substituted with one or two substituents selected from $C_{1-6}$alkyl, halogen, hydroxy, $C_{1-6}$alkyloxy, cyano and $COOR^{11}$;

or one of $R^7$ and $R^8$ is Y, $CH_2Y$ or $CH_2CH_2Y$, wherein Y is a 4-6 membered saturated heterocyclic ring comprising a heterocyclic moiety selected from O, $SO_2$ and $NR^{10}$, said ring being optionally substituted with 1-2 substituents selected from methyl or halogen; or one of $R^7$ or $R^3$ together with $R^5$ forms a 6-8 membered heterocyclic ring being optionally substituted with one or two substituents selected from methyl, halogen, hydroxy and oxo or one of $R^7$ and $R^3$ together with $R^{12}$ forms a 4-8 membered saturated or unsaturated heterocyclic ring optionally comprising a further heteroatomic moiety selected from O, S and $NR^{13}$ said heterocyclic ring being optionally substituted with one or two substituents selected from methyl, hydroxy and oxo;

$R^9$ and $R^{10}$ are independently H, $C_{1-6}$alkyl or $C_{1-6}$acyl;

$R^{11}$ is H or $C_{1-6}$alkyl;

Each $R^{12}$ is independently H or $C_{1-4}$alkyl or one of $R^{12}$ together with one of $R^7$ or $R^3$ forms a 4-8 membered saturated or unsaturated heterocyclic ring optionally comprising a further heteroatomic moiety selected from O, S and $NR^{13}$ said heterocyclic ring being optionally substituted with one or two substituents selected from methyl, hydroxy and oxo;

$R^{13}$ is H, $C_{1-6}$alkyl or $C_{1-6}$acyl;

m is 2-3 and

X is N or CH or a pharmaceutically acceptable salt or solvate thereof.

The term $C_{1-6}$alkyl, as used herein, represents a branched or unbranched alkyl group having 1-6 carbon atoms. Examples of such groups are methyl, ethyl, isopropyl, tertiary-butyl, pentyl and hexyl. Similarly the term $C_{1-2}$alkyl, as used herein, represents an alkyl group having 1-2 carbon atoms.

The term $C_{2-6}$alkenyl, as used herein, represents a branched or unbranched alkenyl group having 2-6 carbon atoms and at least one double bond. Examples of such groups are ethenyl and isopropenyl.

The term $C_{2-6}$alkynyl, as used herein, represents a branched or unbranched alkynyl group having 2-6 carbon atoms and at least one triple bond. Examples of such groups are ethynyl and 3-methyl-1-butylyl.

The term $C_{3-6}$cycloalkyl, as used herein, represents a branched or unbranched cyclic alkyl group having 3-6 carbon atoms. Examples of such groups are cyclopropyl, cyclopentyl and 2-methylcyclopentyl. Similarly the term $C_{4-7}$cycloalkyl, as used herein, represents a branched or unbranched cyclic alkyl group having 4-7 carbon atoms.

The term $C_{3-6}$cycloalkyl$C_{1-3}$alkyl, as used herein, represents a $C_{1-3}$alkyl group which is substituted with a $C_{3-6}$cycloalkyl group. Examples of such groups are cyclopropylmethyl and 2-cyclobutylethyl.

The term cyano$C_{1-2}$alkyl, as used herein, represents a $C_{1-2}$ alkyl group which is substituted with a cyano group. Examples of such groups are cyanomethyl and cyanoethyl.

The term di$C_{1-2}$alkylamino, as used herein, represents an amino group which is substituted with two $C_{1-2}$alkyl groups. Examples of such groups are dimethylamine and diethylamine.

The term $C_{1-6}$ alkyloxy, as used herein, represents a branched or unbranched alkyloxy group having 1-6 carbon atoms. Examples of such groups are methoxy, ethoxy, isopropyloxy and tertiary-butyloxy.

The term $C_{3-6}$ cycloalkyloxy, as used herein, represents a branched or unbranched cyclic alkyloxy group having 3-6 carbon atoms. Examples of such groups are cyclopropyloxy, cyclopentyloxy and 2-methylcyclopentyloxy.

The term $C_{1-6}$ acyl, as used herein, represents an acyl group derived from a carboxylic acid having 1-6 carbon atoms. The acyl group can comprise a hydrocarbon which may be branched, unbranched, saturated or unsaturated. Examples of such groups include formyl, acetyl, propionyl, acryloyl and pivaloyl. Also included within the definition of $C_{1-6}$ acyl are groups derived from dicarboxylic acids like groups derived from malonic acid.

The term $C_{6-10}$ aryl, as used herein, represents an aromatic group having 6-10 carbon atoms. Examples of such groups include phenyl and naphthyl.

The term $C_{6-10}$aryl$C_{1-2}$alkyl, as used herein, represents a $C_{1-2}$ alkyl group which is substituted with a $C_{6-10}$ aryl group. Examples of such groups include benzyl and phenethyl.

The term halogen, as used herein, represents a fluorine, chlorine, bromine or iodine.

The term 5-10 membered heteroaryl ring system comprising a heteroatom selected from N, O and S, as used herein, represents a monocyclic or fused bicyclic 5-10 membered heteroaryl ring system comprising a heteroatom selected from N, O and S. Examples of such groups include furanyl, thienyl, pyrrolyl, pyridinyl, indolyl, benzthienyl and quinolinyl.

Examples of 4-8 membered saturated or unsaturated heterocyclic rings formed by $R^5$ and $R^6$ together with the nitrogen to which they are bonded and optionally comprising a further heteroatomic moiety selected from O, S and $NR^7$ wherein $R^5$-$R^7$ have the previously defined meanings include piperidine homopiperidine, morpholine, thiomorpholine, 4-methylpiperazine and tetrahydropyridine.

Examples of 4-6 membered saturated heterocyclic rings comprising a heterocyclic moiety selected from O, $SO_2$, and $NR^{10}$, include tetrahydropyran and piperidine.

The term solvate, as used herein, refers to a complex of variable stoichiometry formed by a solvent and a solute (in this invention, a compound of formula I). Such solvents may not interfere with the biological activity of the solute. Examples of suitable solvents include, water, methanol, ethanol and acetic acid. Preferably the solvent used is a pharmaceutically acceptable solvent, such as water, ethanol and acetic acid.

In one embodiment of the present invention $R^1$ is $C_{1-6}$alkyl, $C_{3-6}$cycloalkyl or $C_{3-6}$ cycloalkyl$C_{1-3}$alkyl. In a further embodiment $R^1$ is $C_{3-4}$alkyl, $C_{3-4}$cycloalkyl or $C_{3-4}$ cycloalkyl$C_{1-3}$alkyl. In a further embodiment $R^1$ is isopropyl, isobutyl, tertiary-butyl, cyclopropylmethyl, cyclobutyl, 2,2,2-trifluoro-1-methylethyl or 2,2,2-trifluoro-1,1-dimethylethyl.

In another embodiment $R^2$ is $C_{6-10}$aryl, optionally substituted with one to three substituents selected from halogen, hydroxy, cyano, $C_{1-6}$alkyl, $C_{3-6}$cycloalkyl, $C_{1-6}$alkyloxy and $C_{3-6}$ cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens. In a further embodiment $R^2$ is a phenyl ring. In a further embodiment $R^2$ is a 3-substituted phenyl ring. In a further embodiment $R^2$ is a 3-substituted phenyl ring substituted with one to three substituents selected from chloro, fluoro, $C_{1-2}$alkyl, trifluoromethyl, $C_{1-3}$alkyloxy, $C_{1-4}$cycloalkyloxy and trifluoromethoxy. In a further embodiment $R^2$ is a substituted phenyl ring selected from 3-chlorophenyl, 3-fluorophenyl, 3-methoxyphenyl, 3-trifluoromethoxyphenyl, 3-chloro-4-fluorophenyl, 4-fluoro-3-methoxyphenyl and 3,5-dimethoxyphenyl.

In another embodiment $R^2$ is a 5-10 membered heteroaryl ring system comprising a heteroatom selected from N, O and S and optionally substituted with a substituent selected from methyl, $C_{1-6}$alkyloxy and halogen. In a further embodiment $R^2$ is a 2-thienyl, 3-thienyl or 6-indolyl optionally substituted with chloro or methyl.

In another embodiment $R^2$ is $C_{4-7}$cycloalkyl

In another embodiment $R^3$ is a substituent selected from chloro, methyl and methoxy. In a further embodiment $R^3$ is a substituent at the 7-position of the quinazolinone.

In a further embodiment $R^3$ is a substituent at the 6-position of the isoquinolinone.

In another embodiment, $R^4$ is the group

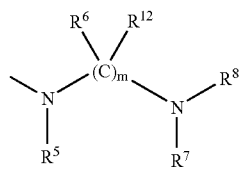

wherein $R^8$-$R^{11}$ have the previously defined meanings. In a further embodiment $R^4$ is a group selected from

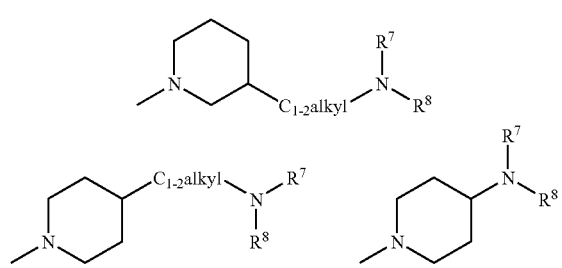

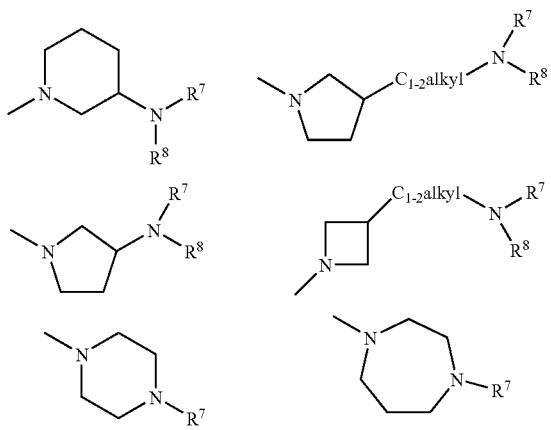

wherein $R^7$ and $R^8$ have the previously defined meanings

In a further embodiment $R^4$ is a group selected from

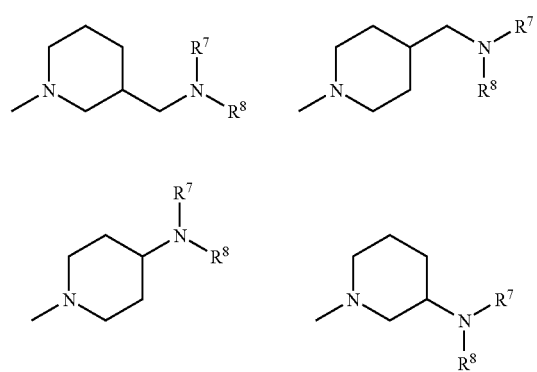

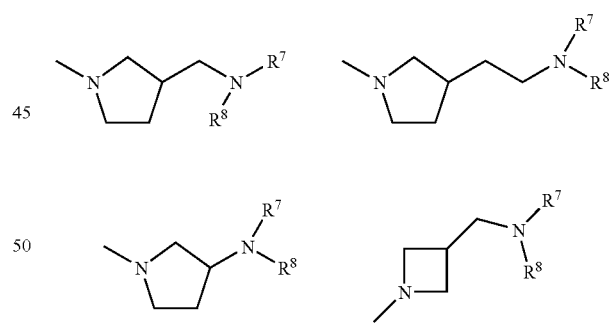

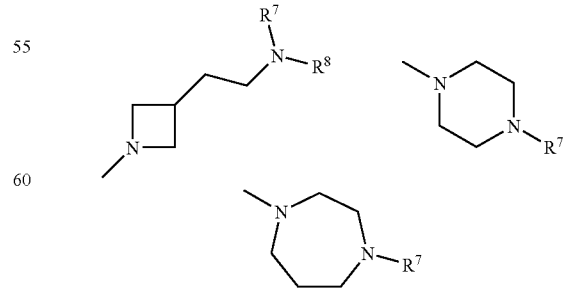

wherein $R^7$ and $R^8$ have the previously defined meanings.

In a further embodiment $R^4$ is a group selected from:

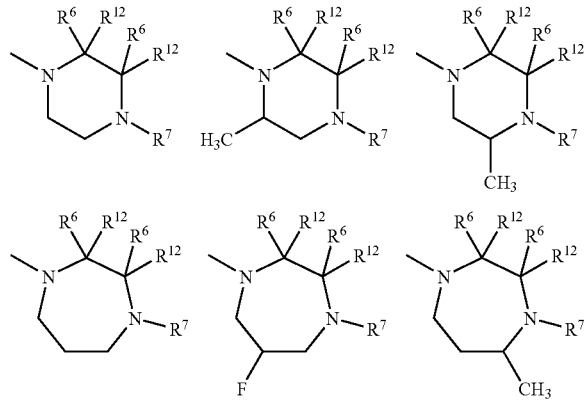

wherein $R^6$, $R^7$ and $R^{12}$ have the previously defined meanings.

In a further embodiment $R^4$ is a group selected from:

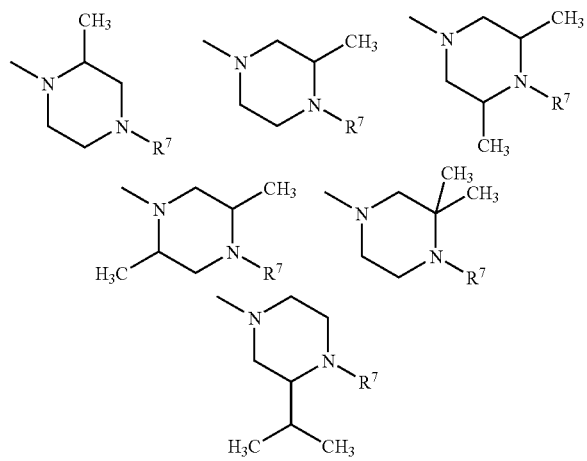

wherein $R^7$ has the previously defined meaning.

In a further embodiment $R^4$ is a group selected from:

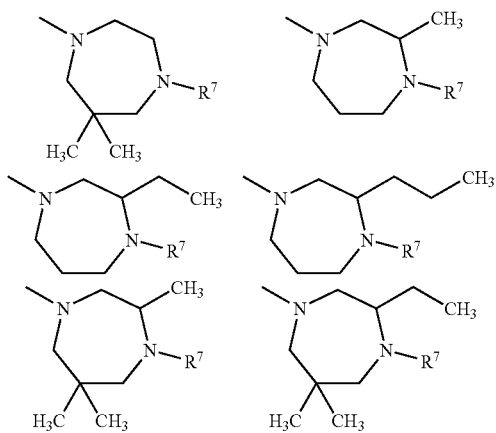

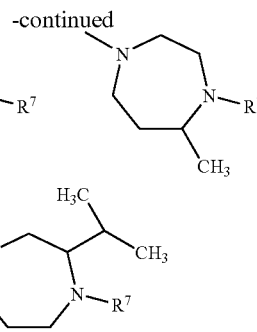

wherein $R^7$ has the previously defined meaning.

In a further embodiment $R^4$ is a group selected from:

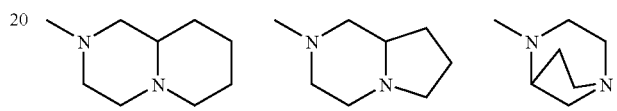

wherein $R^7$ has the previously defined meaning.

In a further embodiment, $R^4$ is a substituent at the 6-position of the quinazolinone. In a further embodiment $R^4$ is a substituent at the 7-position of the isoquinolinone.

In another embodiment, $R^7$ and $R^8$ are independently H, $C_{1-6}$alkyl, $C_{3-6}$cycloalkyl, $C_{3-6}$cycloalkyl$C_{1-3}$alkyl, $C_{6-10}$aryl or $C_{6-10}$aryl$C_{1-3}$alkyl. In a further embodiment $R^7$ and $R^8$ are independently H or $C_{1-4}$alkyl.

In another embodiment, $R^7$ and $R^8$ are independently H, methyl, ethyl, propyl, butyl, isopropyl, hydroxyethyl, methoxyethyl, cyclopropylmethyl, 1-cyclopropylethyl, cyclopentyl or cyclobutyl.

In another embodiment, $R^7$ and $R^8$ are independently selected from: H, methyl and

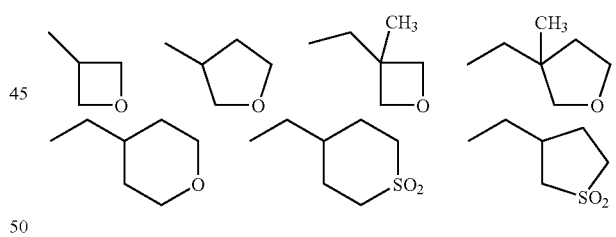

In another embodiment, $R^7$ and $R^8$ together with the nitrogen to which they are bonded form a 4 to 6 membered heterocyclic ring optionally comprising a further heteroatomic moiety selected from O, S or $NR^{10}$, said heterocyclic ring being optionally substituted with a hydroxyl substituent, wherein $R^{10}$ has the previously defined meaning. In a further embodiment $R^7$ and $R^8$ together with the nitrogen to which they are bonded form a heterocyclic ring selected from pyrrolidine, piperidine, 3-hydroxypiperidine and morpholine.

In another embodiment m is 2. In a further embodiment m is 3.

In another embodiment X is N. In a further embodiment X is CH.

In a further embodiment is a quinazolinone selected from:
2-[2-(3-Chlorophenyl)-4-oxo-6-perhydro-1,4-diazepin-1-yl-4H-quinazolin-3-yl]-N-isopropylacetamide;

N-tert-Butyl-2-[2-(3-chlorophenyl)-4-oxo-6-perhydro-1,4-diazepin-1-yl-4H-quinazolin-3-yl]acetamide;
N-tert-Butyl-2-(2-(3-chloro-4-fluorophenyl)-6-(1,4-diazepan-1-yl)-4-oxoquinazolin-3(4H)-yl)acetamide;
2-(2-(3-Chloro-4-fluorophenyl)-6-(1,4-diazepan-1-yl)-4-oxoquinazolin-3(4H)-yl)-N-isopropylacetamide;
2-(2-(3-Chloro-4-fluorophenyl)-6-(3-methyl-1,4-diazepan-1-yl)-4-oxoquinazolin-3(4H)-yl)-N-isopropylacetamide;
2-[2-(3-Chloro-4-fluorophenyl)-6-(3-ethylperhydro-1,4-diazepin-1-yl)-4-oxo-4H-quinazolin-3-yl]-N-isopropylacetamide;
2-[2-(3-Chloro-4-fluorophenyl)-6-(dimethylperhydro-1,4-diazepin-1-yl)-4-oxo-4H-quinazolin-3-yl]-N-isopropylacetamide;
2-[6-(Dimethylperhydro-1,4-diazepin-1-yl)-2-(4-fluoro-3-methoxyphenyl)-4-oxo-4H-quinazolin-3-yl]-N-isopropylacetamide;
2-[2-(3-Chloro-4-fluorophenyl)-6-((S)-3-isopropylperhydro-1,4-diazepin-1-yl)-4-oxo-4H-quinazolin-3-yl]-N-isopropylacetamide;
2-[2-(3-Chlorophenyl)-6-((S)-3-isopropylperhydro-1,4-diazepin-1-yl)-4-oxo-4H-quinazolin-3-yl]-N-isopropylacetamide;
2-[2-(4-Fluoro-3-methoxyphenyl)-6-((S)-3-isopropylperhydro-1,4-diazepin-1-yl)-4-oxo-4H-quinazolin-3-yl]-N-isopropylacetamide;
2-[2-(3-Chloro-4-fluorophenyl)-6-((R)-3-isopropylperhydro-1,4-diazepin-1-yl)-4-oxo-4H-quinazolin-3-yl]-N-isopropylacetamide;
2-[2-(3-Chlorophenyl)-6-((R)-3-isopropylperhydro-1,4-diazepin-1-yl)-4-oxo-4H-quinazolin-3-yl]-N-isopropylacetamide;
2-[2-(4-Fluoro-3-methoxyphenyl)-6-((R)-3-isopropylperhydro-1,4-diazepin-1-yl)-4-oxo-4H-quinazolin-3-yl]-N-isopropylacetamide;
2-[2-(3-Chlorophenyl)-6-(4-methylperhydro-1,4-diazepin-1-yl)-4-oxo-4H-quinazolin-3-yl]-N-isopropylacetamide;
2-[6-(4-Ethylperhydro-1,4-diazepin-1-yl)-2-(3-methoxyphenyl)-4-oxo-4H-quinazolin-3-yl]-N-isopropylacetamide;
2-[2-(3-Chlorophenyl)-4-oxo-6-(4-propylperhydro-1,4-diazepin-1-yl)-4H-quinazolin-3-yl]-N-isopropylacetamide;
N-tert-Butyl-2-[6-(4-ethylperhydro-1,4-diazepin-1-yl)-2-(4-fluoro-3-methoxyphenyl)-4-oxo-4H-quinazolin-3-yl]acetamide;
2-[2-(3-Chlorophenyl)-6-(4-ethylperhydro-1,4-diazepin-1-yl)-4-oxo-4H-quinazolin-3-yl]-N-isopropylacetamide;
2-[6-(4-Ethylperhydro-1,4-diazepin-1-yl)-2-(4-fluoro-3-methoxyphenyl)-4-oxo-4H-quinazolin-3-yl]-N-isopropylacetamide;
2-[2-(4-Fluoro-3-methoxyphenyl)-4-oxo-6-(4-propylperhydro-1,4-diazepin-1-yl)-4H-quinazolin-3-yl]-N-isopropylacetamide;
2-[2-(3-Chloro-4-fluorophenyl)-6-(4-ethylperhydro-1,4-diazepin-1-yl)-4-oxo-4H-quinazolin-3-yl]-N-isopropylacetamide;
N-Isopropyl-2-[6-(4-isopropylperhydro-1,4-diazepin-1-yl)-2-(3-methoxyphenyl)-4-oxo-4H-quinazolin-3-yl]acetamide;
2-[2-(3-Chloro-4-fluorophenyl)-6-(4-isopropylperhydro-1,4-diazepin-1-yl)-4-oxo-4H-quinazolin-3-yl]-N-isopropylacetamide;
2-[2-(3-Chloro-5-trifluoromethylphenyl)-4-oxo-6-perhydro-1,4-diazepin-1-yl-4H-quinazolin-3-yl]-N-isopropylacetamide;

2-[2-(3,5-Dimethoxyphenyl)-6-(4-isopropylperhydro-1,4-diazepin-1-yl)-4-oxo-4H-quinazolin-3-yl]-N-isopropylacetamide;
2-{2-(3-Chloro-4-fluorophenyl)-6-[4-(1-cyclopropylethyl)perhydro-1,4-diazepin-1-yl]-4-oxo-4H-quinazolin-3-yl}-N-isopropylacetamide;
2-{2-(4-Fluoro-3-methoxyphenyl)-6-[4-(2-hydroxyethyl)perhydro-1,4-diazepin-1-yl]-4-oxo-4H-quinazolin-3-yl}-N-isopropylacetamide;
2-{2-(3-Chloro-4-fluorophenyl)-6-[4-(2-hydroxyethyl)perhydro-1,4-diazepin-1-yl]-4-oxo-4H-quinazolin-3-yl}-N-isopropylacetamide;
2-[2-(3-Chloro-4-fluorophenyl)-6-(1,4-diazabicyclo[3.2.2]non-4-yl)-4-oxo-4H-quinazolin-3-yl]-N-isopropylacetamide;
2-[2-(4-Fluoro-3-methoxyphenyl)-6-(4-isopropylpiperazin-1-yl)-4-oxo-4H-quinazolin-3-yl]-N-isopropylacetamide;
2-[2-(3-Chloro-4-fluorophenyl)-6-(4-isopropylpiperazin-1-yl)-4-oxo-4H-quinazolin-3-yl]-N-isopropylacetamide;
2-[2-(3-Chloro-4-fluorophenyl)-6-((S)-3-isopropylpiperazin-1-yl)-4-oxo-4H-quinazolin-3-yl]-N-isopropylacetamide;
2-[2-(3-Chloro-4-fluorophenyl)-6-((R)-3-isopropylpiperazin-1-yl)-4-oxo-4H-quinazolin-3-yl]-N-isopropylacetamide;
2-[6-(1,4-Diazabicyclo[3.2.2]non-4-yl)-2-(3,5-dimethoxyphenyl)-4-oxo-4H-quinazolin-3-yl]-N-isopropylacetamide;
2-[2-(3-Chlorophenyl)-6-(4-isopropylperhydro-1,4-diazepin-1-yl)-4-oxo-4H-quinazolin-3-yl]-N-(2,2,2-trifluoro-1,1-dimethylethyl)acetamide;
N-Isopropyl-2-(6-(4-isopropyl-1,4-diazepan-1-yl)-2-(3-methoxyphenyl)-4-oxoquinazolin-3(4H)-yl)acetamide;
2-(2-(3-Chlorophenyl)-6-(4-cyclopropylmethyl-1,4-diazepan-1-yl)-4-oxoquinazolin-3(4H)-yl)-N-isopropylacetamide
and
N-tert-Butyl-2-(2-(3-chlorophenyl)-6-(4-isopropyl-1,4-diazepan-1-yl)-4-oxoquinazolin-3(4H)-yl)acetamide or a pharmaceutically acceptable salt or solvate thereof.

The quinazolinone and isoquinolinone derivatives of the present invention are prepared by methods well known in the art of organic chemistry. See, for example, J. March, *'Advanced Organic Chemistry'* 4<sup>th</sup> Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wuts, *'Protective Groups in Organic Synthesis'* 2<sup>nd</sup> Edition, John Wiley and Sons, 1991. The protective groups are optionally removed at a convenient subsequent stage using methods well known in the art.

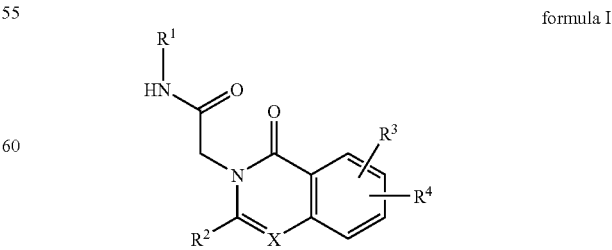

formula I

Quinazolinone and isoquinolinone derivatives of formula I wherein $R^4$ is the group

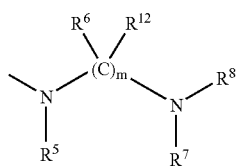

and X is N (shown as 8 below) can be prepared by the general three stage synthetic sequence shown in Scheme 1. Firstly an anthranilic acid of formula 2 wherein $R^4$ is OH or a suitably reactive group such as halogen (e.g. bromo or iodo) etc., is reacted with a glycine amide of formula 3 in the presence of a suitable amide bond coupling reagent to give the coupled product 4. One example of such a coupling reagent would be EDCI. The coupling reagent is added either alone or in the presence of an additive such as HOBt and in a suitable inert solvent such as dichloromethane or DMF. The necessary anthranilic acids 2 and glycine amides 3 are either commercially available or they can readily be prepared by procedures well known in the art. The intermediate quinazolinones of general formula 6 can be made by condensation of the imidate salt 5 in a suitable solvent such as ethanol and at elevated temperatures such as at reflux. Intermediates 6 wherein $R^4$ is a reactive group such as triflate can be readily prepared from the corresponding intermediate 6 wherein $R^4$ is OH using procedures well known in the art, for example the triflate can be prepared by treatment of alcohols 6 with trifluoromethanesulfonic anhydride and pyridine. The intermediate quinazolinones 6 wherein $R^4$ is a suitably reactive group such as halogen (e.g. bromo or iodo), triflate, etc., can then be functionalised with diamines of formula 7 in the presence of a suitable catalyst system, such as $Pd_2(dba)_3$ and BINAP, under conditions well known in the art to provide the desired product 8. Diamines of formula 7 are either commercially available or they can readily be prepared by procedures well known in the art.

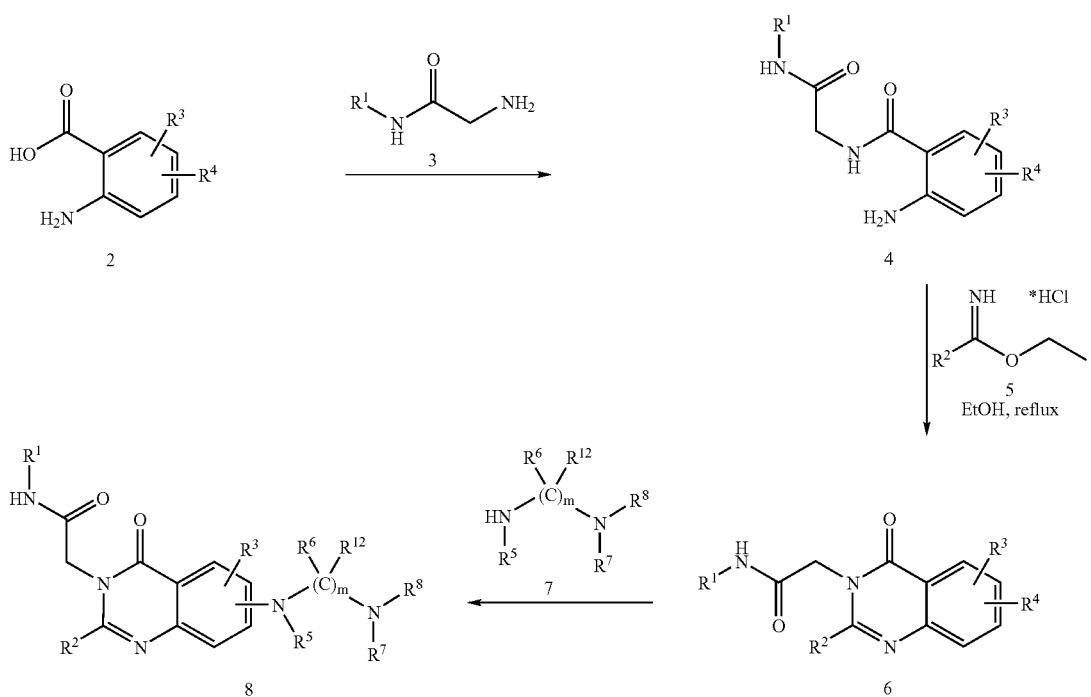

Scheme 1

Alternatively, the quinazolinone intermediates 6 can be formed by condensation of intermediate 4 with a suitable aldehyde, $R^2CHO$, followed by subsequent oxidation of the resultant dihydroquinazolinone intermediate 9 with a suitable oxidant such as $MnO_2$, DDQ, or $CuCl_2$ (Scheme 2). Aldehydes $R^2CHO$ are either commercially available or they can readily be prepared by procedures well known in the art.

Scheme 2

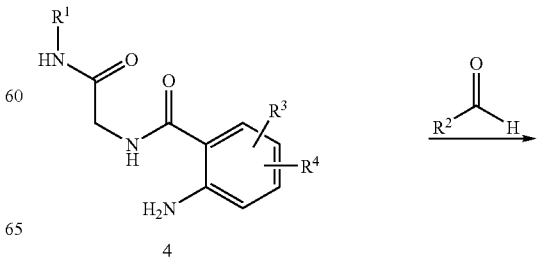

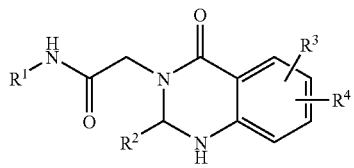

9

↓ [O]

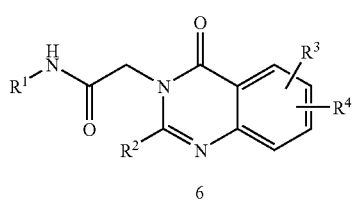

6

$R^4$ = Br, I, OH etc.

The amide intermediate 4 can alternatively be prepared by reaction of an isatoic anhydride of general formula 10 with a glycine amide of formula 3 in a polar aprotic solvent such as acetonitrile. The isatoic anhydrides 10 are either commercially available or can readily be prepared by reaction of a suitable anthranilic acid of formula 2 with a carbonylating reagent such as phosgene or triphosgene (Scheme 3).

Scheme 3

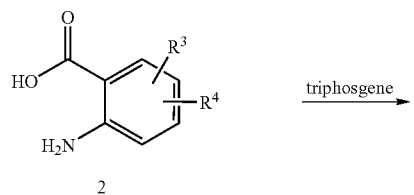

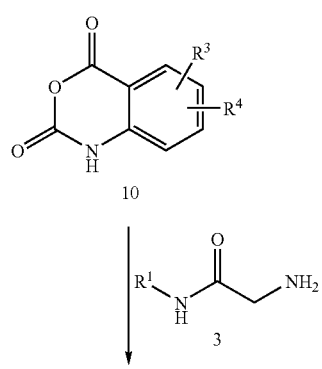

4

Compounds of formula I wherein $R^4$ is the group and X is N can also be prepared in four stages from the required fluoro-2-nitrobenzoic acid 11 as shown in Scheme 4. The fluoro-2-nitrobenzoic acid derivatives are either commercially available or can be prepared using procedures well known in the art of organic chemistry. The acid 11 can be coupled with a glycine amide of formula 3 using analogous procedures to those indicated previously (see Scheme 1) to yield the amide 12. This in turn can then treated with amine 7 in an inert polar, aprotic solvent such as DMF, DMSO or DMP at elevated temperatures and in the presence of a suitable base (for example, potassium or cesium carbonate) to afford the adduct 13. Amines 7 are either commercially available or they can readily be prepared by procedures well known in the art. The nitro group is then reduced to give the aniline 14 using methods well known in the art, for example, reduction under a hydrogen atmosphere and in the presence of a suitable catalyst such as palladium on carbon. Finally, the desired quinazolinones 8 can be prepared upon reaction of 14 with an imidate* HCl salt of formula 5 (as previously described—Scheme 1) or upon reaction of 14 with an aldehyde $R^2$CHO followed by oxidation (as previously described—Scheme 2).

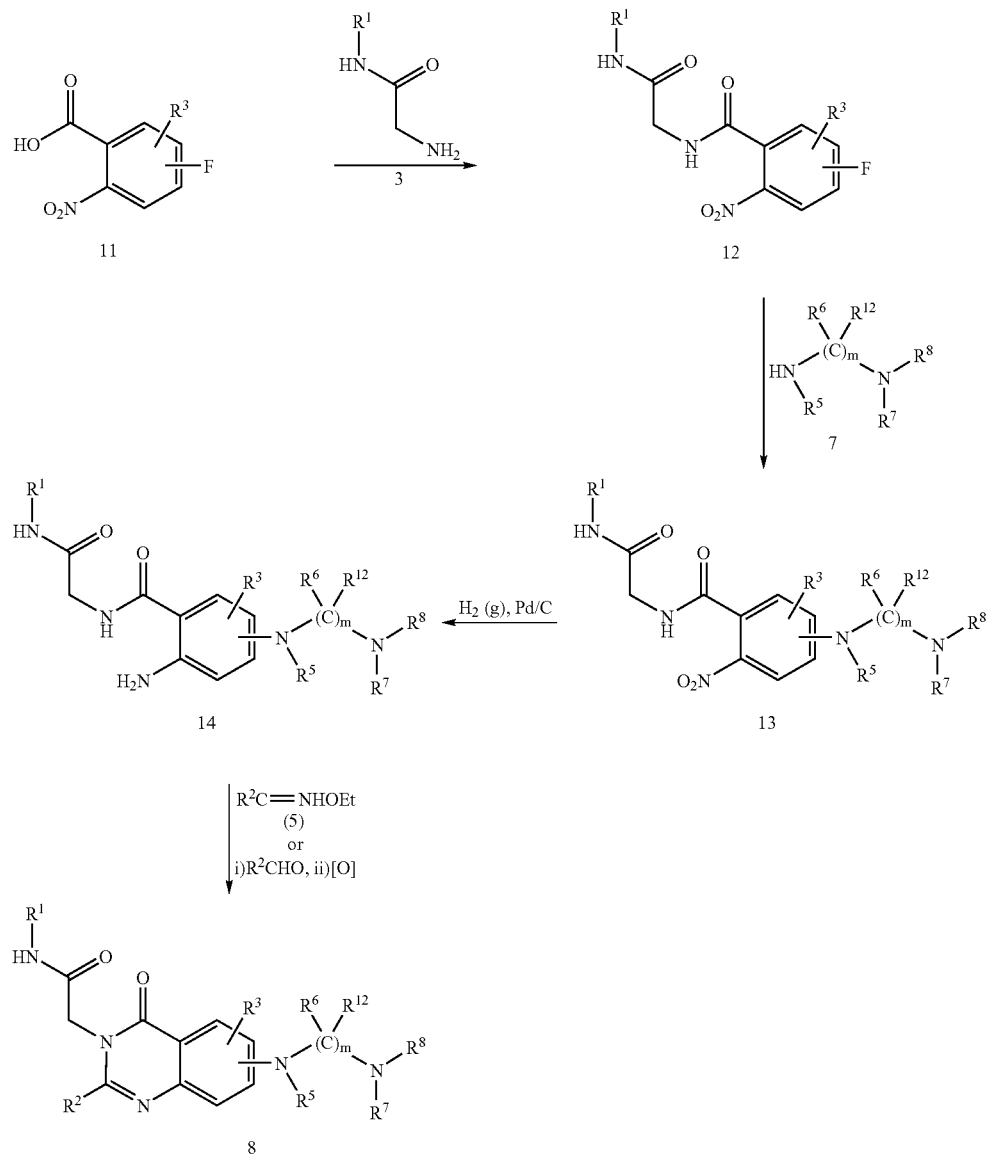

Scheme 4

Compounds of formula I wherein $R^4$ is the group

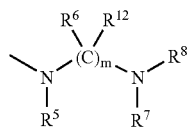

and X is N can also be prepared in 6 stages from the required fluoro-2-nitrobenzoic acid 15 as shown in Scheme 5. The fluoro-2-nitrobenzoic acid derivatives 11 are either commercially available or can be prepared using procedures well known in the art of organic chemistry. The acid 11 can be coupled with suitably protected glycine of formula 16, for example glycine tert-butyl ester or glycine methyl ester, using analogous procedures to those indicated previously (see Scheme 1) to yield the amide 15. Suitably protected glycine of formula 16 is either commercially available or can be prepared using procedures well known in the art of organic chemistry. Amide 15 can in turn be treated with amine 7 in an inert polar, aprotic solvent such as DMF, DMSO or DMP at elevated temperatures and in the presence of a suitable base (for example, potassium or cesium carbonate) to afford the adduct 17. Amines 7 are either commercially available or they can readily be prepared by procedures well known in the art of organic chemistry. The nitro group can then reduced to give the aniline 18 using methods well known in the art, for example, reduction under a hydrogen atmosphere and in the presence of a suitable catalyst such as palladium on carbon. Quinazolinones 19 are prepared upon reaction of 18 with an imidate* HCl salt of formula 5 (as previously described—Scheme 1) or upon reaction of 14 with an aldehyde $R^2$CHO followed by oxidation (as previously described—Scheme 2).

Removal of the carboxylic acid protecting group can be readily achieved using procedures well known in the art of organic chemistry, for example tert-butyl ester can be removed under acidic conditions for example trifluoroacetic acid in an aprotic solvent such as DMF or DCM, to give the carboxylic acids 20. Finally, the desired quinazolinones 8 can be prepared by reaction carboxylic acid 20 with amine 21 using procedures well known in the art, for example a suitable amide coupling reagent. One example of such a coupling reagent would be EDCI. The coupling agent is added either alone or in the presence of an additive such as HOBt and in a suitable inert solvent such as DMF or DCM.

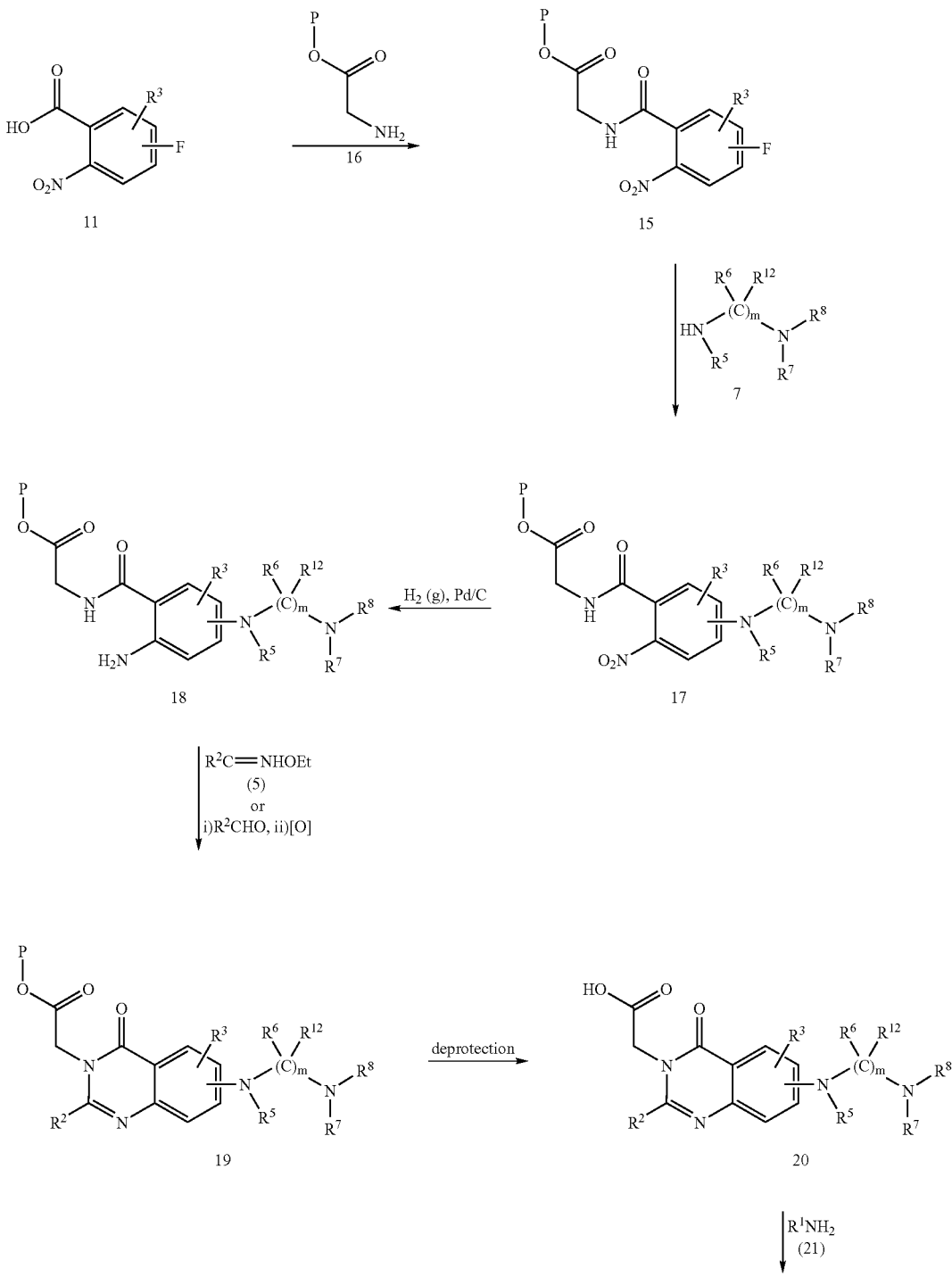

Scheme 5

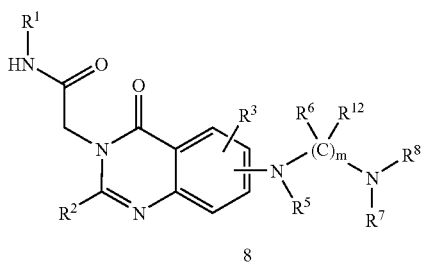

Compounds of formula I wherein $R^4$ is the group

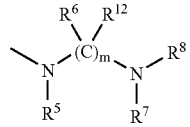

and X is CH (shown as 29 below) can be prepared by the general six stage synthetic sequence shown in Scheme 6. Firstly a suitably functionalised 2-halobenzoic acid ester of formula 22, can be reacted with a suitably functionalised styrene of formula 23 in the presence of a suitable Pd(II) catalyst (for example palladium diacetate), a triarylphosphine ligand (for example tri(o-tolyl)phosphine) and a tertiary amine base (for example triethylamine) in a polar aprotic solvent (for example acetonitrile) to give the coupled product 24. P represents a suitable protecting group, for example methyl. The 2-halobenzoic acids 22 and styrenes 23 are either commercially available or they can readily be prepared by procedures well known in the art. The carboxylic acid ester 24 can then be hydrolysed to the carboxylic acid 25 using either acid or base in a suitable solvent such as ethanol. The carboxylic acid intermediate 25 can subsequently be cyclised to the isocoumarin 26 using a palladium(II) catalyst, for example, bis(acetonitrile)dichloropalladium(II) and an oxidant, for example, p-benzoquinone, in an inert solvent, for example, tetrahydrofuran. The isocoumarin 26 thus obtained can be heated together with a glycine amide 3 to provide the isoquinolinone which can subsequently be deprotected to give isoquinolinone 27. The free alcohol 27 thus obtained can be converted to the corresponding triflate using procedures well known in the art, for example by treatment of alcohol 27 with trifluoromethanesulfonic anhydride and pyridine. Triflate 28 can be reacted with diamines of formula 7 in the presence of a suitable catalyst system, such as $Pd_2(dba)_3$ and BINAP, under conditions well known in the art to afford desired isoquinolones 29 (Scheme 6).

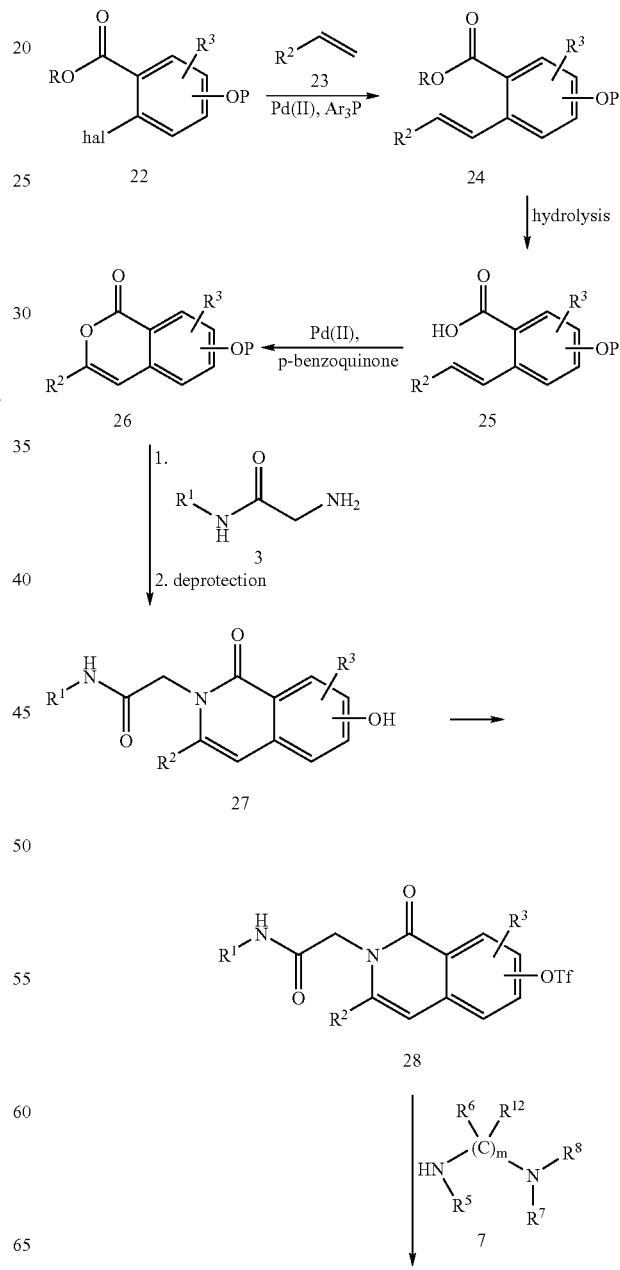

-continued

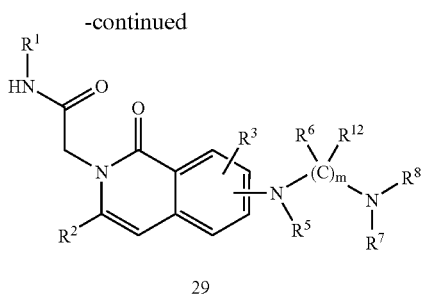

29

Compounds of formula I wherein $R^4$ is the group

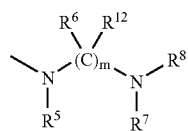

and X is CH (shown as 29 below) can alternatively be prepared by the general five stage synthetic sequence shown in Scheme 7. Firstly a 4-halobenzaldehyde of formula 30, halo can be for example fluoro, can be reacted with amine 7 in an inert polar, aprotic solvent such as DMF, DMSO or DMP at elevated temperatures and in the presence of a suitable base (for example, potassium or cesium carbonate) to afford the aldehyde 31. Aldehyde 31 can be reacted with a suitably functionalised carboxylic acid (32), carboxylic acid ester (33) or nitrile (34) to afford carboxylic acid 35. Carboxylic acid 35 can be formed directly when using a suitably functionalised carboxylic acid 32 or following subsequent hydrolysis of the carboxylic acid ester or nitrile when using carboxylic acid ester 33 or nitrile 34 respectively. Hydrolysis can be achieved using procedures well known in the art of organic chemistry. Subsequent treatment of adduct 35 with, for example, DPPA at elevated temperatures can afford isoquinolone 36 via a Curtius reaction. Alkylation of isoquinolone 36 with a suitably protected bromoacetic acid derivative 37 (P represents a suitable protecting group, for example methyl) can afford ester 38. Hydrolysis of ester 38 using procedures well known in the art of organic chemistry and subsequent reaction with amine 21 using procedures well known in the art (as previously described—Scheme 7) can afford the desired isoquinolones 29.

Scheme 7

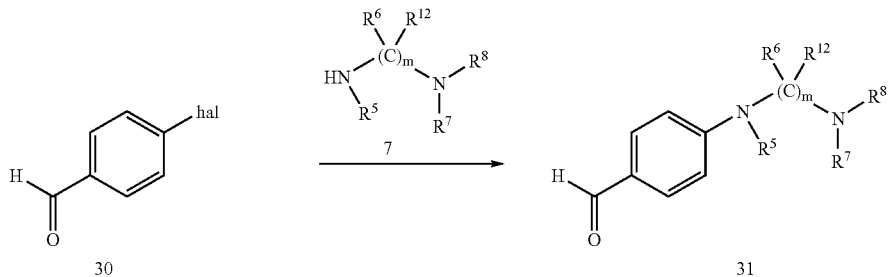

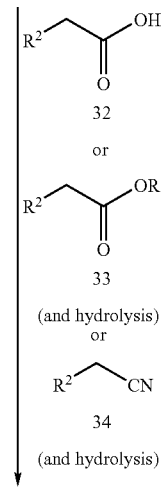

-continued

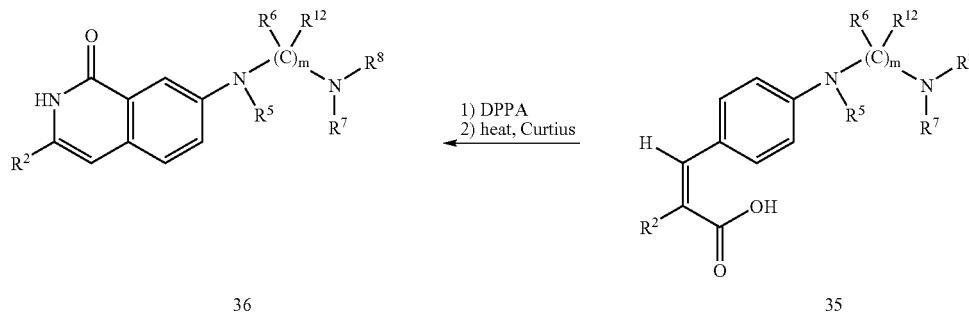

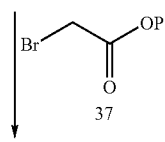

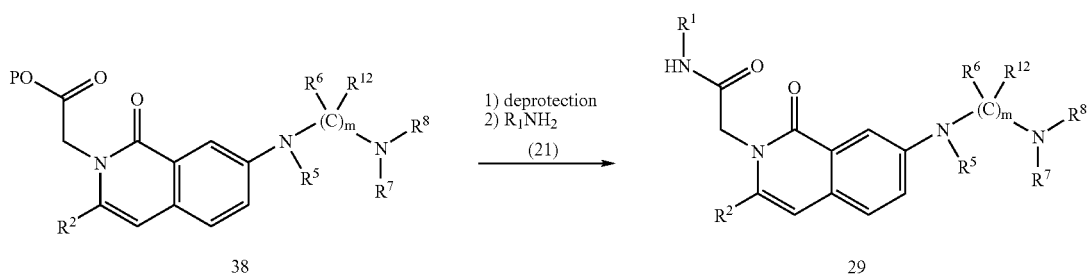

Compounds of formula I wherein $R^4$ is the group

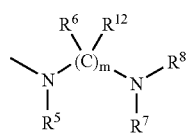

and X is CH (shown as 29 below) can alternatively be prepared by the general five stage synthetic sequence shown in Scheme 8. A 3-halo-6-methylbenzoic acid of formula 39, halo can be for example fluoro, can be reacted with diamines of formula 7 in an inert polar, aprotic solvent such as DMF, DMSO or DMP at elevated temperatures and in the presence of a base such as potassium carbonate can afford carboxylic acid 40. Carboxylic acid 40 can be converted to amide 41 by reaction with methylamine using procedures well known in the art of organic chemistry, for example converting to the acid chloride with thionyl chloride or oxalyl chloride and subsequent reaction with methylamine. Amide 41 can be treated with a suitable base, for example LDA or BuLi, and subsequently reacted with an appropriately substituted nitrile 42 in a suitable solvent to provide isoquinolone 36. Isoquinolones 38 can be prepared upon reaction of 36 with a suitably protected bromoacetic acid derivative 37 in an inert polar, aprotic solvent such as DMF and in the presence of a suitable base such as potassium carbonate. P represents a protecting group for example methyl. The carboxylic acid ester can then be hydrolysed to the carboxylic acid using either acid or base in a suitable solvent and subsequently reacted with amine 21 (as previously described—Scheme 7) to afford isoquinolones 29.

Scheme 8

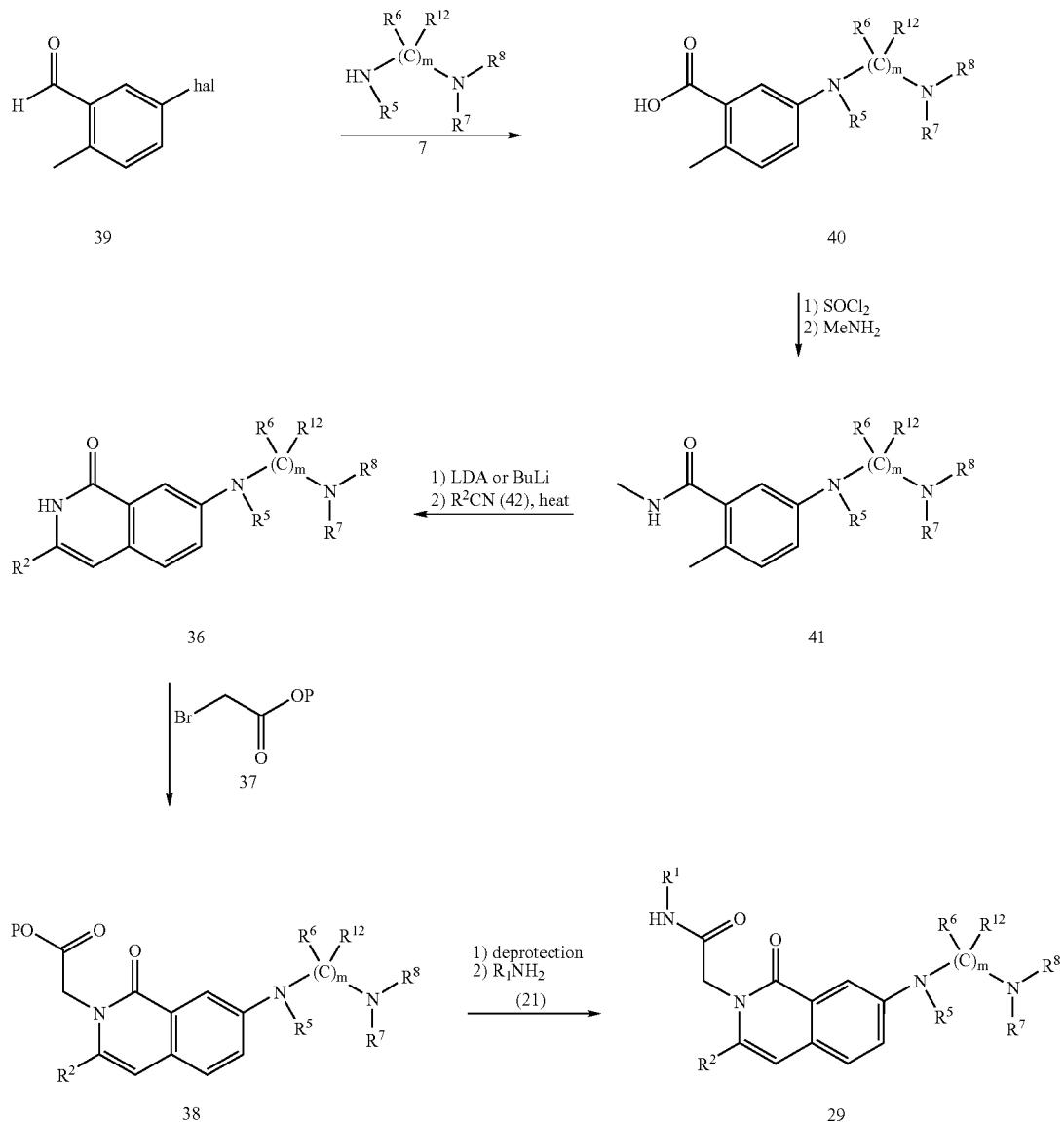

Compounds of formula I wherein R⁴ is the group

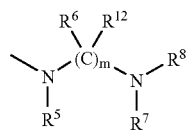

and X is CH (shown as 29 below) can alternatively be prepared by the general five stage synthetic sequence shown in Scheme 9. A 3-halo-6-methylbenzoic acid of formula 39, where halo can for example chloro or bromo, can be reacted with methylamine using procedures well known in the art of organic chemistry to provide amide 43. For example acid 39 can be converted to the acid chloride by reaction with, for example, thionyl chloride or oxalyl chloride at elevated temperature. The acid chloride can then be treated with methylamine. Amide 43 can be reacted with a suitable base, for example LDA or BuLi, in a suitable solvent such as THF and subsequently treated with an appropriately substituted nitrile of formula 42 to provide isoquinolone 44. Isoquinolone 45 can be prepared by alkylation of isoquinolone 44 with a bromoacetic acid ester derivative 37 in a polar aprotic solvent such as DMF and in the presence of a suitable base such as potassium carbonate. P is a protecting group for example methyl. Deprotection using procedures well known in the art of organic chemistry followed by reaction with amine 21 can provide isoquinolones of formula 46. Isoquinolones of formula 29 can be prepared by reacting isoquinolones 46 with diamines of formula 7 at elevated temperatures in a suitable solvent and in the presence of a suitable catalyst system, such as [1,3-bis(2,6-diisopropylphenyl)imidazol-2-ylidene](3-chloropyridyl)palladium(II) dichloride.

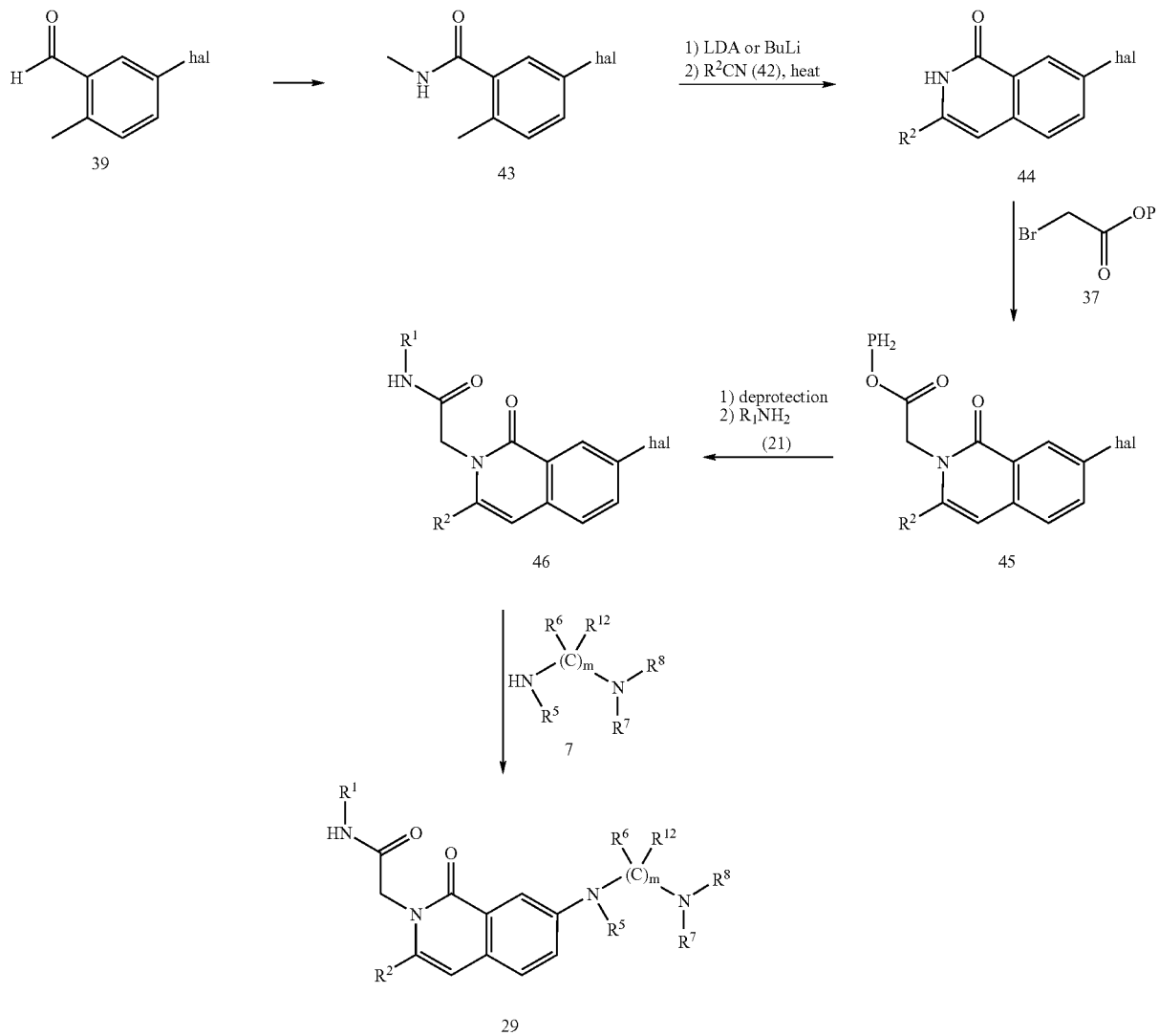

Scheme 9

It will be readily appreciated by one skilled in the art that the quinazolinones and isoquinolinones of general formula I can be prepared using the general procedures and/or reaction sequences described above in any suitable order. For example, whereas the processes detailed above describe introduction of the $R^4$ groups later in the syntheses utilizing preformed quinazolinone and isoquinolinone intermediates, it will be recognized that, in some cases, the $R^4$ groups can be introduced before the formation of the quinazolinone and isoquinolinone ring system.

The present invention also includes within its scope all stereoisomeric forms of quinazolinone and isoquinolinone derivatives resulting, for example, because of configurational or geometrical isomerism. Such stereoisomeric forms are enantiomers, diastereoisomers, cis and trans isomers etc. For example, in the case where $R^1$ is 2-methylcyclopropylamine the compound exists as a pair of enantiomers. In the case where $R^4$ comprises an alkene fragment, both (Z) and (E) stereoisomeric forms of the compound are possible. In the case of the individual enantiomers of quinazolinone and iso- quinolinone derivatives of formula I or salts or solvates thereof, the present invention includes the aforementioned stereoisomers substantially free, i.e., associated with less than 5%, preferably less than 2% and in particular less than 1% of the other enantiomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The present invention also includes within its scope all isotopically labelled forms of the compounds of the invention. For example, compounds isotopically labelled with $^2H$, $^3H$, $^{11}C$, $^{13}C$, $^{14}C$, $^{131}I$, $^{125}I$, $^{123}I$ and $^{18}F$. The labelled compounds are useful as diagnostic tools, radio tracers, or monitoring agents in various diagnostic methods and for in vivo receptor imaging.

The quinazolinone and isoquinolinone derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The quinazolinone and isoquinolinone derivatives of the present invention also exist as amorphous forms. Multiple crystalline forms are also possible. All these physical forms are included within the scope of the present invention.

In a further aspect, the quinazolinone and isoquinolinone derivatives of the present invention and their pharmaceutically acceptable salts and solvates are useful in therapy. As such the quinazolinone and isoquinolinone derivatives of the present invention are useful for the manufacture of a medicament for the treatment or prevention of diseases influenced by modulation of the activity of the HPA axis. In particular the quinazolinone and isoquinolinone derivatives are useful for the manufacture of a medicament for the treatment of schizophrenia, anxiety, hot flushes, addiction, anorexia nervosa, stress-related disorders and Alzheimer's dementia.

In a further aspect, the quinazolinone and isoquinolinone derivatives of the present invention are useful for the manufacture of a medicament for the treatment or prevention of depression. Depression states in the treatment of which the compounds of the present invention and their pharmaceutically acceptable salts and solvates are particularly useful are those classified as mood disorders in the *Diagnostic and Statistical Manual of Mental Disorders, Fourth Edition—Text Revised*, American Psychiatric Association, Washington D.C. (2000), including mood episodes, depressive disorders, bipolar disorders and other mood disorders.

The present invention further includes a method for the treatment of a mammal, including a human, suffering from or liable to suffer from depression or any of the aforementioned disorders, which comprises administering an effective amount of a quinazolinone or isoquinolinone derivative of the present invention or a pharmaceutically acceptable salt or solvate thereof.

The amount of a quinazolinone or isoquinolinone derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical formulation. The present invention therefore also provides a pharmaceutical composition comprising a quinazolinone and isoquinolinone derivative according to the present invention in admixture with one or more pharmaceutically acceptable excipients, such as the ones described in Gennaro et. al., Remington: *The Science and Practice of Pharmacy*, 20$^{th}$ Edition, Lippincott, Williams and Wilkins, 2000; see especially part 5: pharmaceutical manufacturing. The term 'acceptable' means being compatible with the other ingredients of the composition and not deleterious to the recipients thereof. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a quinazolinone and isoquinolinone derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The following Examples further illustrate the compounds of the present invention and methods for their synthesis. In the following section, there is described the synthesis of precursors and common intermediates for compounds of the present invention Procedure I INTERMEDIATE I.1:
2-Amino-N-isopropylacetamide

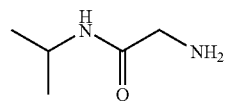

a) (Isopropylcarbamoylmethyl)carbamic acid benzyl ester

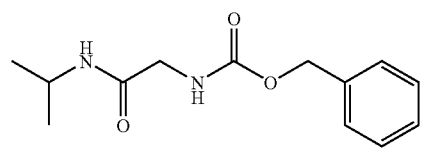

To a solution of N-Cbz-glycine (20.9 g, 100 mmol) in THF (400 mL) at 0° C. was added N-methylmorpholine (NMM)

(12.1 mL, 110 mmol) and i-butylchloroformate (13 mL, 100 mmol). The resultant mixture was stirred at 0° C. for 2 min and then i-propylamine (9.4 mL, 110 mmol) was added. The reaction mixture was warmed to room temperature and stirred at this temperature for 16 h. The mixture was filtered through a pad of CELITE™ and concentrated in vacuo. The crude residue was dissolved in ethyl acetate (500 mL) and washed with 1N HCl (aq.) (1×100 mL), sat. NaHCO₃ (aq.) (1×100 mL) and brine (1×100 mL). The organic layer was dried (MgSO₄), filtered and concentrated in vacuo to afford (isopropylcarbamoylmethyl)carbamic acid benzyl ester as a white solid (24.5 g, 98 mmol, 98%) which was used without further purification.

Data: $^1$H NMR (300 MHz, CDCl₃): δ 7.37 (m, 5H), 5.78 (br s, 1H), 5.41 (br s, 1H), 5.15 (s, 2H), 4.07 (septet, 1H), 3.82 (d, 2H), 1.15 (d, 6H) ppm.

b) 2-Amino-N-isoprolylacetamide

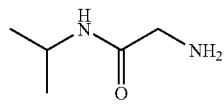

10% Pd/C (425 mg) was added to a solution of (isopropylcarbamoylmethyl)carbamic acid benzyl ester (10 g, 40 mmol) in ethanol (200 mL) and shaken in a Parr shaker under a hydrogen atmosphere (50 p.s.i.) for 16 h. The reaction mixture was filtered through a pad of CELITE™ and the solvent removed in vacuo. This afforded 2-amino-N-isopropylacetamide (INTERMEDIATE I.1) as a clear, colourless oil (5.1 g, 40 mmol, 100%).

Data for 2-amino-N-isopropylacetamide (INTERMEDIATE I.1): $^1$H NMR (300 MHz, CDCl₃): δ 7.05 (br s, 1H), 4.11 (septet, 1H), 3.33 (s, 2H), 1.48 (br s, 2H, amine N$\underline{H}_2$), 1.15 (d, 6H) ppm.

Similarly prepared were:

INTERMEDIATE I.2: 2-Amino-N-tert-butylacetamide

Procedure II

INTERMEDIATE II.1: Ethyl 3-chlorobenzimidate hydrochloride

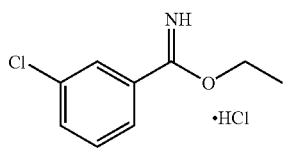

To a solution of 3-chlorobenzonitrile (50 g, 363 mmol) in anhydrous ethanol (500 mL), cooled to 0° C. in an ice bath, was bubbled HCl (g) through a gas dispersion tube for approximately 20 minutes until the solution was saturated. The resulting reaction mixture was stirred at room temperature for 16 h. Volatiles were removed in vacuo and the residue was triturated with anhydrous ether (~200 mL). The white solid was collected by filtration and dried in vacuo overnight to afford ethyl 3-chlorobenzimidate hydrochloride (INTERMEDIATE II.1) (80 g, 363 mmol, 100%) which was used directly without further purification.

Data for ethyl 3-chlorobenzimidate hydrochloride (INTERMEDIATE II.1): $^1$H NMR (300 MHz, DMSO): δ 12.0-11.8 (br s, 1H), 8.22-8.17 (t, 1H), 8.10-8.04 (dt, 1H), 7.90-7.85 (dt, 1H), 7.71-7.64 (t, 1H), 4.66-4.50 (q, 2H), 1.55-1.40 (t, 3H) ppm.

Similarly prepared were:

INTERMEDIATE II.2: Ethyl 3-methoxybenzimidate hydrochloride

INTERMEDIATE II.3: Ethyl 4-fluoro-3-methoxybenzimidate hydrochloride

INTERMEDIATE II.4: Ethyl 3-chloro-4-fluorobenzimidate hydrochloride

Procedure III

INTERMEDIATE III.1:
1-Azetidin-3-ylmethylpiperidine

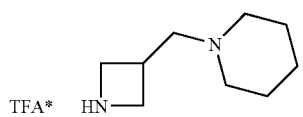

a)
3-Methanesulfonyloxymethylazetidine-1-carboxylic acid tert-butyl ester

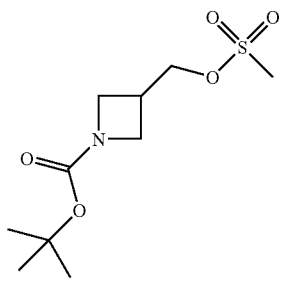

To a solution of 3-hydroxymethylazetidine-1-carboxylic acid tert-butyl ester (for preparation see: Askew, B., et al., US 20033225106) (0.3 g, 1.60 mmol) in DCM (3 mL) was added Et₃N (1 mL, 7.17 mmol), followed by methanesulfonyl chloride (0.5 mL, 6.46 mmol) and the reaction mixture stirred at room temperature for 1 h. The reaction mixture was concentrated in vacuo, the residue dissolved in DCM and the organic phase washed with saturated sodium bicarbonate (aq.). The organic layer was dried (MgSO₄), and concentrated in vacuo to give 3-methanesulfonyloxymethylazetidine-1-carboxylic acid tert-butyl ester (0.36 g, 1.40 mmol, 85%) as an oil which was used in the next step without further purification.

Data for 3-methanesulfonyloxymethylazetidine-1-carboxylic acid tert-butyl ester: $^1$H NMR (300 MHz, CDCl$_3$): δ 4.36 (d, 2H), 4.05 (app t, 2H), 3.72 (dd, 2H), 3.05 (s, 3H), 2.92 (m, 1H), 1.42 (s, 9H) ppm.

b) 3-Piperidin-1-ylmethylazetidine-1-carboxylic acid tert-butyl ester

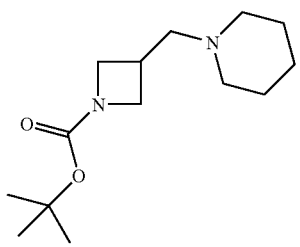

To a suspension of 3-methanesulfonyloxymethylazetidine-1-carboxylic acid tert-butyl ester (0.36 g, 1.40 mmol) in toluene (2 mL) was added piperidine (0.7 mL, 7.00 mmol) and the resultant mixture was heated to 110° C. in a sealed tube for 18 h. The solution was concentrated in vacuo, the crude residue dissolved in DCM and washed with 0.5 N KOH (aq.) (1×) and brine (1×). The organic layer was dried (Na$_2$SO$_4$), filtered and concentrated in vacuo. The resultant oil was purified by chromatography on silica gel with MeOH:DCM (1:19, v/v) as eluent to afford 3-piperidin-1-ylmethylazetidine-1-carboxylic acid tert-butyl ester (180 mg, 0.70 mmol, 50%) as an oil.

Data for 3-piperidin-1-ylmethylazetidine-1-carboxylic acid tert-butyl ester $^1$H NMR (300 MHz, CDCl$_3$): δ 4.04 (app t, 2H), 3.60 (dd, 2H), 2.91 (br m, 1H), 2.72 (br m, 2H), 2.48 (br m, 4H), 1.71 (br m, 4H), 1.49 (br m, 2H), 1.41 (s, 9H) ppm.

c) 1-Azetidin-3-ylmethylpiperidine

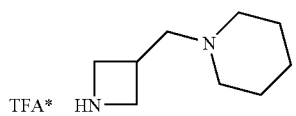

3-Piperidin-1-ylmethylazetidine-1-carboxylic acid tert-butyl ester (180 mg, 0.70 mmol) was treated with a solution of TFA:DCM (1:1 v/v, 5 mL) and the resultant solution stirred at room temperature for 1 h. The solution was concentrated in vacuo afford 1-azetidin-3-ylmethylpiperidine (INTERMEDIATE III.1) (190 mg, 0.70 mmol, 100%) as the trifluoroacetic acid salt which was used without further purification.

Data for 1-azetidin-3-ylmethylpiperidine (INTERMEDIATE III.1) trifluoroacetic acid salt: MS (ESI) m/z: 155 ([M+H]$^+$).

Similarly prepared were:

INTERMEDIATE III.2: 1-Pyrrolidin-3-ylmethylpiperidine (from commercially available tert-butyl-3-(hydroxymethyl) pyrrolidine-1-carboxylate, Pharmacore)

INTERMEDIATE III.3: 1-Piperidin-3-ylmethylpiperidine (from commercially available tert-butyl 3-(hydroxymethyl) piperidine-1-carboxylate, Pharmacore)

INTERMEDIATE III.4: (R)-1-Piperidin-3-ylmethylpiperidine (from commercially available (R)-tert-butyl 3-(hydroxymethyl)piperidine-1-carboxylate, Astatech)

INTERMEDIATE III.5: (S)-1-Piperidin-3-ylmethylpiperidine (from commercially available (S)-tert-butyl 3-(hydroxymethyl)piperidine-1-carboxylate, Astatech)

INTERMEDIATE III.6: 4-Piperidin-3-ylmethylmorpholine (from commercially available tert-butyl 3-(hydroxymethyl) piperidine-1-carboxylate, Pharmacore)

INTERMEDIATE III.7: N,N-Dimethylpiperidin-3-ylmethanamine (from commercially available tert-butyl 3-(hydroxymethyl)piperidine-1-carboxylate, Pharmacore)

INTERMEDIATE III.8: 1-(2-Azetidin-3-ylethyl)piperidine (from tert-butyl 3-(2-hydroxyethyl)azetidine-1-carboxylate (prepared according to Duggan, M. E., et al., U.S. Pat. No. 5,281,585)

Procedure IV

INTERMEDIATE IV.1: 5-Fluoro-N-(isopropylcarbamoylmethyl)-2-nitrobenzamide

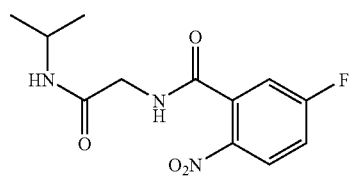

To a solution of 5-fluoro-2-nitrobenzoic acid (370 mg, 2.0 mmol) in anhydrous DMF (5 mL) was added 1-hydroxybenzotriazole hydrate (330 mg, 2.4 mmol), 1-(3-dimethylaminopropyl)-3-ethylcarbodiimide hydrochloride (460 mg, 2.4 mmol) and 2-amino-N-isopropylacetamide (INTERMEDIATE I.1) (230 mg, 2.0 mmol). The resultant mixture was stirred at room temperature for 18 h. The reaction mixture was concentrated in vacuo, the crude yellow residue dissolved in EtOAc (20 mL) and washed with dilute HCl (aq.) (3×5 mL), sat. NaHCO$_3$ (aq.) (3×5 mL) and brine (1×5 mL). The organic layer was dried (Na$_2$SO$_4$), concentrated in vacuo and purified by chromatography on silica gel with MeOH:DCM (1:19, v/v) as eluent to afford 5-fluoro-N-(isopropylcarbamoylmethyl)-2-nitrobenzamide (INTERMEDIATE IV.1) (400 mg, 1.4 mmol, 70%) as yellow solid.

Data for 5-fluoro-N-(isopropylcarbamoylmethyl)-2-nitrobenzamide (INTERMEDIATE IV.1): $^1$H NMR (300 MHz, CDCl$_3$): δ 8.15 (dd, 1H), 7.2-7.3 (m, 2H), 6.94 (br s, 1H), 6.18 (br d, 1H), 4.07 (s, 2H), 4.06 (septet, 1H), 1.19 (d, 6H) ppm; MS (ESI) m/z: 283 ([M+H]$^+$).

Similarly prepared were:

INTERMEDIATE IV.2: N-(tert-Butylcarbamoylmethyl)5-fluoro-2-nitrobenzamide (from INTERMEDIATE I.2)

INTERMEDIATE IV.3: (5-Fluoro-2-nitrobenzoylamino) acetic acid tert-butyl ester (from glycine tert-butyl ester)

Procedure V

INTERMEDIATE V.1: 2-Amino-N-(isopropylcarbamoylmethyl)-5-(4-methylperhydro-1,4-diazepin-1-yl)benzamide

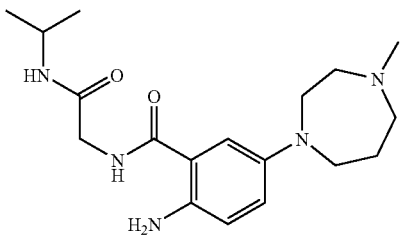

a) N-(Isopropylcarbamoylmethyl)-5-(4-methylperhydro-1,4-diazepin-1-yl)-2-nitrobenzamide

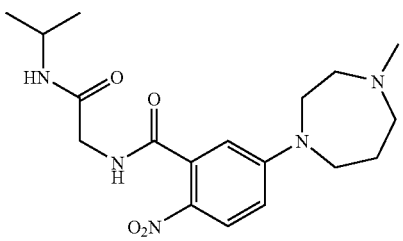

A mixture of 5-fluoro-N-(isopropylcarbamoylmethyl)-2-nitrobenzamide (INTERMEDIATE IV.1) (400 mg, 1.4 mmol), 1-methylhomopiperazine (0.20 mL, 1.6 mmol) and potassium carbonate (1 g) in acetonitrile (20 mL) were heated at reflux temperature under an Argon atmosphere for 16 h. The mixture was cooled, filtered, the residue washed with DCM (2×1 mL) and the volatiles evaporated under reduced pressure. The red coloured residue was dissolved in DCM (15 mL), washed with 1 N NaOH (aq.) (2×5 mL) and brine (1×5 mL), dried ($Na_2SO_4$) and concentrated under reduced pressure to afford N-(isopropylcarbamoylmethyl)-5-(4-methylperhydro-1,4-diazepin-1-yl)-2-nitrobenzamide (510 mg, 1.4 mmol, 100%) as an orange-red solid. This was used in the next step without further purification.

Data for N-(isopropylcarbamoylmethyl)-5-(4-methylperhydro-1,4-diazepin-1-yl)-2-nitrobenzamide: MS (ESI) m/z: 378 ($[M+H]^+$).

b) 2-Amino-N-(isopropylcarbamoylmethyl)-5-(4-methylperhydro-1,4-diazepin-1-yl)benzamide

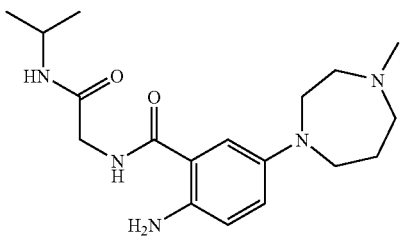

A mixture of N-(isopropylcarbamoylmethyl)-5-(4-methylperhydro-1,4-diazepin-1-yl)-2-nitrobenzamide (510 mg, 1.4 mmol) and 10% Pd/C (60 mg) in MeOH (30 mL) was shaken under 50 psi $H_2$ (g) in a Parr shaker for 5 h. The mixture was filtered through a pad of celite and the solvent removed in vacuo to afford 2-amino-N-(isopropylcarbamoylmethyl)-5-(4-methylperhydro-1,4-diazepin-1-yl)benzamide (INTERMEDIATE V.1) (470 mg, 1.4 mmol, 100%) as a brownish-green glass.

Data for 2-amino-N-(isopropylcarbamoylmethyl)-5-(4-methylperhydro-1,4-diazepin-1-yl)benzamide (INTERMEDIATE V.1): $^1$H NMR (300 MHz, $CDCl_3$): δ 7.38 (br s, 1H), 6.6-6.8 (m, 3H), 6.22 (br d, 1H), 4.36 (br s, 2H, $NH_2$), 4.0-4.2 (m, 3H), 3.47-3.51 (m, 2H), 3.39 (t, 2H), 2.72 (dd, 2H), 2.60 (dd, 2H), 2.38 (s, 3H), 2.00 (m, 2H), 1.16 (d, 6H) ppm; MS (ESI) m/z: 348 ($[M+H]^+$).

Similarly prepared were:

INTERMEDIATE V.2: 4-{4-Amino-3-[(isopropylcarbamoylmethyl)carbamoyl]phenyl}perhydro-1,4-diazepine-1-carboxylic acid tert-butyl ester (from INTERMEDIATE IV.1)

INTERMEDIATE V.3: 4-{4-Amino-3-[(isopropylcarbamoylmethyl)carbamoyl]phenyl}piperazine-1-carboxylic acid tert-butyl ester (from INTERMEDIATE IV.1)

INTERMEDIATE V.4: 2-Amino-5-(3-dimethylaminopyrrolidin-1-yl) N-(isopropylcarbamoylmethyl)benzamide (from INTERMEDIATE IV.1)

INTERMEDIATE V.5: 2-Amino-5-(3-dimethylaminomethylpiperidin-1-yl)-N-(isopropylcarbamoylmethyl)benzamide (from INTERMEDIATE IV.1 and INTERMEDIATE III.7)

INTERMEDIATE V.6: 2-Amino-N-(isopropylcarbamoylmethyl)-5-(4-methylpiperazin-1-yl)benzamide (from INTERMEDIATE IV.1)

INTERMEDIATE V.7: 2-Amino-N-(isopropylcarbamoylmethyl)-5-((S)-3-piperidin-1-ylmethylpiperidin-1-yl)benzamide (from INTERMEDIATE IV.1 and INTERMEDIATE III.5)

INTERMEDIATE V.8: 2-Amino-5-(4-dimethylaminopiperidin-1-yl)-N-(isopropylcarbamoylmethyl)benzamide (from INTERMEDIATE IV.1)

INTERMEDIATE V.9: 2-Amino-N-(isopropylcarbamoylmethyl)-5-((R)-3-piperidin-1-ylmethylpiperidin-1-yl)benzamide (from INTERMEDIATE IV.1 and INTERMEDIATE III.4)

INTERMEDIATE V.10: 2-Amino-N-(isopropylcarbamoylmethyl)-5-(3-piperidin-1-ylmethylpiperidin-1-yl)benzamide (from INTERMEDIATE IV.1 and INTERMEDIATE III.3)

INTERMEDIATE V.11: 2-Amino-N-(isopropylcarbamoylmethyl)-5-(3-piperidin-1-ylmethyl-azetidin-1-yl)benzamide (from INTERMEDIATE IV.1 and INTERMEDIATE III.1)

INTERMEDIATE V.12: 2-Amino-N-(isopropylcarbamoylmethyl)-5-(4-phenylperhydro-1,4-diazepin-1-yl)benzamide (from INTERMEDIATE IV.1)

INTERMEDIATE V.13: 2-Amino-N-(tert-butylcarbamoylmethyl)-5-(4-methylperhydro-1,4-diazepin-1-yl)benzamide (from INTERMEDIATE IV.2)

INTERMEDIATE V.14: 2-Amino-N-(isopropylcarbamoylmethyl)-5-(3-piperidin-1-ylmethylpyrrolidin-1-yl)benzamide (from INTERMEDIATE IV.1 and INTERMEDIATE III.2)

INTERMEDIATE V.15: 2-Amino-5-[1,4']bipiperidinyl-1'-yl-N-(isopropylcarbamoylmethyl)benzamide (from INTERMEDIATE IV.1)

INTERMEDIATE V.16: 2-Amino-N-(isopropylcarbamoylmethyl)-5-[3-(2-piperidin-1-ylethyl)azetidin-1-yl]benzamide (from INTERMEDIATE IV.1 and INTERMEDIATE III.8)

INTERMEDIATE V.17: 2-Amino-N-(isopropylcarbamoylmethyl)-5-(3-morpholin-4-ylmethylpiperidin-1-yl)benzamide (from INTERMEDIATE IV.1 and INTERMEDIATE III.6)

INTERMEDIATE V.18: 2-Amino-N-(isopropylcarbamoylmethyl)-5-((S)-3-methylpiperazin-1-yl)benzamide (from INTERMEDIATE IV.1)

INTERMEDIATE V.19: 2-Amino-5-(3,3-dimethylpiperazin-1-yl)-N-(isopropylcarbamoylmethyl)benzamide (from INTERMEDIATE IV.1)

INTERMEDIATE V.20: 2-Amino-5-(2,5-dimethylpiperazin-1-yl)-N-(isopropylcarbamoylmethyl)benzamide (from INTERMEDIATE IV.1)

INTERMEDIATE V.21: [2-Amino-5-(hexahydropyrrolo[1,2-a]pyrazin-2-yl)benzoylamino]acetic acid tert-butyl ester (from INTERMEDIATE IV.3)

INTERMEDIATE V.22: 2-Amino-5-[4-(2-hydroxyethyl)perhydro-1,4-diazepin-1-yl]-N-(isopropylcarbamoylmethyl)benzamide (from INTERMEDIATE IV.1)

INTERMEDIATE V.23: 2-Amino-N-(isopropylcarbamoylmethyl)-5-(4-isopropylpiperazin-1-yl)benzamide (from INTERMEDIATE IV.1)

INTERMEDIATE V.24: 2-Amino-5-(3,5-dimethylpiperazin-1-yl)-N-(isopropylcarbamoylmethyl)benzamide (from INTERMEDIATE IV.1)

INTERMEDIATE V.25: 2-Amino-N-(isopropylcarbamoylmethyl)-5-((R)-3-methylpiperazin-1-yl)benzamide (from INTERMEDIATE IV.1)

INTERMEDIATE V.26: 2-Amino-5-(3-ethylperhydro-1,4-diazepin-1-yl)-N-(isopropylcarbamoylmethyl)benzamide (from INTERMEDIATE IV.1 and INTERMEDIATE X.1)

INTERMEDIATE V.27: 2-Amino-5-(3-fluoromethylpiperazin-1-yl)-N-(isopropylcarbamoylmethyl)benzamide (from INTERMEDIATE IV.1 and INTERMEDIATE XII.1)

INTERMEDIATE V.28: 2-Amino-N-(isopropylcarbamoylmethyl)-5-((S)-2-pyrrolidin-1-ylmethylpyrrolidin-1-yl)benzamide (from INTERMEDIATE IV.1)

INTERMEDIATE V.29: 2-Amino-N-(isopropylcarbamoylmethyl)-5-(5-methylperhydro-1,4-diazepin-1-yl)benzamide (from INTERMEDIATE IV.1 and INTERMEDIATE XI.1)

INTERMEDIATE V.30: [2-Amino-5-(4-ethylperhydro-1,4-diazepin-1-yl)benzoylamino]acetic acid tert-butyl ester (from INTERMEDIATE IV.3)

INTERMEDIATE V.31: 2-Amino-N-(isopropylcarbamoylmethyl)-5-(4-isopropylperhydro-1,4-diazepin-1-yl)benzamide (from INTERMEDIATE IV.1)

INTERMEDIATE V.32: 2-Amino-N-(isopropylcarbamoylmethyl)-5-(3-propylperhydro-1,4-diazepin-1-yl)benzamide (from INTERMEDIATE IV.1 and INTERMEDIATE X.3)

INTERMEDIATE V.33: 2-Amino-N-(isopropylcarbamoylmethyl)-5-[3-(2-methanesulfonylethyl)perhydro-1,4-diazepin-1-yl]benzamide (from INTERMEDIATE IV.1 and INTERMEDIATE X.4)

INTERMEDIATE V.34: 2-Amino-N-(isopropylcarbamoylmethyl)-5-((S)-3-isopropylperhydro-1,4-diazepin-1-yl)benzamide (from INTERMEDIATE IV.1 and INTERMEDIATE X.5)

INTERMEDIATE V.35: 2-Amino-N-(isopropylcarbamoylmethyl)-5-((R)-3-isopropylperhydro-1,4-diazepin-1-yl)benzamide (from INTERMEDIATE IV.1 and INTERMEDIATE X.6)

INTERMEDIATE V.36: 2-Amino-N-(isopropylcarbamoylmethyl)-5-((R)-3-isopropylpiperazin-1-yl)benzamide (from INTERMEDIATE IV.1)

INTERMEDIATE V.37: 2-Amino-N-(isopropylcarbamoylmethyl)-5-((S)-3-isopropylpiperazin-1-yl)benzamide (from INTERMEDIATE IV.1)

INTERMEDIATE V.38: 4-{4-Amino-3-[(tert-butylcarbamoylmethyl)carbamoyl]phenyl}perhydro-1,4-diazepine-1-carboxylic acid tert-butyl ester (from INTERMEDIATE IV.2)

INTERMEDIATE V.39: [2-Amino-5-(6,6-dimethyl-3-propylperhydro-1,4-diazepin-1-yl)benzoylamino]acetic acid tert-butyl ester (from INTERMEDIATE IV.3 and INTERMEDIATE X.9)

INTERMEDIATE V.40: [2-Amino-5-((S)-3-isopropylperhydro-1,4-diazepin-1-yl)benzoylamino]acetic acid tert-butyl ester (from INTERMEDIATE IV.3 and INTERMEDIATE X.11)

INTERMEDIATE V.41: {2-Amino-5-[4-(2-hydroxyethyl)perhydro-1,4-diazepin-1-yl]benzoylamino}acetic acid tert-butyl ester (from INTERMEDIATE IV.3)

INTERMEDIATE V.42: (S)-4-{4-Amino-3-[(isopropylcarbamoylmethyl)carbamoyl]phenyl}-2-isopropylpiperazine-1-carboxylic acid tert-butyl ester (from INTERMEDIATE IV.1)

INTERMEDIATE V.43: [2-Amino-5-(6,6-dimethylperhydro-1,4-diazepin-1-yl)benzoylamino]acetic acid tert-butyl ester (from INTERMEDIATE IV.3 and INTERMEDIATE X.10)

INTERMEDIATE V.44: [2-Amino-5-(3,6,6-trimethylperhydro-1,4-diazepin-1-yl)benzoylamino]acetic acid tert-butyl ester (from INTERMEDIATE IV.3 and INTERMEDIATE X.7)

INTERMEDIATE V.45: [2-Amino-5-(3-ethyl-6,6-dimethylperhydro-1,4-diazepin-1-yl)benzoylamino]acetic acid tert-butyl ester (from INTERMEDIATE IV.3 and INTERMEDIATE X.8)

INTERMEDIATE V.46: 2-Amino-N-(isopropylcarbamoylmethyl)-5-(octahydropyrido[1,2-a]pyrazin-2-yl)benzamide (from INTERMEDIATE IV.1)

INTERMEDIATE V.47: 2-Amino-5-(1,4-diazabicyclo[3.2.2]non-4-yl)-N-(isopropylcarbamoylmethyl)benzamide (from INTERMEDIATE IV.1)

INTERMEDIATE V.48: 2-Amino-5-(hexahydropyrrolo[1,2-a]pyrazin-2-yl)-N-(isopropylcarbamoylmethyl)benzamide (from INTERMEDIATE IV.1)

INTERMEDIATE V.49: 2-Amino-N-(tert-butylcarbamoylmethyl)-5-(4-isopropylperhydro-1,4-diazepin-1-yl)benzamide (from INTERMEDIATE IV.2)

INTERMEDIATE V.50: [2-Amino-5-((R)-3-methylpiperazin-1-yl)benzoylamino]acetic acid tert-butyl ester (from INTERMEDIATE IV.3)

INTERMEDIATE V.51: [2-Amino-5-(1,4-diazabicyclo[3.2.2]non-4-yl)benzoylamino]acetic acid tert-butyl ester (from INTERMEDIATE IV.3)

INTERMEDIATE V.52: [2-Amino-5-(4-isopropylperhydro-1,4-diazepin-1-yl)benzoylamino]acetic acid tert-butyl ester (from INTERMEDIATE IV.3)

INTERMEDIATE V.53: 4-{4-Amino-3-[(isopropylcarbamoylmethyl)carbamoyl]phenyl}-2-methylperhydro-1,4-diazepine-1-carboxylic acid tert-butyl ester

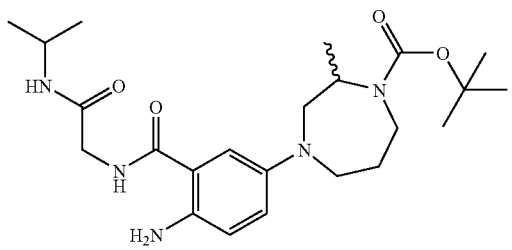

a) N-(Isopropylcarbamoylmethyl)-5-(3-methylperhydro-1,4-diazepin-1-yl)-2-nitrobenzamide

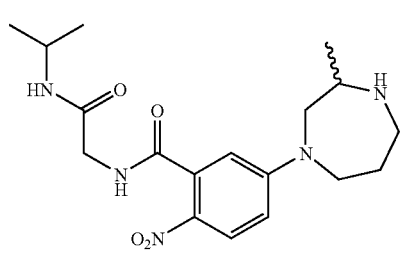

5-Fluoro-N-(isopropylcarbamoylmethyl)-2-nitrobenzamide (INTERMEDIATE IV.1) (150 mg, 0.530 mmol), 2-methylperhydro-1,4-diazepine (INTERMEDIATE X.2) (61 mg, 0.530 mmol) and potassium carbonate (220 mg, 1.589 mmol) in acetonitrile (3 mL) were stirred at room temperature for 48 h followed by heating at 50-60° C. for 2 h. The reaction mixture was filtered through a silica plug, solvent evaporated under reduced pressure and crude product purified by chromatography on silica gel with a gradient of DCM to DCM:MeOH (4:1, v/v) as eluent. This afforded N-isopropylcarbamoylmethyl)-5-(3-methylperhydro-1,4-diazepin-1-yl)-2-nitrobenzamide (72 mg, 0.191 mmol, 36%).

Data for N-isopropylcarbamoylmethyl)-5-(3-methylperhydro-1,4-diazepin-1-yl)-2-nitrobenzamide: MS (ESI) m/z: 379 ([M+H]$^+$).

b) 4-{3-[(Isopropylcarbamoylmethyl)carbamoyl]-4-nitrophenyl}-2-methylperhydro-1,4-diazepine-1-carboxylic acid tert-butyl ester

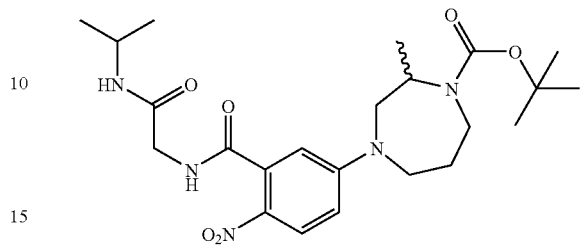

N-(Isopropylcarbamoylmethyl)-5-(3-methylperhydro-1,4-diazepin-1-yl)-2-nitrobenzamide (72 mg, 0.191 mmol) and di-tert-butyldicarbonate (42 mg, 0.191 mmol) in DCM (5 mL) were stirred at room temperature overnight. Solvent was evaporated under reduced pressure to afford crude 4-{3-[(isopropylcarbamoylmethyl)carbamoyl]-4-nitrophenyl}-2-methylperhydro-1,4-diazepine-1-carboxylic acid tert-butyl ester (100 mg, 0.209 mmol, 100%) which was used directly in the next step.

c) 4-{4-Amino-3-[(isopropylcarbamoylmethyl)carbamoyl]phenyl}-2-methylperhydro-1,4-diazepine-1-carboxylic acid tert-butyl ester

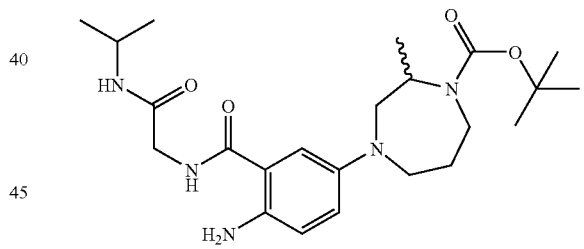

4-{3-[(Isopropylcarbamoylmethyl)carbamoyl]-4-nitrophenyl}-2-methylperhydro-1,4-diazepine-1-carboxylic acid tert-butyl ester (100 mg, 0.209 mmol) and 10% Pd/C (10 mg, 0.209 mmol) in MeOH (5 mL) was stirred under 4 bar H$_2$ (g) at room temperature overnight. The mixture was filtered through a pad of celite and the solvent removed in vacuo to afford 4-{4-amino-3-[(isopropylcarbamoylmethyl)carbamoyl]phenyl}-2-methylperhydro-1,4-diazepine-1-carboxylic acid tert-butyl ester (INTERMEDIATE V.53) (94 mg, 0.210 mmol, 100%). This was used directly without purification.

Similarly prepared was:

INTERMEDIATE V.54: 4-{4-Amino-3-[(isopropylcarbamoylmethyl)carbamoyl]phenyl}-6,6-dimethylperhydro-1,4-diazepine-1-carboxylic acid tert-butyl ester (from INTERMEDIATE IV.1 and INTERMEDIATE X.10)

INTERMEDIATE V.55: 4-{4-Amino-3-[(isopropylcarbamoylmethyl)carbamoyl]phenyl}-6-fluoroperhydro-1,4-diazepine-1-carboxylic acid tert-butyl ester (from INTERMEDIATE IV.1 and XII.2)

Procedure VI

INTERMEDIATE VI.1: 2-[6-Bromo-2-(3-chlorophenyl)-4-oxo-4H-quinazolin-3-yl]-N-tert-butylacetamide

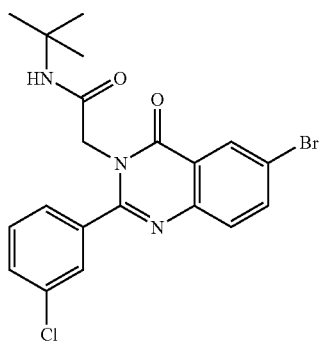

a) 2-Amino-5-bromo-N-(tert-butylcarbamoylmethyl)benzamide

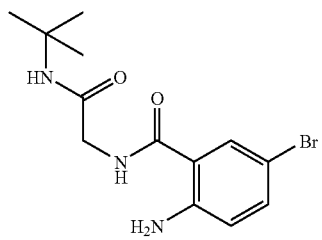

A suspension of 5-bromoisatoic anhydride (1.2 g, 5.0 mmol) and 2-amino-N-tert-butylacetamide (INTERMEDIATE I.2) (0.78 g, 6.0 mmol) in acetonitrile (8 mL) was stirred at room temperature for 20 h. The white suspension was filtered, and the white precipitate washed cold EtOH to give 2-amino-5-bromo-N-(tert-butylcarbamoylmethyl)benzamide (1.06 g, 3.22 mmol, 65%).

Data for 2-amino-5-bromo-N-(tert-butylcarbamoylmethyl)benzamide: $^1$H NMR (300 MHz, d$^6$-DMSO): δ 8.44 (t, 1H), 7.68 (d, 1H), 7.49 (s, 1H), 7.27 (dd, 1H), 6.67 (d, 1H), 6.56 (br s, 1H), 3.73 (d, 1H), 3.33 (br s, 2H), 1.26 (s, 9H) ppm; MS (ESI) m/z: 328/330 ([M+H]$^+$).

b) 2-[6-Bromo-2-(3-chlorophenyl)-4-oxo-1,4-dihydro-2H-quinazolin-3-yl]-N-tert-butylacetamide

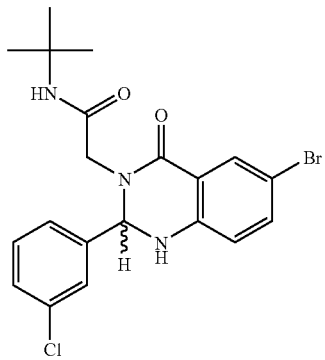

In a capped 20 mL scintillation vial, a solution of 2-amino-5-bromo-N-(tert-butylcarbamoylmethyl)benzamide (0.65 g, 2.0 mmol), 3-chlorobenzaldehyde (0.27 mL, 2.4 mmol) and catalytic glacial acetic acid (2 drops) in anhydrous ethanol (10 mL) was heated with stirring at 85° C. for 16 h. The resulting white suspension was cooled to room temperature, the white solid collected by suction filtration and washed with cold EtOH to give 2-[6-bromo-2-(3-chlorophenyl)-4-oxo-1,4-dihydro-2H-quinazolin-3-yl]-N-tert-butylacetamide (0.53 g, 1.21 mmol, 58%).

Data for 2-[6-bromo-2-(3-chlorophenyl)-4-oxo-1,4-dihydro-2H-quinazolin-3-yl]-N-tert-butylacetamide: MS (ESI) m/z: 450/452 ([M+H]$^+$).

c) 2-(6-Bromo-2-(3-chlorophenyl)-4-oxoquinazolin-3(4H)-yl)-N-tert-butylacetamide

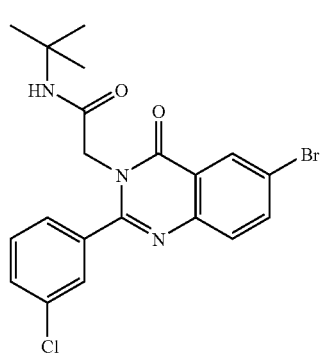

In a capped 20 mL scintillation vial, a mixture of 2-[6-bromo-2-(3-chlorophenyl)-4-oxo-1,4-dihydro-2H-quinazolin-3-yl]-N-tert-butylacetamide (0.51 g, 1.13 mmol) and manganese(IV) dioxide (0.44 g, 5.10 mmol) in chloroform (10 mL) was heated at 70° C. for 3 h. The black suspension was cooled to room temperature, filtered through a pad of celite and concentrated in vacuo to provide 2-[6-bromo-2-(3-chlorophenyl)-4-oxo-4H-quinazolin-3-yl]-N-tert-butylacetamide (INTERMEDIATE VI.1) (0.51 g, 1.13 mmol, 100%) as a white solid. Data for 2-[6-bromo-2-(3-chlorophenyl)-4-oxo-4H-quinazolin-3-yl]-N-tert-butylacetamide (INTERMEDIATE VI.1): $^1$H NMR (300 MHz, CDCl$_3$): δ 9.44 (d, 1H), 7.86 (dd, 1H), 7.65-7.54 (m, 2H), 7.53-7.4 (m, 3H), 5.47 (s, 1H), 4.46 (s, 2H), 1.34 (s, 9H) ppm; MS (ESI) m/z: 448/450 ([M+H]+).

Procedure VII

INTERMEDIATE VII.1: 4-[3-(Isopropylcarbamoyl-methyl)-2-(3-methoxyphenyl)-4-oxo-3,4-dihydro-quinazolin-6-yl]perhydro-1,4-diazepine-1-carboxylic acid tert-butyl ester

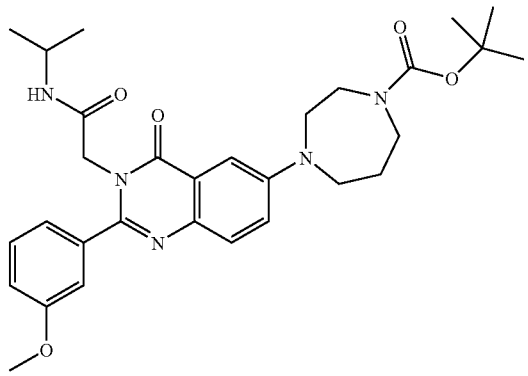

A mixture of 4-{4-Amino-3-[(isopropylcarbamoylmethyl)carbamoyl]phenyl}perhydro-1,4-diazepine-1-carboxylic acid tert-butyl ester (INTERMEDIATE V.2) (300 mg, 0.69 mmol) and ethyl 3-methoxybenzimidate hydrochloride (INTERMEDIATE II.2) (298 mg, 1.38 mmol) in EtOH (6 mL) was heated at reflux temperature for 16 h. The reaction mixture was cooled, filtered and the filtrate concentrated in vacuo. The crude residue was purified by preparative HPLC to afford 4-[3-(isopropylcarbamoylmethyl)-2-(3-methoxyphenyl)-4-oxo-3,4-dihydroquinazolin-6-yl]perhydro-1,4-diazepine-1-carboxylic acid tert-butyl ester (INTERMEDIATE VII.1) (50 mg, 0.09 mmol, 13%).

Similarly prepared were:

INTERMEDIATE VII.2: 4-[2-(3-Chlorophenyl)-3-(isopropylcarbamoylmethyl)-4-oxo-3,4-dihydroquinazolin-6-yl]perhydro-1,4-diazepine-1-carboxylic acid tert-butyl ester (from INTERMEDIATE V.2 and 11.1)

INTERMEDIATE VII.3: 4-[2-(3-Chlorophenyl)-3-(isopropylcarbamoylmethyl)-4-oxo-3,4-dihydroquinazolin-6-yl]piperazine-1-carboxylic acid tert-butyl ester (from INTERMEDIATE V.3 and 11.1)

INTERMEDIATE VII.4: 4-[3-(tert-Butylcarbamoylmethyl)-2-(3-chloro-4-fluorophenyl)-4-oxo-3,4-dihydroquinazolin-6-yl]perhydro-1,4-diazepine-1-carboxylic acid tert-butyl ester (from INTERMEDIATE V.38 and 11.4)

INTERMEDIATE VII.5: 4-[3-(tert-Butylcarbamoylmethyl)-2-(4-fluoro-3-methoxyphenyl)-4-oxo-3,4-dihydroquinazolin-6-yl]perhydro-1,4-diazepine-1-carboxylic acid tert-butyl ester (from INTERMEDIATE V.38 and 11.3)

INTERMEDIATE VII.6: 4-[2-(3-Chloro-4-fluorophenyl)-3-(isopropylcarbamoylmethyl)-4-oxo-3,4-dihydroquinazolin-6-yl]perhydro-1,4-diazepine-1-carboxylic acid tert-butyl ester (from INTERMEDIATE V.2 and 11.4)

INTERMEDIATE VII.7: 4-[2-(4-Fluoro-3-methoxyphenyl)-3-(isopropylcarbamoylmethyl)-4-oxo-3,4-dihydroquinazolin-6-yl]perhydro-1,4-diazepine-1-carboxylic acid tert-butyl ester (from INTERMEDIATE V.2 and 11.3)

INTERMEDIATE VII.8: [2-(3-Chloro-4-fluorophenyl)-6-(4-ethylperhydro-1,4-diazepin-1-yl)-4-oxo-4H-quinazolin-3-yl]acetic acid tert-butyl ester (from INTERMEDIATE V.30 and 11.4)

INTERMEDIATE VII.9: {2-(4-Fluoro-3-methoxyphenyl)-6-[4-(2-hydroxyethyl)perhydro-1,4-diazepin-1-yl]-4-oxo-4H-quinazolin-3-yl}acetic acid tert-butyl ester (from INTERMEDIATE V.41 and 11.3)

INTERMEDIATE VII.10: 4-[2-(4-Fluoro-3-methoxyphenyl)-3-(isopropylcarbamoylmethyl)-4-oxo-3,4-dihydroquinazolin-6-yl]-6,6-dimethylperhydro-1,4-diazepine-1-carboxylic acid tert-butyl ester (from INTERMEDIATE V.54 and 11.3)

INTERMEDIATE VII.11: 4-[2-(3-Chloro-4-fluorophenyl)-3-(isopropylcarbamoylmethyl)-4-oxo-3,4-dihydroquinazolin-6-yl]-6,6-dimethylperhydro-1,4-diazepine-1-carboxylic acid tert-butyl ester (from INTERMEDIATE V.54 and 11.2)

INTERMEDIATE VII.12: [2-(4-Fluoro-3-methoxyphenyl)-4-oxo-6-(3,6,6-trimethylperhydro-1,4-diazepin-1-yl)-4H-quinazolin-3-yl]acetic acid tert-butyl ester

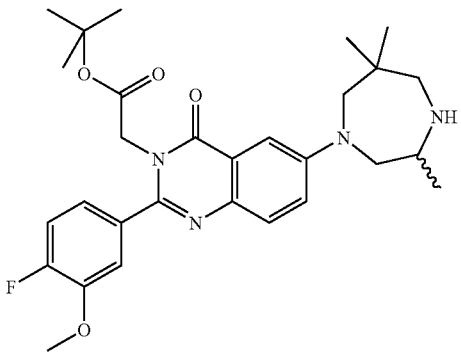

[2-Amino-5-(3,6,6-trimethylperhydro-1,4-diazepin-1-yl)benzoylamino]acetic acid tert-butyl ester (INTERMEDIATE V.44) (1.00 g, 2.56 mmol), 4-fluoro-3-methoxybenzaldehyde (414 mg, 2.69 mmol), ethanol (20 mL) and acetic acid (3 drops) were stirred overnight at reflux temperature. Solvent was evaporated under reduced pressure. The crude reaction mixture was purified by SCX with product eluted with 2N NH3/MeOH. Solvent was evaporated under reduced pressure and the product dissolved in toluene (10 mL) and water (10 mL). Potassium hexacyanoferrate (III) (8.43 g, 25.6 mmol) was added and the reaction mixture stirred vigorously overnight. The reaction was then quenched by the addition of methanol (300 mL), the mixture filtered through a celite pad and the cake washed with further methanol (200 mL). The filtrate was evaporated to dryness and purified by chromatography on silica gel with a gradient of DCM to DCM:MeOH (3:1, v/v) as eluent to afford [2-(4-fluoro-3-methoxyphenyl)-4-oxo-6-(3,6,6-trimethylperhydro-1,4-diazepin-1-yl)-4H-quinazolin-3-yl]acetic acid tert-butyl ester (INTERMEDIATE VII.12) (160 mg, 0.305 mmol, 12%).

INTERMEDIATE VII.13: [2-(3-Chloro-4-fluorophenyl)-6-(1,4-diazabicyclo[3.2.2]non-4-yl)-4-oxo-4H-quinazolin-3-yl]acetic acid tert-butyl ester (from INTERMEDIATE V.51)

INTERMEDIATE VII.14: [6-(1,4-Diazabicyclo[3.2.2]non-4-yl)-2-(3,5-dimethoxyphenyl)-4-oxo-4H-quinazolin-3-yl]acetic acid tert-butyl ester (from INTERMEDIATE V.51)

INTERMEDIATE VII.15: [6-(1,4-Diazabicyclo[3.2.2]non-4-yl)-2-(4-fluoro-3-methoxyphenyl)-4-oxo-4H-quinazolin-3-yl]acetic acid tert-butyl ester (from INTERMEDIATE V.51)

INTERMEDIATE VII.16: [6-(3-Ethyl-6,6-dimethylperhydro-1,4-diazepin-1-yl)-2-(4-fluoro-3-methoxyphenyl)-4-oxo-4H-quinazolin-3-yl]acetic acid tert-butyl ester (from INTERMEDIATE V.45)

INTERMEDIATE VII.17: [2-(3-Chloro-4-fluorophenyl)-6-((R)-3-methylpiperazin-1-yl)-4-oxo-4H-quinazolin-3-yl]acetic acid tert-butyl ester (from INTERMEDIATE V.50)

INTERMEDIATE VII.18: 4-[2-(3-Chloro-4-fluorophenyl)-3-(isopropylcarbamoylmethyl)-4-oxo-3,4-dihydroquinazolin-6-yl]-2-methylperhydro-1,4-diazepine-1-carboxylic acid tert-butyl ester

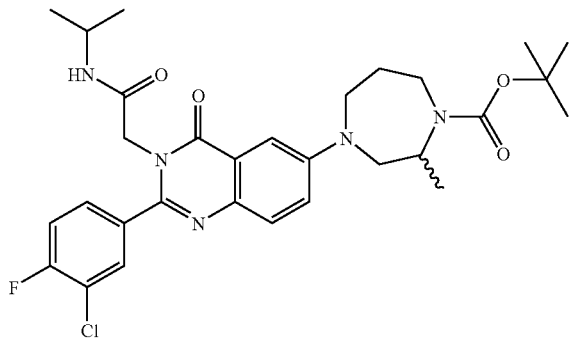

4-{4-Amino-3-[(isopropylcarbamoylmethyl)carbamoyl]phenyl}-2-methylperhydro-1,4-diazepine-1-carboxylic acid tert-butyl ester (INTERMEDIATE V.53) (94 mg, 0.201 mmol), 3-chloro-4-fluorobenzaldehyde (40 mg, 0.252 mmol) and acetic acid (3 µL, catalytic) were dissolved in ethanol (3 mL) in a microwave vial and the vial sealed. The reaction mixture was stirred at 90° C. for 16 h. The reaction mixture was evaporated to dryness, crude material dissolved in DCM (3 mL) and manganese dioxide (80 mg, 0.840 mmol) was added. The reaction mixture was stirred in a sealed vial at 60° C. for 3 h. TLC showed incomplete reaction so additional manganese dioxide (80 mg, 0.840 mmol) was added and the reaction mixture heated at 60° C. for a further 2 h. Solvent was evaporated under reduced pressure and crude product purified by chromatography on silica gel with DCM:MeOH (9:1, v/v) as eluent. This afforded 4-[2-(3-chloro-4-fluorophenyl)-3-(isopropylcarbamoylmethyl)-4-oxo-3,4-dihydroquinazolin-6-yl]-2-methylperhydro-1,4-diazepine-1-carboxylic acid tert-butyl ester (INTERMEDIATE VII.18) (65 mg, 0.111 mmol, 53%).

Data for 4-[2-(3-chloro-4-fluorophenyl)-3-(isopropylcarbamoylmethyl)-4-oxo-3,4-dihydroquinazolin-6-yl]-2-methylperhydro-1,4-diazepine-1-carboxylic acid tert-butyl ester (INTERMEDIATE VII.18): MS (ESI) m/z: 586/588 ([M+H]$^+$).

INTERMEDIATE VII.19: (S)-4-[2-(3-Chloro-4-fluorophenyl)-3-(isopropylcarbamoylmethyl)-4-oxo-3,4-dihydroquinazolin-6-yl]-2-isopropylpiperazine-1-carboxylic acid tert-butyl ester ester (from INTERMEDIATE V.42)

INTERMEDIATE VII.20: [2-(3-Chloro-4-fluorophenyl)-6-(hexahydropyrrolo[1,2-a]pyrazin-2-yl)-4-oxo-4H-quinazolin-3-yl]acetic acid tert-butyl ester (from INTERMEDIATE V.21)

INTERMEDIATE VII.21: [2-(3-Chloro-4-fluorophenyl)-6-(4-isopropylperhydro-1,4-diazepin-1-yl)-4-oxo-4H-quinazolin-3-yl]acetic acid tert-butyl ester (from INTERMEDIATE V.52)

INTERMEDIATE VII.22: [2-(3-Chloro-4-fluorophenyl)-6-(dimethylperhydro-1,4-diazepin-1-yl)-4-oxo-4H-quinazolin-3-yl]acetic acid tert-butyl ester (from INTERMEDIATE V.43)

INTERMEDIATE VII.23: [2-(3-Chlorophenyl)-6-(4-isopropylperhydro-1,4-diazepin-1-yl)-4-oxo-4H-quinazolin-3-yl]acetic acid tert-butyl ester (from INTERMEDIATE V.52)

INTERMEDIATE VII.24: [6-(4-Ethylperhydro-1,4-diazepin-1-yl)-2-(4-fluoro-3-methoxyphenyl)-4-oxo-4H-quinazolin-3-yl]acetic acid tert-butyl ester (from INTERMEDIATE V.30)

INTERMEDIATE VII.25: [6-(6,6-Dimethyl-3-propylperhydro-1,4-diazepin-1-yl)-2-(4-fluoro-3-methoxyphenyl)-4-oxo-4H-quinazolin-3-yl]acetic acid tert-butyl ester (from INTERMEDIATE V.39)

INTERMEDIATE VII.26: [2-(4-Fluoro-3-methoxyphenyl)-6-((S)-3-isopropyl-6,6-dimethylperhydro-1,4-diazepin-1-yl)-4-oxo-4H-quinazolin-3-yl]acetic acid tert-butyl ester (from INTERMEDIATE V.40)

INTERMEDIATE VII.27: 4-[2-(3-Chloro-4-fluorophenyl)-3-(isopropylcarbamoylmethyl)-4-oxo-3,4-dihydroquinazolin-6-yl]-6-fluoroperhydro-1,4-diazepine-1-carboxylic acid tert-butyl ester (from INTERMEDIATE V.55)

INTERMEDIATE VII 0.28: 4-[2-(3-Chloro-4-fluorophenyl)-3-(isopropylcarbamoylmethyl)-4-oxo-3,4-dihydroquinazolin-6-yl]piperazine-1-carboxylic acid tert-butyl ester (from INTERMEDIATE V.3)

Procedure VIII

INTERMEDIATE VII.1: 4-[3-(tert-Butylcarbamoylmethyl)-2-(3-chlorophenyl)-4-oxo-3,4-dihydroquinazolin-6-yl]perhydro-1,4-diazepine-1-carboxylic acid tert-butyl ester

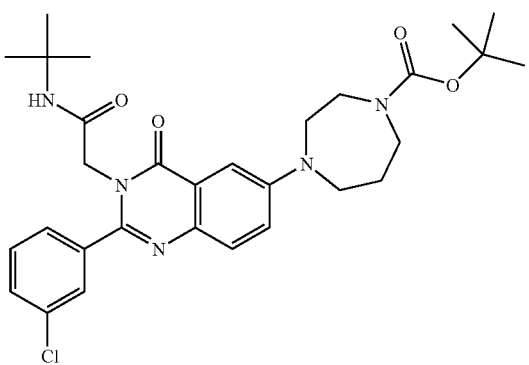

Racemic-2,2'-bis(diphenylphosphino)-1,1'-binaphthyl (5 mg, 0.009 mmol) and anhydrous toluene (0.5 mL) was heated in a microwave vial with stirring at 80° C. under an Argon atmosphere until a homogeneous milky solution was obtained (~5 min). This solution was cooled to room temperature and palladium(II) acetate (2 mg, 0.006 mmol) was added. After stirring at room temperature for 2 min., 2-[6-bromo-2-(3-chlorophenyl)-4-oxo-4H-quinazolin-3-yl]-N-tert-butylacetamide (INTERMEDIATE VI.1) (67 mg, 0.15 mmol), tert-butyl-1-homopiperazinecarboxylate (35 μL, 0.18 mmol) and freshly ground cesium carbonate (68 mg, 0.21 mmol) were added to the red solution. Anhydrous dioxane (0.2 mL) was added to rinse down solid left on the side of the vial. The vial was capped and heated in a microwave at 120° C. for 40 min. The reaction mixture was diluted with DCM (3 mL), filtered and the filtrate concentrated in vacuo. This crude product was purified by preparative TLC on silica gel with hexane:EtOAc:CH$_2$Cl$_2$ (1:1:1, v/v) as eluent to give 4-[3-(tert-butylcarbamoylmethyl)-2-(3-chlorophenyl)-4-oxo-3,4-dihydroquinazolin-6-yl]perhydro-1,4-diazepine-1-carboxylic acid tert-butyl ester (INTERMEDIATE VIII.1) (38.9 mg, 0.07 mmol, 46%) as a yellow solid.

Data for 4-[3-(tert-butylcarbamoylmethyl)-2-(3-chlorophenyl)-4-oxo-3,4-dihydroquinazolin-6-yl]perhydro-1,4-diazepine-1-carboxylic acid tert-butyl ester (INTERMEDIATE VIII.1): $^1$H NMR (300 MHz, CDCl$_3$): δ 7.7-7.4 (m, 6H), 7.3-7.2 (m, 1H), 5.70 (s, 1H), 4.43 (s, 2H), 3.7-3.6 (m, 6H), 3.3-3.2 (m, 2H), 2.02 (m, 2H), 1.33 (s, 18H) ppm; MS (ESI) m/z: 568/570 ([M+H]$^+$).

Procedure IX

INTERMEDIATE IX.1: [2-(4-Fluoro-3-methoxyphenyl)-4-oxo-6-(3,6,6-trimethylperhydro-1,4-diazepin-1-yl)-4H-quinazolin-3-yl]acetic acid

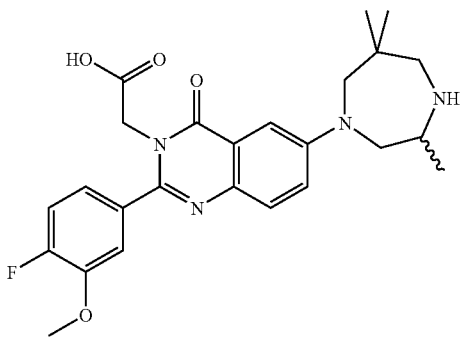

[2-(4-Fluoro-3-methoxyphenyl)-4-oxo-6-(3,6,6-trimethylperhydro-1,4-diazepin-1-yl)-4H-quinazolin-3-yl]acetic acid tert-butyl ester (INTERMEDIATE VII.12) (160 mg, 0.305 mmol) was dissolved in DCM (10 mL) and TFA (3 mL) added. The reaction mixture was stirred at room temperature overnight. Crude reaction mixture was poured directly onto an SCX cartridge, the cartridge was washed with MeOH and product eluted with 2N NH$_3$/MeOH. Solvent was removed under reduced pressure to afford [2-(4-fluoro-3-methoxyphenyl)-4-oxo-6-(3,6,6-trimethylperhydro-1,4-diazepin-1-yl)-4H-quinazolin-3-yl]acetic acid (INTERMEDIATE IX.1) which was used without further purification.

Data for [2-(4-fluoro-3-methoxyphenyl)-4-oxo-6-(3,6,6-trimethylperhydro-1,4-diazepin-1-yl)-4H-quinazolin-3-yl]acetic acid (INTERMEDIATE IX.1): MS (ES I) m/z: 469 ([M+H]$^+$).

Similarly prepared from were:

INTERMEDIATE IX.2: [6-(1,4-Diazabicyclo[3.2.2]non-4-yl)-2-(3,5-dimethoxyphenyl)-4-oxo-4H-quinazolin-3-yl]acetic acid (from INTERMEDIATE VII.14)

INTERMEDIATE IX.3: [6-(3-Ethyl-6,6-dimethylperhydro-1,4-diazepin-1-yl)-2-(4-fluoro-3-methoxyphenyl)-4-oxo-4H-quinazolin-3-yl]acetic acid (from INTERMEDIATE VII.16)

INTERMEDIATE IX.4: [2-(3-Chloro-4-fluorophenyl)-6-(dimethylperhydro-1,4-diazepin-1-yl)-4-oxo-4H-quinazolin-3-yl]acetic acid (from INTERMEDIATE VII.22)

INTERMEDIATE IX.5: [6-(6,6-Dimethyl-3-propylperhydro-1,4-diazepin-1-yl)-2-(4-fluoro-3-methoxyphenyl)-4-oxo-4H-quinazolin-3-yl]acetic acid (from INTERMEDIATE VII.25)

INTERMEDIATE IX.6: [2-(4-Fluoro-3-methoxyphenyl)-6-((S)-3-isopropyl-6,6-dimethylperhydro-1,4-diazepin-1-yl)-4-oxo-4H-quinazolin-3-yl]acetic acid (from INTERMEDIATE VII.26)

INTERMEDIATE IX.7: [6-(1,4-Diazabicyclo[3.2.2]non-4-yl)-2-(4-fluoro-3-methoxyphenyl)-4-oxo-4H-quinazolin-3-yl]acetic acid (from INTERMEDIATE VII.15)

INTERMEDIATE IX.8: [2-(3-Chloro-4-fluorophenyl)-6-((R)-3-methylpiperazin-1-yl)-4-oxo-4H-quinazolin-3-yl]acetic acid (from INTERMEDIATE VII.17)

INTERMEDIATE IX.9: [2-(3-Chloro-4-fluorophenyl)-6-(hexahydropyrrolo[1,2-a]pyrazin-2-yl)-4-oxo-4H-quinazolin-3-yl]acetic acid (from INTERMEDIATE VII.20)

INTERMEDIATE IX.10: [2-(3-Chloro-4-fluorophenyl)-6-(4-isopropylperhydro-1,4-diazepin-1-yl)-4-oxo-4H-quinazolin-3-yl]acetic acid (from INTERMEDIATE VII.21)

INTERMEDIATE IX.11: [6-(4-Ethylperhydro-1,4-diazepin-1-yl)-2-(4-fluoro-3-methoxyphenyl)-4-oxo-4H-quinazolin-3-yl]acetic acid (from INTERMEDIATE VII.24)

INTERMEDIATE IX.12: [2-(3-Chloro-4-fluorophenyl)-6-(4-ethylperhydro-1,4-diazepin-1-yl)-4-oxo-4H-quinazolin-3-yl]acetic acid (from INTERMEDIATE VII.8)

INTERMEDIATE IX.13: {2-(4-Fluoro-3-methoxyphenyl)-6-[4-(2-hydroxyethylperhydro-1,4-diazepin-1-yl]-4-oxo-4H-quinazolin-3-yl}acetic acid (from INTERMEDIATE VII.9)

INTERMEDIATE IX.14: [2-(3-Chlorophenyl)-6-(4-isopropylperhydro-1,4-diazepin-1-yl)-4-oxo-4H-quinazolin-3-yl]acetic acid (from INTERMEDIATE VII.23)

INTERMEDIATE IX.15: [2-(3-Chloro-4-fluorophenyl)-6-(1,4-diazabicyclo[3.2.2]non-4-yl)-4-oxo-4H-quinazolin-3-yl]acetic acid (from INTERMEDIATE VII.13)

Procedure X

INTERMEDIATE X.1:
2-Ethylperhydro-1,4-diazepine

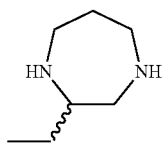

a) [3-(2-Bromobutyrylamino)propyl]carbamic acid tert-butyl ester

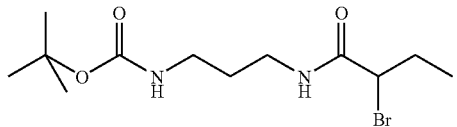

1-Propanephosphonic acid cyclic anhydride (4.11 g, 3.84 mL, 6.46 mmol) was added to a cooled solution of tert-butyl 3-aminopropylcarbamate (750 mg, 4.30 mmol), 2-bromobutanoic acid (791 mg, 0.51 mL, 4.73 mmol) and triethylamine (1.31 g, 1.82 mL, 12.91 mmol) in DCM (5 mL). The reaction mixture was stirred at room temperature for 2 h followed by addition of $Na_2CO_3$ (aq.). This was stirred for 30 min and then the organic layer separated. Solvent was evaporated under reduced pressure and crude product purified by chromatography on silica gel with DCM:MeOH (9:1, v/v) as eluent. This afforded [3-(2-bromobutyrylamino)propyl]carbamic acid tert-butyl ester (1.41 g, 4.36 mmol, 100%).

b) N-(3-Aminopropyl)-2-bromobutyramide trifluoroacetic acid salt

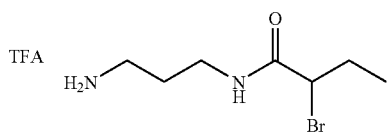

[3-(2-Bromobutyrylamino)propyl]carbamic acid tert-butyl ester (1.41 g, 4.36 mmol) was treated with TFA:DCM (1:1 (v/v), 20 mL) and the solution stirred at room temperature for 3 h. The volatiles were removed in vacuo and crude product, isolated as the trifluoroacetic acid salt, used directly in the next stage.

c) 3-Ethylperhydro-1,4-diazepin-2-one

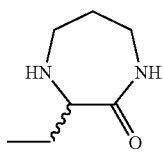

N-(3-Aminopropyl)-2-bromobutyramide trifluoroacetic acid salt (1.8 g, 5.33 mmol), $K_2CO_3$ (2.94 g, 21.33 mmol) and acetonitrile (30 mL) were combined and stirred at 140° C. in a microwave for 3500 seconds. Analysis showed presence of a considerable amount of starting material so the reaction mixture was subjected to a further 2000 seconds at 140° C. The reaction mixture was diluted with DCM (50 mL) and filtered through celite. Solvent was evaporated under reduced pressure and purified by chromatography on silica gel with a gradient of DCM to DCM:MeOH (3:1, v/v) as eluent. This afforded 3-ethylperhydro-1,4-diazepin-2-one (540 mg, 3.80 mmol, 71%).

d) 2-Ethylperhydro-1,4-diazepine

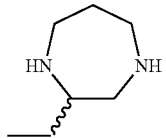

Lithium aluminium hydride (475 mg, 12.49 mmol) was added portionwise to a stirred solution of 3-ethylperhydro-1,4-diazepin-2-one (740 mg, 5.20 mmol) in THF (10 mL). After the resultant effervescence had subsided, the reaction mixture was heated at 50-60° C. for 3 h. The reaction mixture was cooled and quenched by the slow addition of water and 10% NaOH (aq.). The reaction mixture was diluted with diethyl ether (20 mL) and filtered through celite. The filter cake was washed thoroughly with THF (50 mL), diethyl ether (50 mL), THF (50 mL) and diethyl ether (50 mL). Evaporation under reduced pressure afforded 2-ethylperhydro-1,4-diazepine (INTERMEDIATE X.1) (615 mg, 5.20 mmol), 92%).

Similarly prepared were:

INTERMEDIATE X.2: 2-Methylperhydro-1,4-diazepine

INTERMEDIATE X.3: 2-Propylperhydro-1,4-diazepine

INTERMEDIATE X.4: 2-(2-Methanesulfonylethyl)perhydro-1,4-diazepine

INTERMEDIATE X.5: (S)-2-Isopropylperhydro-1,4-diazepine

INTERMEDIATE X.6: (R)-2-Isopropylperhydro-1,4-diazepine

INTERMEDIATE X.7: 2,6,6-Trimethylperhydro-1,4-diazepine

INTERMEDIATE X.8: 2-Ethyl-6,6-dimethylperhydro-1,4-diazepine

INTERMEDIATE X.9: 6,6-Dimethyl-2-propylperhydro-1,4-diazepine

INTERMEDIATE X.10: 6,6-Dimethylperhydro-1,4-diazepine

INTERMEDIATE X.11: 6,6-Dimethyl-(S)-2-isopropylperhydro-1,4-diazepine

Procedure XI

INTERMEDIATE XI.1: 5-Methyl-1,4-diazepane

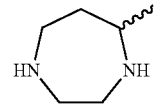

a) 7-Methyl-1,4-diazepan-5-one

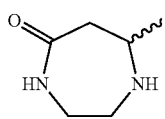

Ethane-1,2-diamine (1.35 g, 22.44 mmol) and (E)-ethyl but-2-enoate (2.56 g, 22.44 mmol) in MeOH (22 mL) was stirred at room temperature overnight. Solvent was evaporated under reduced pressure and crude product purified by chromatography on silica gel with a gradient of DCM to DCM:2M NH$_3$/MeOH (4:1, v/v) as eluent. This afforded a mixture of desired product and uncyclised material. The mixture was diluted with MeOH (4 mL) and heated in the microwave at 150° C. for 10 min followed by 160° C. for 10 min. Sodium bicarbonate (100 mg) was added and the reaction mixture stirred at room temperature for 48 h. The reaction mixture was filtered, solvent evaporated under reduced pressure and crude product purified by chromatography on silica gel with a gradient of DCM to DCM:2M NH$_3$/MeOH (4:1, v/v) as eluent to afford 7-methyl-1,4-diazepan-5-one (310 mg, 2.42 mmol, 11%).

b) 5-Methyl-1,4-diazepane

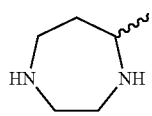

Similar procedure to INTERMEDIATE X.1 step d) from 7-methyl-1,4-diazepan-5-one (356 mg, 2.75 mmol) and lithium aluminium hydride (1M in THF) (249 mg, 6.56 mL, 6.56 mmol) to afford 5-methyl-1,4-diazepane (INTERMEDIATE XI.1) (235 mg, 2.06 mmol, 74%)

Procedure XII

INTERMEDIATE XII.1: 2-Fluoromethylpiperazine

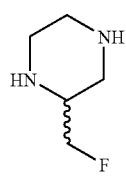

a) 1,4-Dibenzylpiperazine-2-carboxylic acid ethyl ester

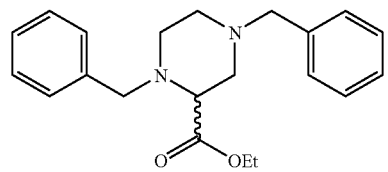

A solution of N,N-dibenzylethylenediamine (980 µL, 4.10 mmol) and triethylamine (1.03 mL, 7.38 mmol) in toluene (15 mL) was added dropwise to a solution of 2-bromopropionic acid ethyl ester (601 µL, 4.14 mmol) in toluene (15 mL). The reaction mixture was stirred at 80° C. for 72 h. The reaction mixture was filtered through a pad of celite and solvent evaporated under reduced pressure to afford 1,4-dibenzylpiperazine-2-carboxylic acid ethyl ester (1.33 g, 3.93 mmol, 96%) as a yellow oil.

Data for 1,4-dibenzylpiperazine-2-carboxylic acid ethyl ester MS (ESI) m/z: 339 ([M+H]$^+$).

b) (1,4-Dibenzylpiperazin-2-yl)methanol

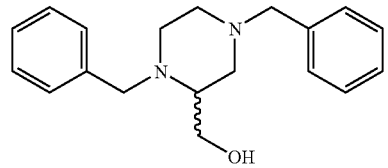

Lithium aluminium hydride (1M in THF) (4 mL, 3.93 mmol) was added to a stirred solution of 1,4-dibenzylpiperazine-2-carboxylic acid ethyl ester (1.33 g, 3.93 mmol) in THF (25 mL) cooled to −78° C. under a nitrogen atmosphere. Water (145 µL), NaOH (aq.) (10 wt %, 145 µL) and water (450 µL) was added at 45 min intervals. The reaction mixture was filtered through a pad of celite and solvent evaporated under reduced pressure to afford (1,4-dibenzylpiperazin-2-yl)methanol (1.16 g, 3.93 mmol, 100%) as a pale yellow oil. Data for (1,4-dibenzylpiperazin-2-yl)methanol: MS (ESI) m/z: 298 ([M+H]$^+$).

c) 1,4-Dibenzyl-2-fluoromethylpiperazine

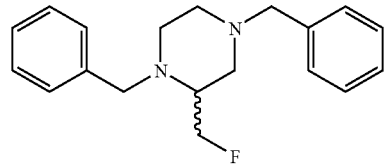

(1,4-Dibenzylpiperazin-2-yl)methanol (15 g, 50.5 mmol) in DCM (50 mL) was added dropwise to a stirred solution of DAST (7.42 mL, 60.6 mmol) in DCM (150 mL) cooled to −78° C. The reaction mixture was maintained below −30° C. for 24 h before warming to room temperature and stirring for an additional 20 h. The reaction was quenched by the addition of water (100 mL). The organic phase was separated, the aqueous basified with NaOH (aq.) to pH 10 and extracted with DCM (3×75 mL). The combined organics were washed with water (2×100 mL), brine (2×100 mL), dried (Na₂SO₄) and concentrated under reduced pressure. The resultant oil was purified by chromatography on silica gel with EtOAc: heptane (1:9, v/v) as eluent to afford 1,4-dibenzyl-2-fluoromethylpiperazine (6.0 g, 20.1 mmol, 40%). A biproduct of the reaction was also isolated, 1,4-dibenzyl-6-fluoroperhydro-1,4-diazepine (1.0 g, 3.35 mmol, 7%).

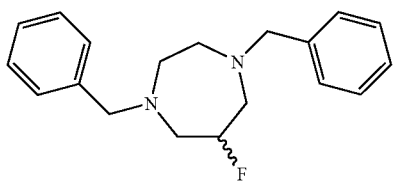

d) 2-Fluoromethylpiperazine

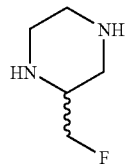

Palladium on charcoal (10 wt %) (400 mg) as a slurry in MeOH was added to a solution of 1,4-dibenzyl-2-fluoromethylpiperazine (400 mg, 1.34 mmol) in MeOH (20 mL). This was subjected to H₂(g) at 5 bar pressure for 18 h. The reaction mixture was filtered through celite and solvent evaporated under reduced pressure. This afforded 2-fluoromethylpiperazine (INTERMEDIATE XII.1) (136 mg, 1.14 mmol, 86%) as a pale yellow oil.

INTERMEDIATE XII.2:
6-Fluoroperhydro-1,4-diazepine

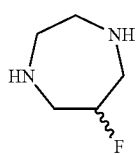

Prepared in a similar manner from 1,4-dibenzyl-6-fluoroperhydro-1,4-diazepine (isolated as a side product in the synthesis of INTERMEDIATE X11.1).

SYNTHESIS OF EXAMPLES ACCORDING TO THE INVENTION

Example 1a

N-tert-Butyl-2-[2-(3-chlorophenyl)-4-oxo-6-perhydro-1,4-diazepin-1-yl-4H-quinazolin-3-yl]acetamide

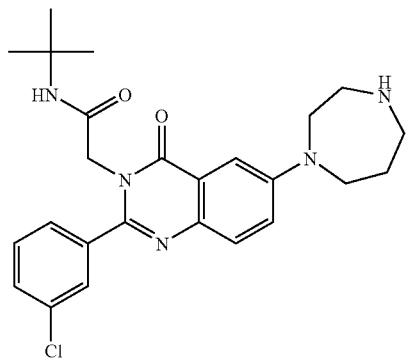

4-[3-(tert-Butylcarbamoylmethyl)-2-(3-chlorophenyl)-4-oxo-3,4-dihydroquinazolin-6-yl]perhydro-1,4-diazepine-1-carboxylic acid tert-butyl ester (INTERMEDIATE VIII.1) (38.9 mg, 0.068 mmol) was treated with TFA:DCM (1:1 (v/v), 1 mL) and the solution stirred at room temperature for 40 min. The volatiles were removed in vacuo and the residue partitioned between DCM and 1 M NaOH (aq.). The organics were dried (Na₂SO₄) and concentrated in vacuo to yield N-tert-butyl-2-[2-(3-chlorophenyl)-4-oxo-6-perhydro-1,4-diazepin-1-yl-4H-quinazolin-3-yl]acetamide (EXAMPLE 1a) (27 mg, 0.046 mmol, 68%) as the trifluoroacetic acid salt.

Data for N-tert-butyl-2-[2-(3-chlorophenyl)-4-oxo-6-perhydro-1,4-diazepin-1-yl-4H-quinazolin-3-yl]acetamide (EXAMPLE 1a)) trifluoroacetic acid salt: ¹H NMR (300 MHz, CDCl₃): δ 7.6-7.4 (m, 6H), 7.21 (dd, 1H), 5.65 (s, 1H), 4.44 (s, 2H), 3.7-3.6 (m, 4H), 3.09 (t, 2H), 2.85 (t, 2H), 2.47 (br s, 1H), 1.98 (m, 2H), 1.34 (s, 9H) ppm; MS (ESI) m/z: 468/470 ([M+H]⁺).

The following compounds were prepared in a similar manner from INTERMEDIATES VII or VIII:

Example 1b

2-[2-(3-Chlorophenyl)-4-oxo-6-perhydro-1,4-diazepin-1-yl-4H-quinazolin-3-yl]-N-isopropylacetamide

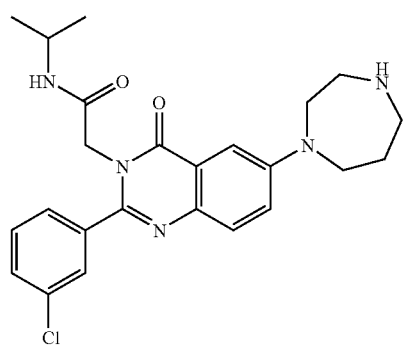

MS (ESI) m/z: 454/456 ([M+H]⁺) (from INTERMEDIATE VII.2)

Example 1c

N-tert-Butyl-2-(2-(3-chloro-4-fluorophenyl)-6-(1,4-diazepan-1-yl)-4-oxoquinazolin-3(4H)-yl)acetamide

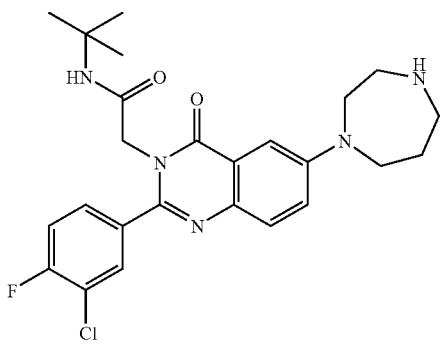

MS (ESI) m/z: 486/488 ([M+H]⁺) (from INTERMEDIATE VII.4)

Example 1d 2-(6-(1,4-Diazepan-1-yl)-2-(4-fluoro-3-methoxyphenyl)-4-oxoquinazolin-3(4H)-yl)-N-tert-butylacetamide

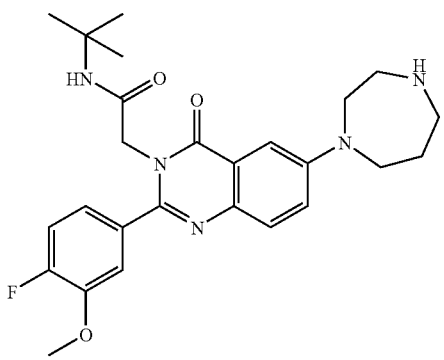

MS (ESI) m/z: 482 ([M+H]⁺) (from INTERMEDIATE VII.5)

Example 1e 2-(2-(3-Chloro-4-fluorophenyl)-6-(1,4-diazepan-1-yl)-4-oxoquinazolin-3(4H)-yl)-N-isopropylacetamide

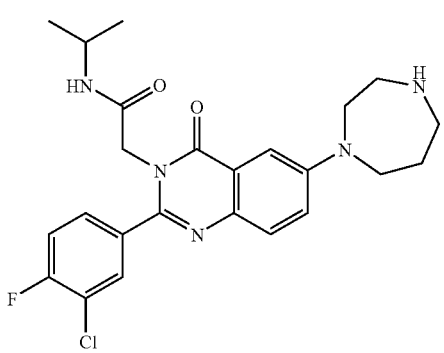

MS (ESI) m/z: 472 ([M+H]⁺) (from INTERMEDIATE VII.6)

Example 1f (S)-2-(2-(3-Chloro-4-fluorophenyl)-6-(3-isopropylpiperazin-1-yl)-4-oxoquinazolin-3(4H)-yl)-N-isopropylacetamide

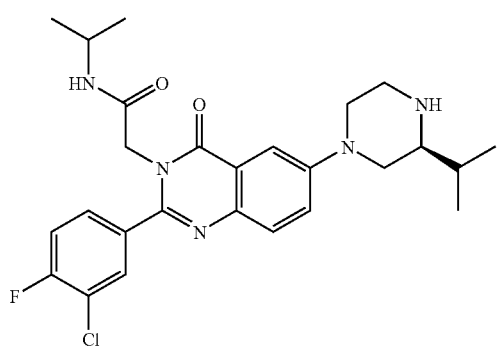

MS (ESI) m/z: 500/502 ([M+H]⁺) (from INTERMEDIATE VII.19)

Example 1g 2-(2-(3-Chloro-4-fluorophenyl)-4-oxo-6-(piperazin-1-yl)quinazolin-3(4H)-yl)-N-isopropylacetamide

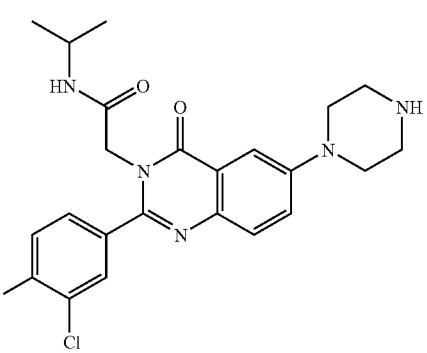

MS (ESI) m/z: 458/460 ([M+H]⁺) (from INTERMEDIATE VII.28)

Example 1h 2-(2-(3-Chloro-4-fluorophenyl)-6-(3-methyl-1,4-diazepan-1-yl)-4-oxoquinazolin-3(4H)-yl)-N-isopropylacetamide

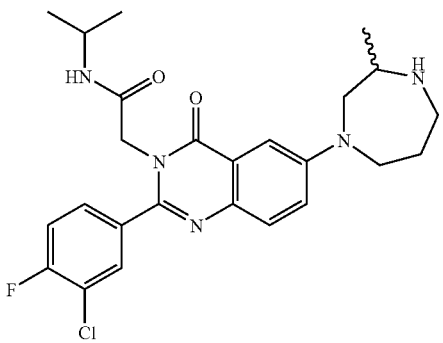

MS (ESI) m/z: 486 ([M+H]⁺) (from INTERMEDIATE VII.18)

Example 1i 2-(6-(1,4-Diazepan-1-yl)-2-(4-fluoro-3-methoxyphenyl)-4-oxoquinazolin-3(4H)-yl)-N-isopropylacetamide

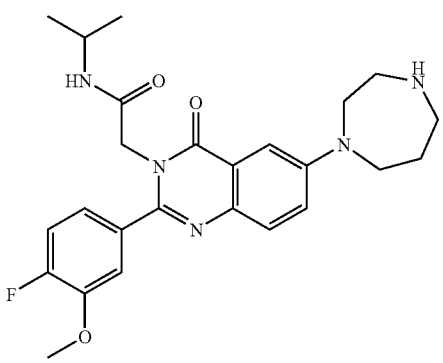

MS (ESI) m/z: 468 ([M+H]⁺) (from INTERMEDIATE VII.7)

Example 1j

2-[2-(3-Chloro-4-fluorophenyl)-6-(6-fluoroperhydro-1,4-diazepin-1-yl)-4-oxo-4H-quinazolin-3-yl]-N-isopropylacetamide

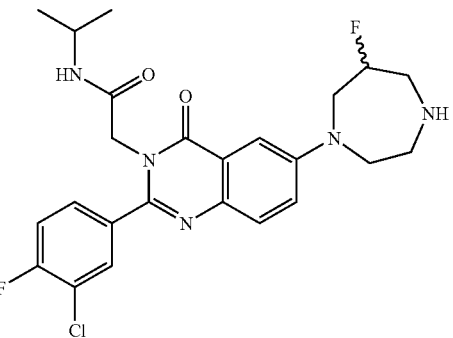

MS (ESI) m/z: 490/492 ([M+H]⁺) (from INTERMEDIATE VII.27).

Example 1k

2-[2-(3-Chloro-4-fluorophenyl)-6-(dimethylperhydro-1,4-diazepin-1-yl)-4-oxo-4H-quinazolin-3-yl]-N-isopropylacetamide

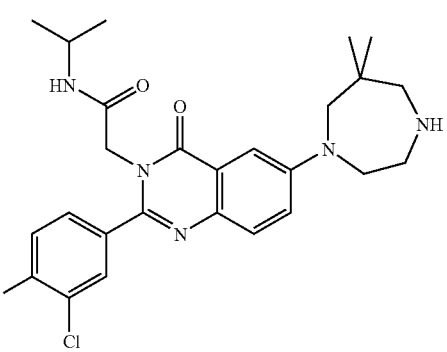

MS (ESI) m/z: 500/502 ([M+H]⁺) (from INTERMEDIATE VII.11).

Example 1l

2-[6-(Dimethylperhydro-1,4-diazepin-1-yl)-2-(4-fluoro-3-methoxyphenyl)-4-oxo-4H-quinazolin-3-yl]-N-isopropylacetamide

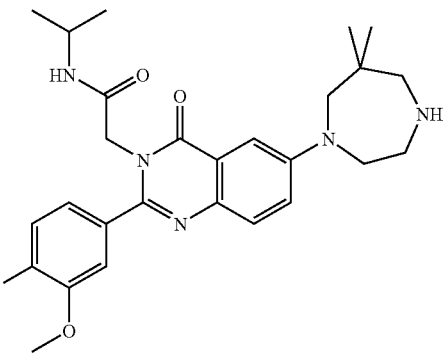

MS (ESI) m/z: 596 ([M+H]⁺) (from INTERMEDIATE VII.10).

Example 2a

N-Isopropyl-2-[2-(3-methoxyphenyl)-4-oxo-6-perhydro-1,4-diazepin-1-yl-4H-quinazolin-3-yl]acetamide

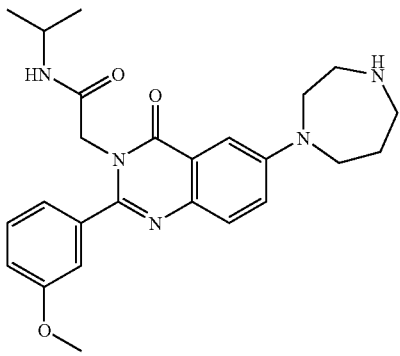

4-[3-(Isopropylcarbamoylmethyl)-2-(3-methoxyphenyl)-4-oxo-3,4-dihydroquinazolin-6-yl]perhydro-1,4-diazepine-1-carboxylic acid tert-butyl ester (INTERMEDIATE VII.1) (50 mg, 0.091 mmol) was treated with 4 N HCl/MeOH (10 mL) and the resulting solution was stirred at room temperature for 2 h. The reaction mixture was concentrated in vacuo to afford N-isopropyl-2-[2-(3-methoxyphenyl)-4-oxo-6-perhydro-1,4-diazepin-1-yl-4H-quinazolin-3-yl]acetamide (EXAMPLE 2a) (40 mg, 0.091 mmol, 100%) as the hydrochloride salt. Data for N-isopropyl-2-[2-(3-methoxyphenyl)-4-oxo-6-perhydro-1,4-diazepin-1-yl-4H-quinazolin-3-yl]acetamide (EXAMPLE 2a) (EXAMPLE 2a) hydrochloride salt: MS (ESI) m/z: 450 ([M+H]$^+$)

The following compounds were prepared in a similar manner from INTERMEDIATES VII:

Example 2b

N-Isopropyl-2-[2-(3-methoxyphenyl)-4-oxo-6-piperazin-1-yl-4H-quinazolin-3-yl]acetamide

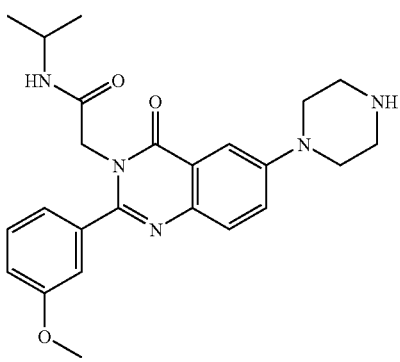

MS (ESI) m/z: 436 ([M+H]$^+$) (from INTERMEDIATE VII.3)

Example 3a

N-Isopropyl-2-[2-(3-methoxyphenyl)-6-(4-methylperhydro-1,4-diazepin-1-yl)-4-oxo-4H-quinazolin-3-yl]acetamide

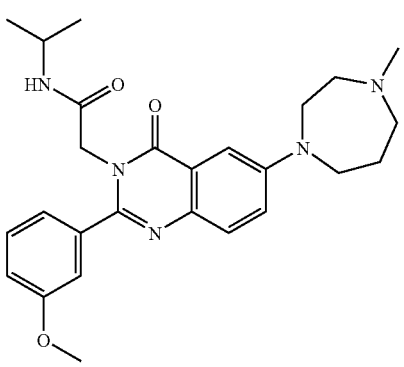

To a solution of 2-amino-N-(isopropylcarbamoylmethyl)-5-(4-methylperhydro-1,4-diazepin-1-yl)benzamide (INTERMEDIATE V.1) (1.4 g, 4.1 mmol) in absolute ethanol (70 mL) was added ethyl 3-methoxybenzimidate hydrochloride (INTERMEDIATE II.2) (1.8 g, 8.3 mmol). The resultant mixture was heated to at reflux temperature for 20 h. The reaction mixture was concentrated in vacuo, the dark residue dissolved up in DCM (70 mL) and washed with 1 N HCl (aq.) (3×20 mL). The aqueous phase was washed with EtOAc (20 mL), basified to pH≈10-11 with 4 N NaOH (aq.) and the resultant pale green precipitate was collected by suction filtration. The crude product was purified by chromatography on silica gel with a gradient of MeOH:DCM (1:19 to 3:7, v/v) as eluent to afford the product as an off-white solid (0.60 g, 1.3 mmol, 32%). Recrystallization from EtOAc:DCM afforded pure N-isopropyl-2-[2-(3-methoxyphenyl)-6-(4-methylperhydro-1,4-diazepin-1-yl)-4-oxo-4H-quinazolin-3-yl]acetamide (EXAMPLE 3a) (0.35 g, 0.76 mmol, 18%) as a white solid.

Data for N-isopropyl-2-[2-(3-methoxyphenyl)-6-(4-methylperhydro-1,4-diazepin-1-yl)-4-oxo-4H-quinazolin-3-yl]acetamide (EXAMPLE 3a): $^1$H NMR (300 MHz, CDCl$_3$): δ 7.64 (d, 1H), 7.3-7.4 (m, 2H), 7.16-7.23 (m, 3H), 7.0 (dd, 1H), 5.71 (br d, 1H, amide N—H), 4.49 (s, 2H), 4.08 (m, 1H), 3.82 (s, 3H), 3.68 (dd, 2H), 3.61 (t, 2H), 2.76 (m, 2H), 2.57 (m, 2H), 2.39 (s, 3H), 2.06 (m, 2H), 1.15 (d, 6H) ppm; MS (ESI) m/z: 46 ([M+H]$^+$), 949 ([M+Na]$^+$); M.p. 204° C. (decomp.).

The following compounds were prepared in a similar manner from INTERMEDIATES V and II:

Example 3b

2-[6-(3-Dimethylamino-pyrrolidin-1-yl)-2-(3-methoxyphenyl)-4-oxo-4H-quinazolin-3-yl]-N-isopropylacetamide

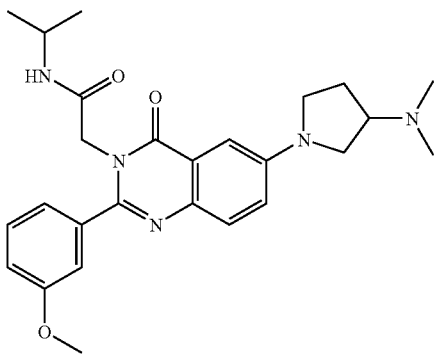

MS (ESI) m/z: 464 ([M+H]⁺) (from INTERMEDIATE V.4 and INTERMEDIATE II.2)

Example 3c

2-[6-(3-Dimethylaminomethyl-piperidin-1-yl)-2-(3-methoxyphenyl)-4-oxo-4H-quinazolin-3-yl]-N-isopropylacetamide

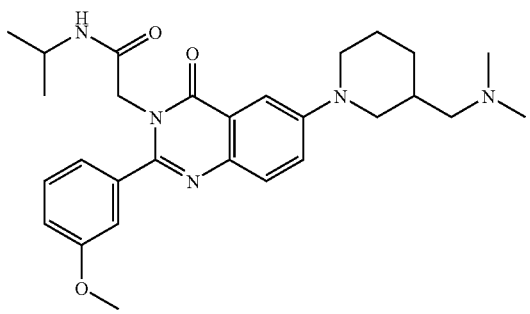

MS (ESI) m/z: 492 ([M+H]⁺) (from INTERMEDIATE V.5 and INTERMEDIATE II.2)

Example 3d

N-Isopropyl-2-[2-(3-methoxyphenyl)-6-(4-methylpiperazin-1-v)-4-oxo-4H-quinazolin-3-yl]acetamide

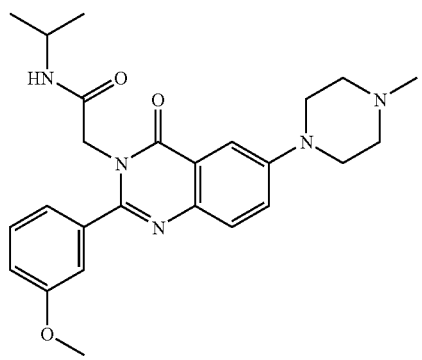

MS (ESI) m/z: 450 ([M+H]⁺) (from INTERMEDIATE V.6 and INTERMEDIATE II.2)

Example 3e

N-Isopropyl-2-[2-(3-methoxyphenyl)-4-oxo-6-((S)-3-piperidin-1-ylmethylpiperidin-1-yl)-4H-quinazolin-3-yl]

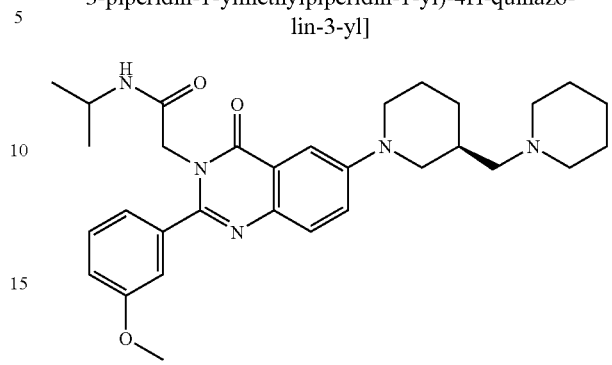

MS (ESI) m/z: 532 ([M+H]⁺) (from INTERMEDIATE V.7 and INTERMEDIATE II.2)

Example 3f

N-Isopropyl-2-[2-(3-methoxyphenyl)-4-oxo-6-((R)-3-piperidin-1-ylmethylpiperidin-1-yl)-4H-quinazolin-3-yl]acetamide

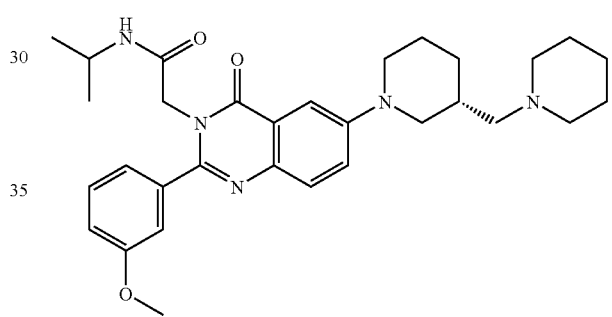

MS (ESI) m/z: 532 ([M+H]⁺) (from INTERMEDIATE V.9 and INTERMEDIATE II.2)

Example 3g

N-Isopropyl-2-[2-(3-methoxyphenyl)-4-oxo-6-(3-piperidin-1-ylmethylpiperidin-1-yl)-4H-quinazolin-3-yl]acetamide

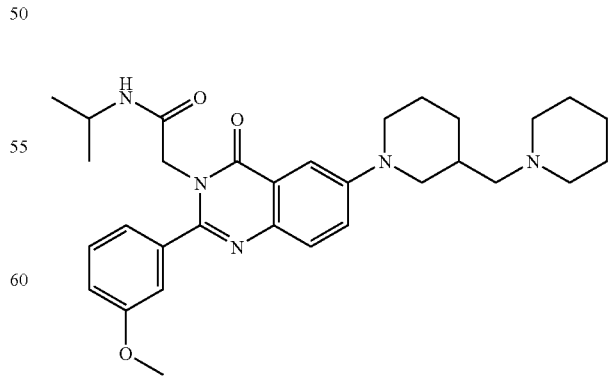

MS (ESI) m/z: 532 ([M+H]⁺) (from INTERMEDIATE V.10 and INTERMEDIATE II.2)

Example 3h

N-Isopropyl-2-[2-(3-methoxyphenyl)-4-oxo-6-(4-phenylperhydro-1,4-diazepin-1-yl)-4H-quinazolin-3-yl]acetamide

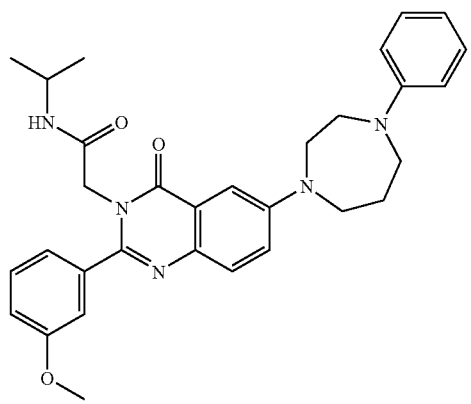

MS (ESI) m/z: 526 ([M+H]⁺) (from INTERMEDIATE V.12 and INTERMEDIATE II.2)

Example 3i

N-tert-Butyl-2-[2-(3-chlorophenyl)-6-(4-methylperhydro-1,4-diazepin-1-yl)-4-oxo-4H-quinazolin-3-yl]acetamide

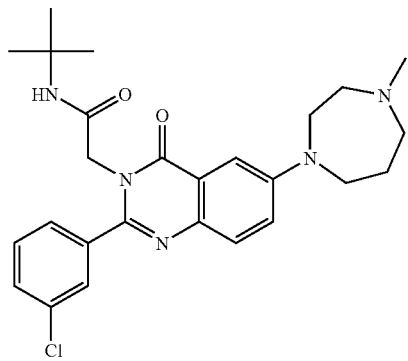

MS (ESI) m/z: 482/484 ([M+H]⁺) (from INTERMEDIATE V.13 and INTERMEDIATE II.1)

Example 3j

2-[2-(3-Chlorophenyl)-6-(4-methylperhydro-1,4-diazepin-1-yl)-4-oxo-4H-quinazolin-3-yl]-N-isopropylacetamide

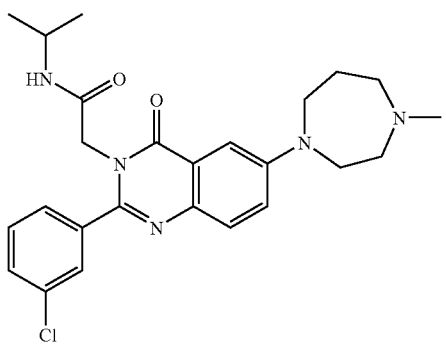

MS (ESI) m/z: 468/470 ([M+H]⁺) (from INTERMEDIATE V.1 and INTERMEDIATE II.1)

Example 3k

2-[6-[1,4']Bipiperidinyl-1'-yl-2-(3-methoxyphenyl)-4-oxo-4H-quinazolin-3-yl]-N-isopropylacetamide

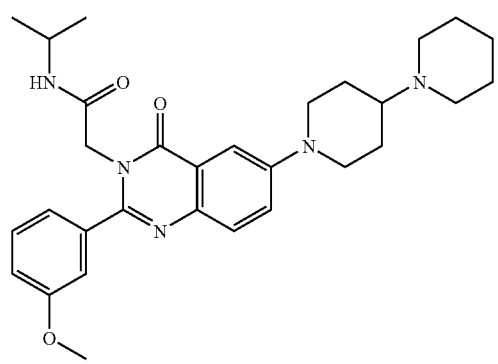

MS (ESI) m/z: 518 ([M+H]⁺) (from INTERMEDIATE V.15 and INTERMEDIATE II.2)

Example 3l

N-Isopropyl-2-[2-(3-methoxyphenyl)-4-oxo-6-[3-(2-piperidin-1-ylethyl)azetidin-1-yl]-4H-quinazolin-3-yl]acetamide

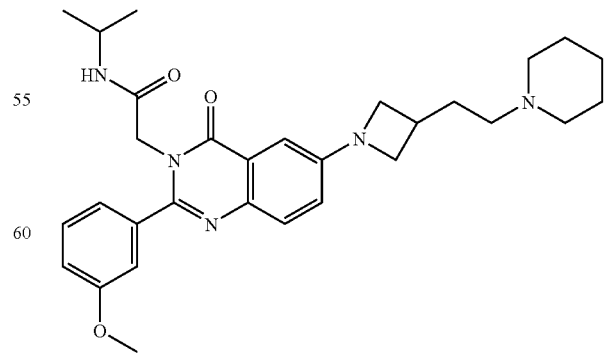

MS (ESI) m/z: 518 ([M+H]⁺) (from INTERMEDIATE V.16 and INTERMEDIATE II.2)

Example 3m

N-Isopropyl-2-[2-(3-methoxyphenyl)-6-(3-morpholin-4-ylmethylpiperidin-1-yl)-4-oxo-4H-quinazolin-3-yl]acetamide

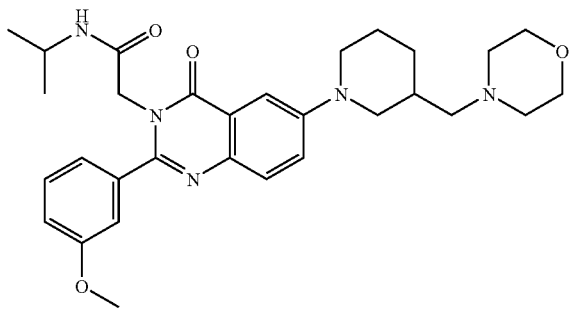

MS (ESI) m/z: 534 ([M+H]$^+$) (from INTERMEDIATE V.17 and INTERMEDIATE II.2)

Example 3n

N-Isopropyl-2-[2-(3-methoxyphenyl)-4-oxo-6-(3-piperidin-1-ylmethylpyrrolidin-1-yl)-4H-quinazolin-3-yl]acetamide

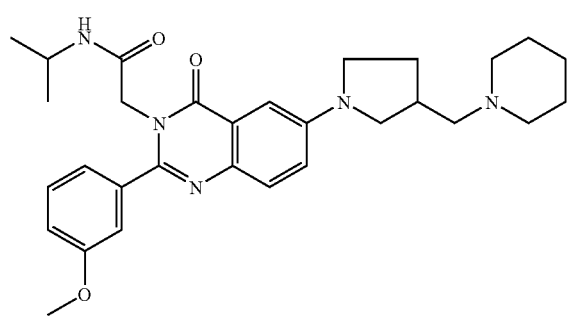

MS (ESI) m/z: 518 ([M+H]$^+$) (from INTERMEDIATE V.14 and INTERMEDIATE II.2)

Example 3o

N-Isopropyl-2-[2-(3-methoxyphenyl)-4-oxo-6-(3-piperidin-1-ylmethylazetidin-1-yl)-4H-quinazolin-3-yl]acetamide

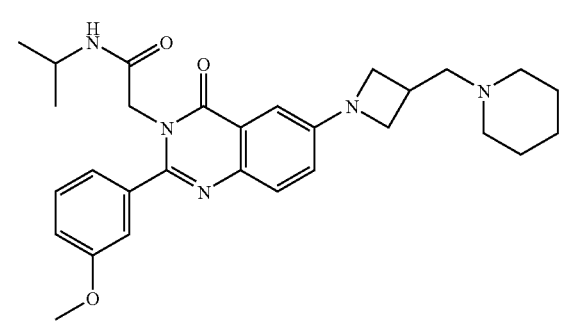

MS (ESI) m/z: 504 ([M+H]$^+$) (from INTERMEDIATE V.11 and INTERMEDIATE II.2)

Example 3p

2-[6-(4-dimethylaminopiperidin-1-yl)-2-(3-methoxyphenyl)-4-oxo-4H-quinazolin-3-yl]-N-isopropylacetamide

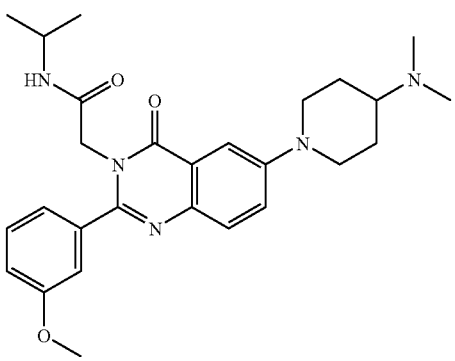

MS (ESI) m/z: 478 ([M+H]$^+$) (from INTERMEDIATE V.8 and INTERMEDIATE II.2)

Example 3q

2-[2-(4-Fluoro-3-methoxyphenyl)-6-((S)-3-methylpiperazin-1-yl)-4-oxo-4H-quinazoline-3-yl]-N-isopropylacetamide

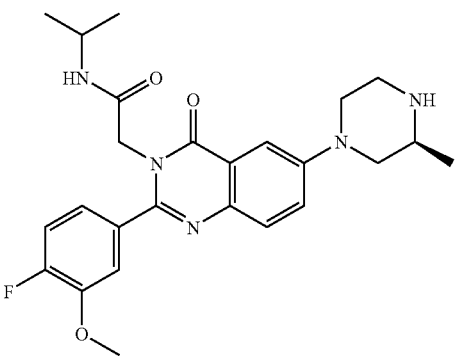

MS (ESI) m/z: 468 ([M+H]$^+$) (from INTERMEDIATE V.18 and INTERMEDIATE II.3)

Example 3r

2-[6-(Dimethylpiperazin-1-yl)-2-(4-fluoro-3-methoxyphenyl)-4-oxo-4H-quinazolin-3-yl]-N-isopropylacetamide

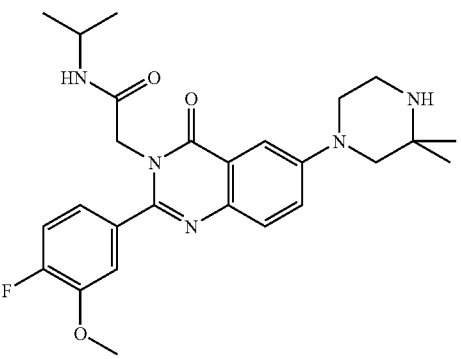

MS (ESI) m/z: 482 ([M+H]$^+$) (from INTERMEDIATE V.19 and INTERMEDIATE II.3)

Example 3s 2-(6-(2,5-Dimethylpiperazin-1-yl)-2-(4-fluoro-3-methoxyphenyl)-4-oxo-4H-quinazolin-3-yl)-N-isopropylacetamide

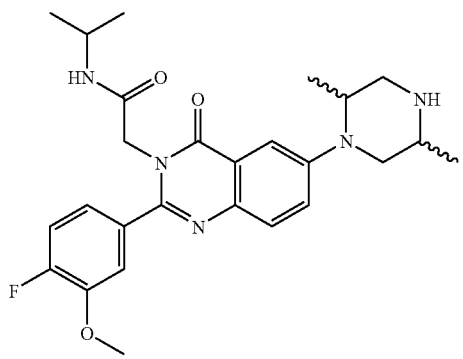

MS (ESI) m/z: 482 ([M+H]$^+$) (from INTERMEDIATE V.20 and INTERMEDIATE II.3)

Example 3t

2-[2-(4-Fluoro-3-methoxyphenyl)-6-(octahydropyrido[1,2-a]pyrazin-2-yl)-4-oxo-4H-quinazolin-3-yl]-N-isopropylacetamide

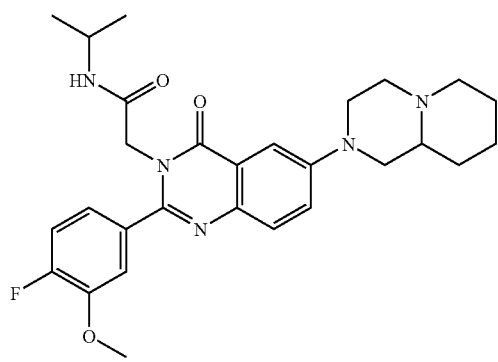

MS (ESI) m/z: 508 ([M+H]$^+$) (from INTERMEDIATE V.46 and INTERMEDIATE II.3)

Example 3u

2-[2-(3-Chloro-4-fluorophenyl)-6-(dimethylpiperazin-1-yl)-4-oxo-4H-quinazolin-3-yl]-N-isopropylacetamide

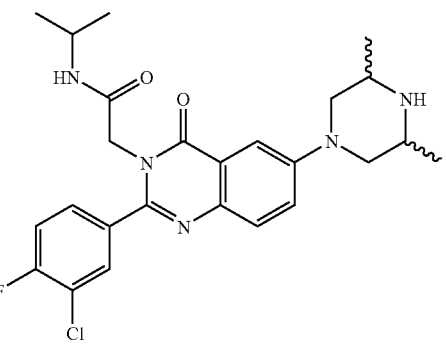

MS (ESI) m/z: 486/488 ([M+H]$^+$) (from INTERMEDIATE V.24 and INTERMEDIATE II.4).

Example 3v

2-[2-(3-Chloro-4-fluorophenyl)-6-(1,4-diazabicyclo[3.2.2]non-4-yl)-4-oxo-4H-quinazolin-3-yl]-N-isopropylacetamide

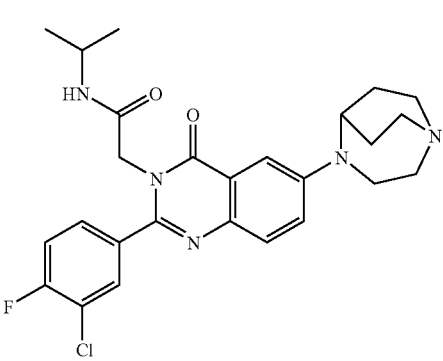

MS (ESI) m/z: 498/500 ([M+H]$^+$) (from INTERMEDIATE V.47 and INTERMEDIATE II.4).

Example 3w

2-[2-(3-Chloro-4-fluorophenyl)-6-[4-(2-hydroxyethyl)perhydro-1,4-diazepin-1-yl]-4-oxo-4H-quinazolin-3-yl]-N-isopropylacetamide

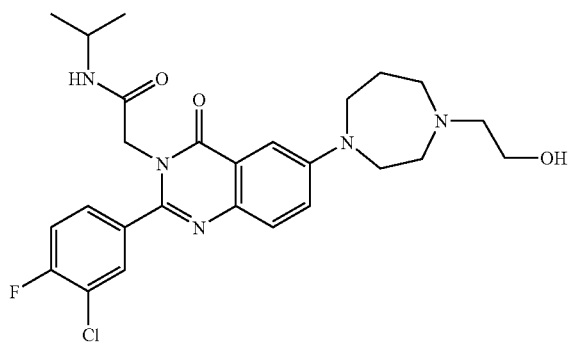

MS (ESI) m/z: 516 ([M+H]⁺) from INTERMEDIATE V.22 and INTERMEDIATE II.4).

Example 3x

2-[2-(3-Chloro-4-fluorophenyl)-6-((R)-3-methylpiperazin-1-yl)-4-oxo-4H-quinazolin-3-yl]-N-isopropylacetamide

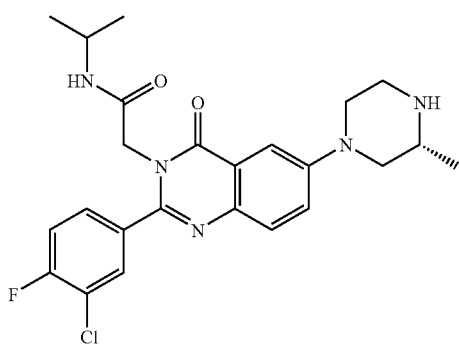

MS (ESI) m/z: 472/474 ([M+H]⁺) from INTERMEDIATE V.25 and INTERMEDIATE II.4)

Example 3y

2-[2-(3-Chloro-4-fluorophenyl)-6-(4-isopropylpiperazin-1-yl)-4-oxo-4H-quinazolin-3-yl]-N-isopropylacetamide

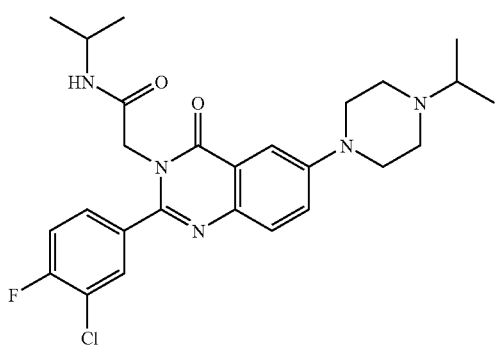

MS (ESI) m/z: 500 ([M+H]⁺) from INTERMEDIATE V.23 and INTERMEDIATE II.4).

Example 3z

2-[2-(4-Fluoro-3-methoxyphenyl)-6-(4-isopropylpiperazin-1-yl)-4-oxo-4H-quinazolin-3-yl]-N-isopropylacetamide

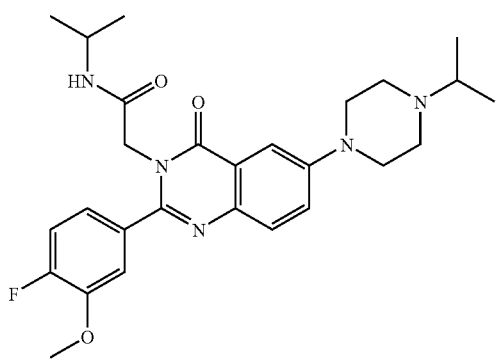

MS (ESI) m/z: 497 ([M+H]⁺) (from INTERMEDIATE V.23 and INTERMEDIATE II.3).

Example 4a

2-[6-(4-Ethylperhydro-1,4-diazepin-1-yl)-2-(3-methoxyphenyl)-4-oxo-4H-quinazolin-3-yl]-N-isopropylacetamide

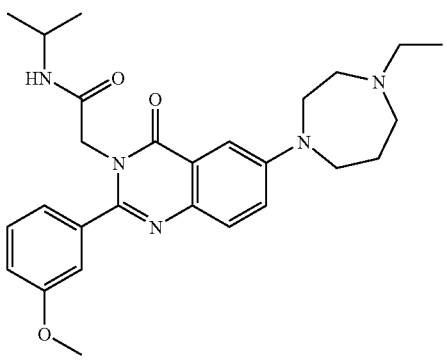

A mixture of N-isopropyl-2-[2-(3-methoxyphenyl)-4-oxo-6-perhydro-1,4-diazepin-1-yl-4H-quinazolin-3-yl]acetamide (EXAMPLE 2a) hydrochloride salt (50 mg, 0.103 mmol), ethyl bromide (22 mg, 0.21 mmol), and $K_2CO_3$ (43 mg, 0.31 mmol) in acetonitrile (5 mL) was heated to reflux for 24 h. The mixture was then cooled, filtered and concentrated in vacuo. The crude residue was purified by preparative HPLC to afford 2-[6-(4-ethylperhydro-1,4-diazepin-1-yl)-2-(3-methoxyphenyl)-4-oxo-4H-quinazolin-3-yl]-N-isopropylacetamide (EXAMPLE 4a) (5.1 mg, 0.010 mmol, 10%) as the hydrochloride salt.

Data for 2-[6-(4-ethylperhydro-1,4-diazepin-1-yl)-2-(3-methoxyphenyl)-4-oxo-4H-quinazolin-3-yl]-N-isopropylacetamide (EXAMPLE 4a) hydrochloride salt: MS (ESI) m/z: 478 ([M+H]⁺), 955 ([2M+H]⁺), 977 ([2M+Na]⁺).

The following compounds were prepared in a similar manner from EXAMPLES 1 or 2:

Example 4b

N-Isopropyl-2-[6-(4-isopropylperhydro-1,4-diazepin-1-yl)-2-(3-methoxyphenyl)-4-oxo-4H-quinazolin-3-yl]acetamide

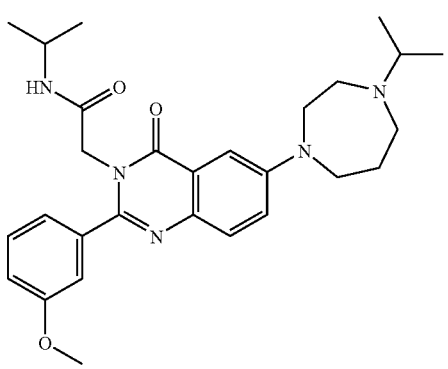

MS (ESI) m/z: 492 ([M+H]$^+$) (from EXAMPLE 2a)

Example 4c

N-Isopropyl-2-{2-(3-methoxyphenyl)-4-oxo-6-[4-(2,2,2-trifluoroethyl)Perhydro-1,4-diazepin-1-yl]-4H-quinazolin-3-yl}acetamide

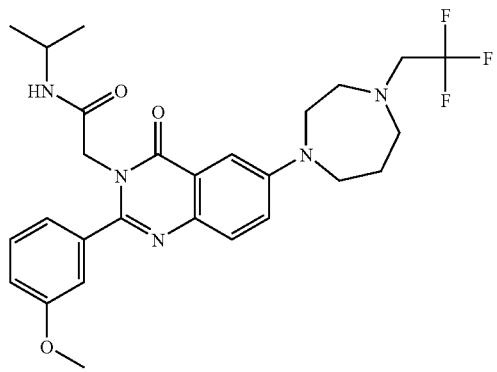

MS (ESI) m/z: 532 ([M+H]$^+$) (from EXAMPLE 2a)

Example 4d

N-Isopropyl-2-[6-[4-(2-methoxyethyl)perhydro-1,4-diazepin-1-yl]-2-(3-methoxyphenyl)-4-oxo-4H-quinazolin-3-yl]acetamide

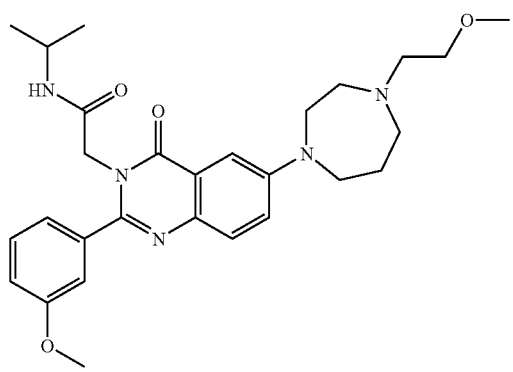

MS (ESI) m/z: 508 ([M+H]$^+$) (from EXAMPLE 2a)

Example 4e

2-[6-(4-Benzylperhydro-1,4-diazepin-1-yl)-2-(3-methoxyphenyl)-4-oxo-4H-quinazolin-3-yl]-N-isopropylacetamide

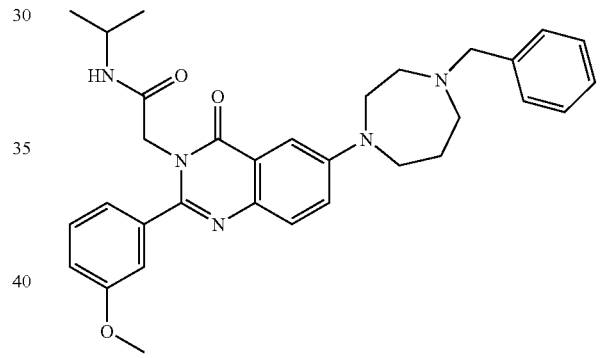

MS (ESI) m/z: 540 ([M+H]$^+$) (from EXAMPLE 2a)

Example 4f

2-[6-(4-Cyanomethylperhydro-1,4-diazepin-1-yl)-2-(3-methoxyphenyl)-4-oxo-4H-quinazolin-3-yl]-N-isopropylacetamide

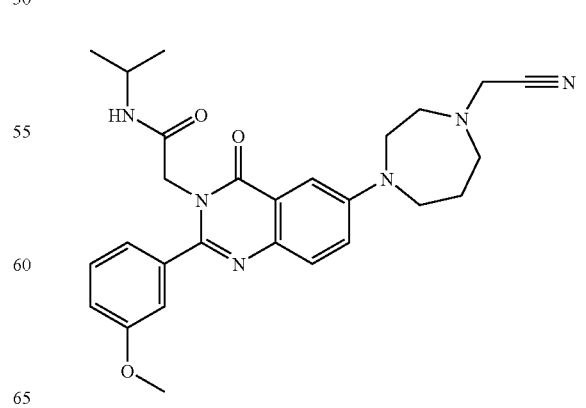

MS (ESI) m/z: 489 ([M+H]$^+$) (from EXAMPLE 2a)

Example 4g

2-[2-(3-Chlorophenyl)-6-(4-cyclopropylmethylperhydro-1,4-diazepin-1-yl)-4-oxo-4H-quinazolin-3-yl]-N-isopropylacetamide

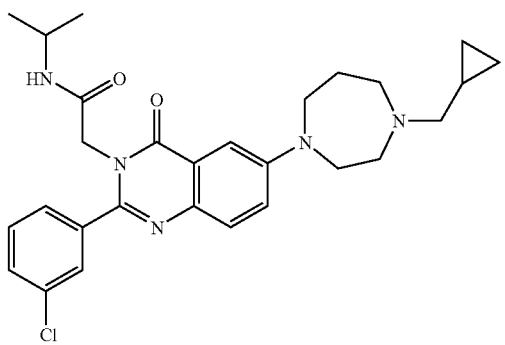

MS (ESI) m/z: 508/5010 ([M+H]+) (from EXAMPLE 1b)

Example 4h

2-[6-(4-Cyclopropylmethylperhydro-1,4-diazepin-1-yl)-2-(3-methoxyphenyl)-4-oxo-4H-quinazolin-3-yl]-N-isopropylacetamide

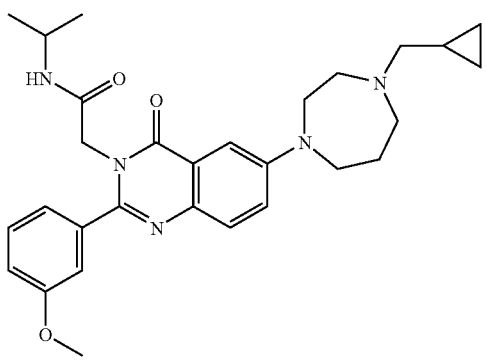

MS (ESI) m/z: 504 ([M+H]+) (from EXAMPLE 2a)

Example 4i

N-tert-Butyl-2-[2-(3-chloro-4-fluorophenyl)-6-[4-(2-hydroxyethyl)perhydro-1,4-diazepin-1-yl]-4-oxo-4H-quinazolin-3-yl]acetamide

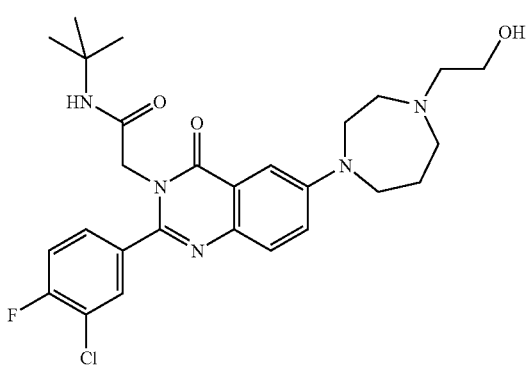

N-tert-Butyl-2-(2-(3-chloro-4-fluorophenyl)-6-(1,4-diazepan-1-yl)-4-oxoquinazolin-3(4H)-yl)acetamide (EXAMPLE 1c) (100 mg, 0.206 mmol), 2-bromoethanol (206 mg, 0.117 ml, 1.646 mmol) and potassium carbonate (57 mg, 0.412 mmol) in DMF (1 mL) was heated in a microwave at 100° C. for 10 min. The reaction mixture was filtered and purified by SCX eluting in MeOH then 2M NH$_3$/MeOH. Solvent was evaporated under reduced pressure and product further purified by HPLC. This afforded N-tert-butyl-2-{2-(3-chloro-4-fluorophenyl)-6-[4-(2-hydroxyethyl)perhydro-1,4-diazepin-1-yl]-4-oxo-4H-quinazolin-3-yl}acetamide (EXAMPLE 4i) (39 mg, 0.074 mmol, 90%) as a white solid.

Data for N-tert-butyl-2-{2-(3-chloro-4-fluorophenyl)-6-[4-(2-hydroxyethyl)perhydro-1,4-diazepin-1-yl]-4-oxo-4H-quinazolin-3-yl}acetamide (EXAMPLE 4i): MS (ESI) m/z: 530/532 ([M+H]+).

Example 4j

N-tert-Butyl-2-[2-(4-fluoro-3-methoxyphenyl)-6-[4-(2-hydroxyethyl)perhydro-1,4-diazepin-1-yl]-4-oxo-4H-quinazolin-3-yl]acetamide

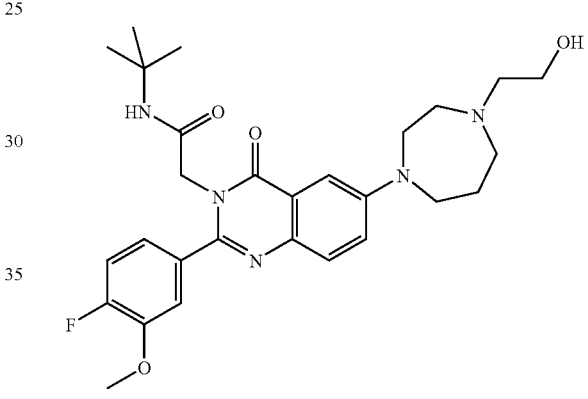

MS (ESI) m/z: 526 ([M+H]+) (from EXAMPLE 1d)

Example 4k

2-{2-(3-Chlorophenyl)-6-[4-(3-methyloxetan-3-ylmethyl)perhydro-1,4-diazepin-1-yl]-4-oxo-4H-quinazolin-3-yl}-N-isopropylacetamide

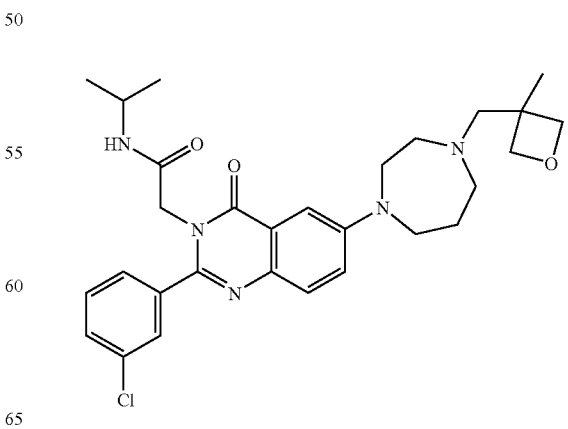

MS (ESI) m/z: 538/540 ([M+H]+) (from EXAMPLE 1b)

Example 4l

2-{2-(3-Chlorophenyl)-6-[4-(2,2-difluorocyclopropylmethyl)perhydro-1,4-diazepin-1-yl]-4-oxo-4H-quinazolin-3-yl}-N-isopropylacetamide

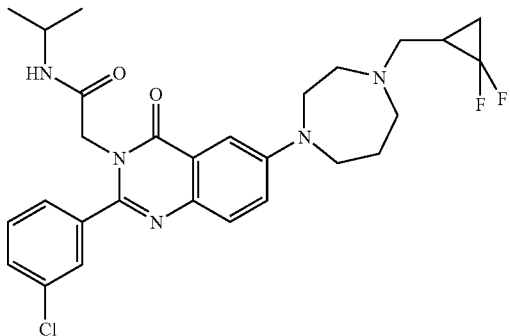

MS (ESI) m/z: 544/546 ([M+H]$^+$) (from EXAMPLE 1b)

Example 4m

2-{2-(4-Fluoro-3-methoxyphenyl)-6-[4-(3-methyloxetan-3-ylmethyl)perhydro-1,4-diazepin-1-yl]-4-oxo-4H-quinazolin-3-yl}-N-isopropylacetamide

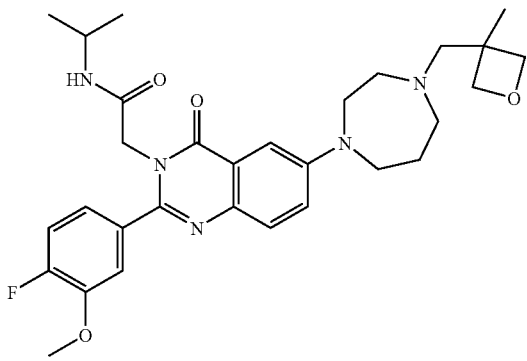

MS (ESI) m/z: 552 ([M+H]$^+$) (from EXAMPLE 1i)

Example 4n

2-[6-[4-(2,2-Difluorocyclopropylmethyl)perhydro-1,4-diazepin-1-yl]-2-(4-fluoro-3-methoxyphenyl)-4-oxo-4H-quinazolin-3-yl]-N-isopropylacetamide

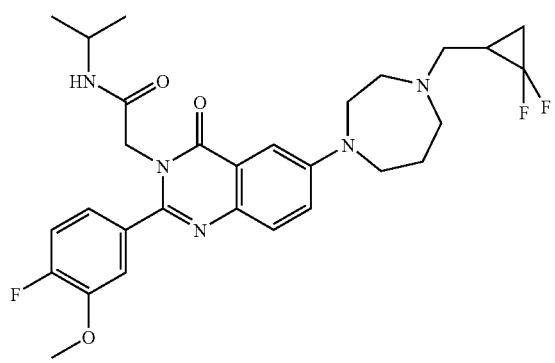

MS (ESI) m/z: 558 ([M+H]$^+$) (from EXAMPLE 1i)

Example 4o

2-{2-(3-Chloro-4-fluorophenyl)-6-[4-(3-methyloxetan-3-ylmethyl)perhydro-1,4-diazepin-1-yl]-4-oxo-4H-quinazolin-3-yl}-N-isopropylacetamide

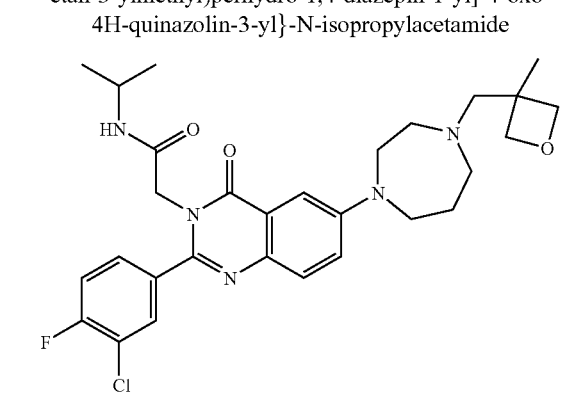

MS (ESI) m/z: 556/558 ([M+H]$^+$) (from EXAMPLE 1e)

Example 4p

2-{2-(3-Chloro-4-fluorophenyl)-6-[4-(2,2-difluorocyclopropylmethyl)perhydro-1,4-diazepin-1-yl]-4-oxo-4H-quinazolin-3-yl}-N-isopropylacetamide

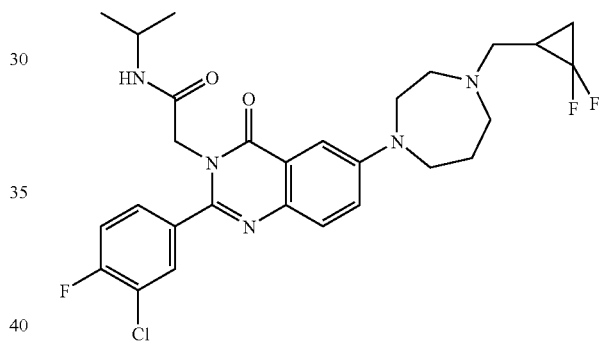

MS (ESI) m/z: 562/564 ([M+H]$^+$) (from EXAMPLE 1e)

Example 4q

2-{2-(4-Fluoro-3-methoxyphenyl)-6-[4-(2-hydroxyethyl)perhydro-1,4-diazepin-1-yl]-4-oxo-4H-quinazolin-3-yl}-N-isopropylacetamide

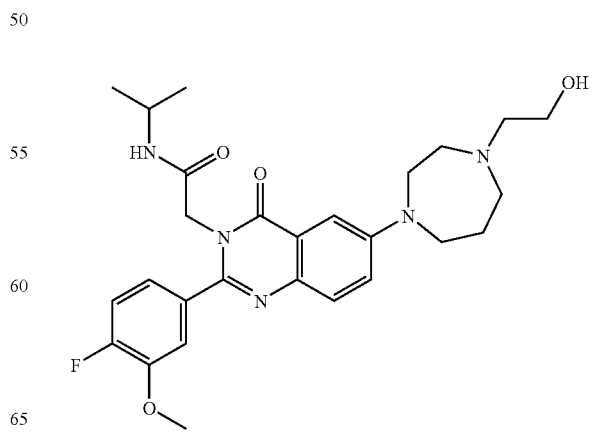

2-(6-(1,4-Diazepan-1-yl)-2-(4-fluoro-3-methoxyphenyl)-4-oxoquinazolin-3(4H)-yl)-N-isopropylacetamide (EXAMPLE 1i) (28 mg, 0.06 mmol), 2-bromoethanol (30 mg, 0.017 mL, 0.24 mmol), potassium carbonate (17 mg, 0.12 mmol) and potassium iodide (1 mg, 5.99 µmol) were combined in a microwave vial and DMF (1 mL) added. The reaction mixture was heated at 100° C. for 5 min in the microwave. LCMS indicated that the desired product was being formed. Additional 2-bromoethanol (30 mg, 0.017 mL, 0.24 mmol) was added and reaction mixture was heated at 100° C. for a further 5 min in the microwave. Product was purified by preparative LCMS to afford 2-{2-(4-fluoro-3-methoxyphenyl)-6-[4-(2-hydroxyethyl)perhydro-1,4-diazepin-1-yl]-4-oxo-4H-quinazolin-3-yl}-N-isopropylacetamide (EXAMPLE 4q) (4 mg, 7.82 µmol, 13%).

2-{2-(4-fluoro-3-methoxyphenyl)-6-[4-(2-hydroxyethyl)perhydro-1,4-diazepin-1-yl]-4-oxo-4H-quinazolin-3-yl}-N-isopropylacetamide (EXAMPLE 4q): MS (ESI) m/z: 512 ([M+H]$^+$).

The following compounds were prepared in a similar manner from EXAMPLES 1 or 2:

Example 4r

N-tert-Butyl-2-[2-(3-chloro-4-fluorophenyl)-6-(4-isopropylperhydro-1,4-diazepin-1-yl)-4-oxo-4H-quinazolin-3-yl]acetamide

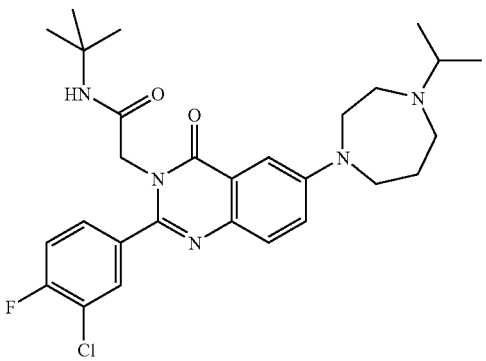

MS (ESI) m/z: 528/530 ([M+H]$^+$) (from EXAMPLE 1c)

Example 4s

N-tert-Butyl-2-[2-(4-fluoro-3-methoxyphenyl)-6-(4-isopropylperhydro-1,4-diazepin-1-yl)-4-oxo-4H-quinazolin-3-yl]acetamide

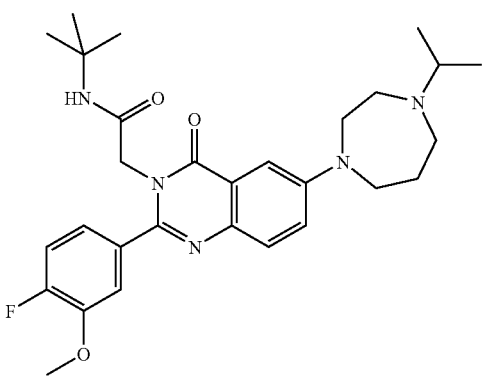

MS (ESI) m/z: 524 ([M+H]$^+$) (from EXAMPLE 1d)

Example 4t

2-{2-(3-Chloro-4-fluorophenyl)-6-[4-(2-methoxyethyl)perhydro-1,4-diazepin-1-yl]-4-oxo-4H-quinazolin-3-yl}-N-isopropylacetamide

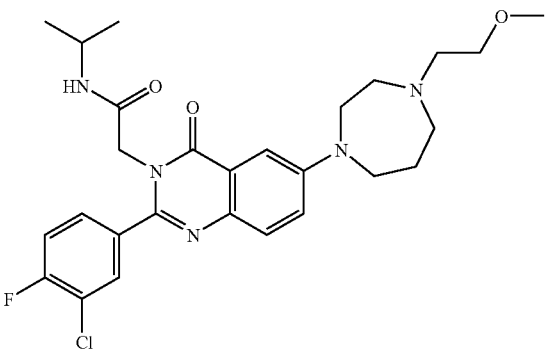

MS (ESI) m/z: 530/532 ([M+H]$^+$) (from EXAMPLE 1e)

Example 4u

2-{2-(3-Chlorophenyl)-6-[4-(2-methoxyethyl)perhydro-1,4-diazepin-1-yl]-4-oxo-4H-quinazolin-3-yl}-N-isopropylacetamide

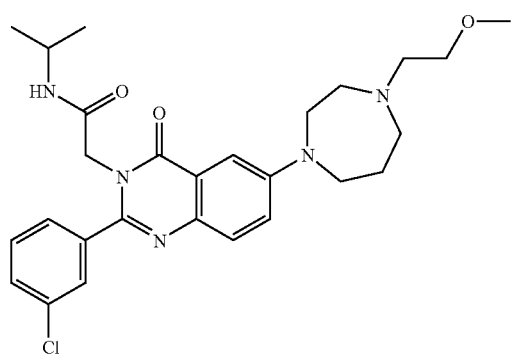

MS (ESI) m/z: 512/514 ([M+H]$^+$) (from EXAMPLE 1b)

Example 4v

2-{2-(4-Fluoro-3-methoxyphenyl)-6-[4-(2-methoxyethyl)perhydro-1,4-diazepin-1-yl]-4-oxo-4H-quinazolin-3-yl}-N-isopropylacetamide

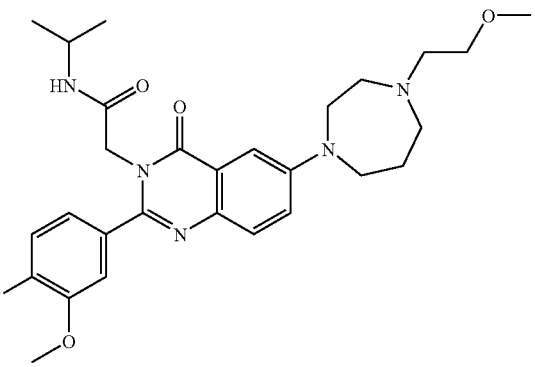

MS (ESI) m/z: 526 ([M+H]$^+$) (from EXAMPLE 1i)

Example 4w

2-{2-(3-Chlorophenyl)-6-[4-(2-hydroxyethyl)perhydro-1,4-diazepin-1-yl]-4-oxo-4H-quinazolin-3-yl}-N-isopropylacetamide

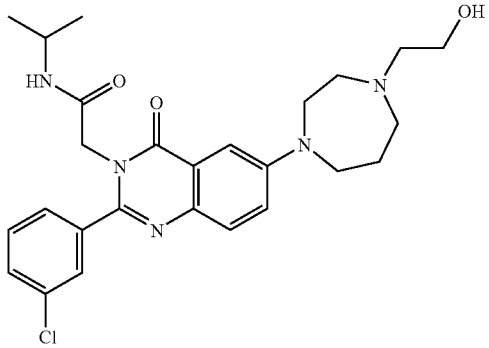

MS (ESI) m/z: 498/500 ([M+H]+) (from EXAMPLE 1b)

Example 4x

2-[2-(4-Fluoro-3-methoxyphenyl)-6-(4-isopropylperhydro-1,4-diazepin-1-yl)-4-oxo-4H-quinazolin-3-yl]-N-isopropylacetamide

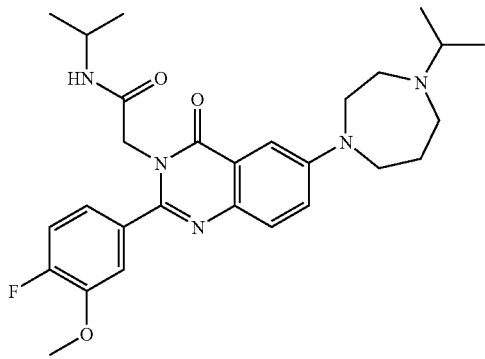

MS (ESI) m/z: 510 ([M+H]+) (from EXAMPLE 1i)

Example 5a

N-tert-Butyl-2-[2-(3-chlorophenyl)-6-(4-isopropylperhydro-1,4-diazepin-1-yl)-4-oxo-4H-quinazolin-3-yl]acetamide

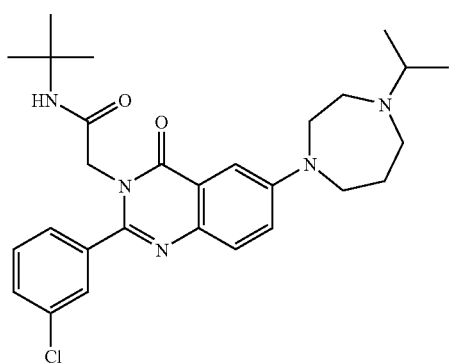

N-tert-Butyl-2-[2-(3-chlorophenyl)-4-oxo-6-perhydro-1,4-diazepin-1-yl-4H-quinazolin-3-yl]acetamide (EXAMPLE 1a) (17 mg, 0.03 mmol), anhydrous acetone (30 μL), sodium cyanoborohydride (3 mg, 0.03 mmol) and glacial acetic acid (12 μL, 0.21 mmol) in anhydrous THF (0.15 mL) was heated in a microwave at 130° C. for 10 minutes. The resulting mixture was purified by preparative TLC on silica gel with DCM:MeOH:NH$_4$OH (40:2:1, v/v) as eluent to give N-tert-butyl-2-[2-(3-chlorophenyl)-6-(4-isopropylperhydro-1,4-diazepin-1-yl)-4-oxo-4H-quinazolin-3-yl]acetamide (EXAMPLE 5a) (7.1 mg, 0.014 mmol, 47%).

Data for N-tert-butyl-2-[2-(3-chlorophenyl)-6-(4-isopropylperhydro-1,4-diazepin-1-yl)-4-oxo-4H-quinazolin-3-yl]acetamide (EXAMPLE 5a): $^1$H NMR (300 MHz, CDCl$_3$): δ 7.6 (m, 2H), 7.5-7.3 (m, 4H), 7.21 (dd, 1H), 5.63 (s, 1H), 4.44 (s, 2H), 3.64 (m, 4H), 2.94 (m, 1H), 2.81 (t, 2H), 2.57 (t, 2H), 1.96 (m, 2H), 1.34 (s, 9H), 1.00 (d, 6H) ppm; MS (ESI) m/z: 510/512 ([M+H]+).

The following compounds were prepared in a similar manner from EXAMPLES 1, 2 or 3:

Example 5b

2-[2-(3-Chlorophenyl)-6-(4-isopropylperhydro-1,4-diazepin-1-yl)-4-oxo-4H-quinazolin-3-yl]-N-isopropylacetamide

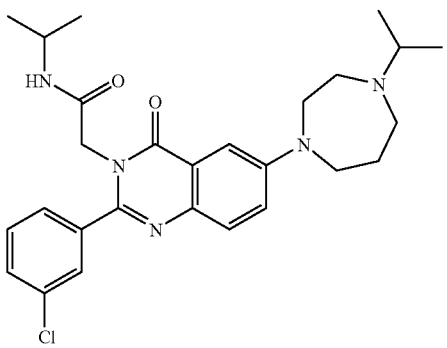

MS (ESI) m/z: 496/498 ([M+H]+) (from EXAMPLE 1b)

Example 5c

N-tert-Butyl-2-[2-(3-chlorophenyl)-6-(4-ethylperhydro-1,4-diazepin-1-yl)-4-oxo-4H-quinazolin-3-yl]acetamide

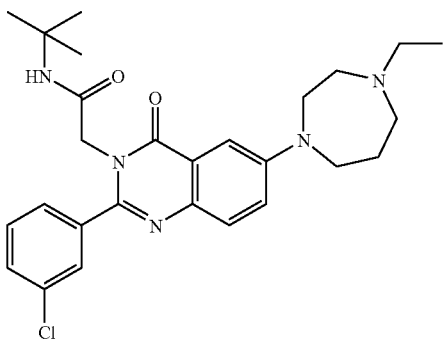

N-tert-Butyl-2-[2-(3-chlorophenyl)-4-oxo-6-perhydro-1,4-diazepin-1-yl-4H-quinazolin-3-yl]acetamide (EXAMPLE 1a) (50 mg, 0.107 mmol), acetaldehyde (7.1 mg, 0.160 mmol) and acetonitrile (1 mL) were placed in a microwave vial. Macroporous triethyammonium methylpolystyrene cyanoborohydride (70 mg, 0.107 mmol) and acetic acid (0.3 mL, 0.107 mmol) were added and the reaction mixture heated in a microwave at 130° C. for 1200 s. Crude product was filtered and the residue dissolved in MeOH (1 mL) and purified by preparative HPLC. This afforded N-tert-butyl-2-[2-(3-chlorophenyl)-6-(4-ethylperhydro-1,4-diazepin-1-yl)-4-oxo-4H-quinazolin-3-yl]acetamide (EXAMPLE 5c) (11 mg, 0.023 mmol, 21%).

N-tert-Butyl-2-[2-(3-chlorophenyl)-6-(4-ethylperhydro-1,4-diazepin-1-yl)-4-oxo-4H-quinazolin-3-yl]acetamide (EXAMPLE 5c): MS (ESI) m/z: 496 ([M+H]$^+$).

Example 5d

2-[2-(3-Chloro-4-fluorophenyl)-6-(4-isopropylpiperazin-1-yl)-4-oxo-4H-quinazolin-3-yl]-N-isopropylacetamide

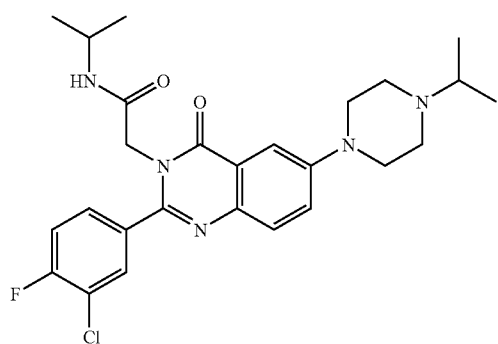

MS (ESI) m/z: 500/502 ([M+H]$^+$) (from EXAMPLE 1g)

Example 5e

2-[2-(3-Chloro-4-fluorophenyl)-6-(4-cyclopropylmethylpiperazin-1-yl)-4-oxo-4H-quinazolin-3-yl]-N-isopropylacetamide

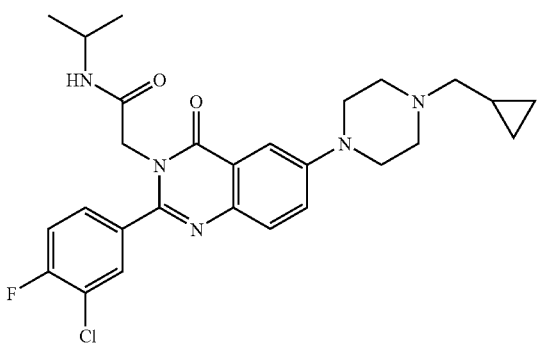

MS (ESI) m/z: 512/514 ([M+H]$^+$) (from EXAMPLE 1g)

Example 5f

2-[2-(3-Chloro-4-fluorophenyl)-6-(4-ethylpiperazin-1-yl)-4-oxo-4H-quinazolin-3-yl]-N-isopropylacetamide

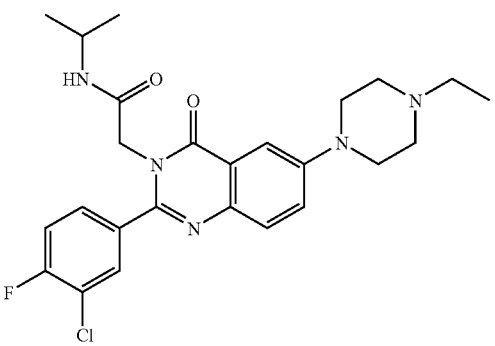

MS (ESI) m/z: 486/488 ([M+H]$^+$) (from EXAMPLE 1g)

Example 5g

2-[2-(3-Chlorophenyl)-4-oxo-6-(4-propylperhydro-1,4-diazepin-1-yl)-4H-quinazolin-3-yl]-N-isopropylacetamide

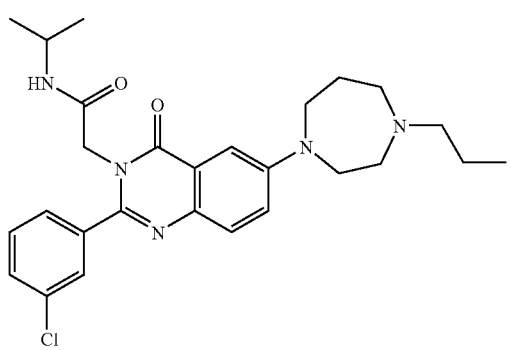

MS (ESI) m/z: 496/498 ([M+H]$^+$) (from EXAMPLE 1b)

Example 5h

2-[6-(3-Ethyl-4-isopropylperhydro-1,4-diazepin-1-yl)-2-(4-fluoro-3-methoxyphenyl)-4-oxo-4H-quinazolin-3-yl]-N-isopropylacetamide

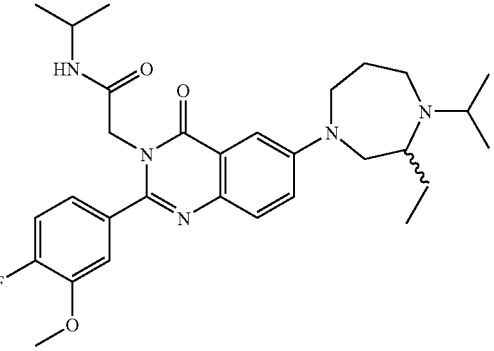

MS (ESI) m/z: 538 ([M+H]$^+$) (from EXAMPLE 6f)

Example 5i

2-[2-(3-Chloro-4-fluorophenyl)-6-(4-isopropyl-3-propylperhydro-1,4-diazepin-1-yl)-4-oxo-4H-quinazolin-3-yl]-N-isopropylacetamide

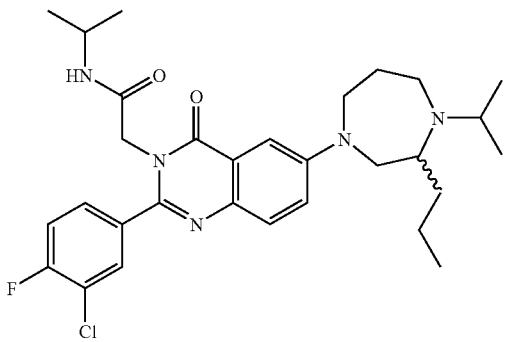

MS (ESI) m/z: 556/558 ([M+H]$^+$) (from EXAMPLE 6Av)

Example 5j

2-[2-(3-Chloro-4-fluorophenyl)-6-((S)-4-cyclopropylmethyl-3-isopropylpiperazin-1-yl)-4-oxo-4H-quinazolin-3-yl]-N-isopropylacetamide

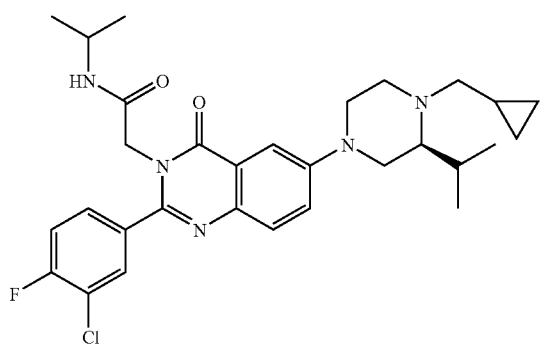

MS (ESI) m/z: 554/556 ([M+H]$^+$) (from EXAMPLE 1f)

Example 5k

2-[2-(3-Chloro-4-fluorophenyl)-6-((R)-4-isopropyl-3-methylpiperazin-1-yl)-4-oxo-4H-quinazolin-3-yl]-N-isopropylacetamide

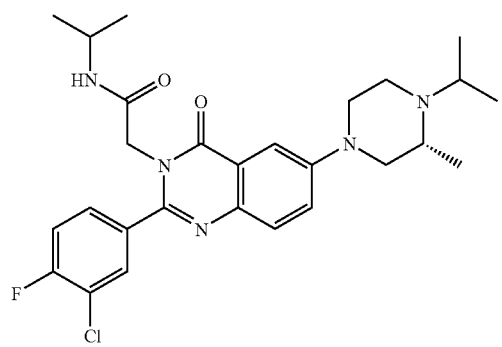

MS (ESI) m/z: 514/516 ([M+H]$^+$) (from EXAMPLE 3x)

Example 5l

2-[2-(3-Chloro-4-fluorophenyl)-6-((R)-4-cyclopropylmethyl-3-methylpiperazin-1-yl)-4-oxo-4H-quinazolin-3-yl]-N-isopropylacetamide

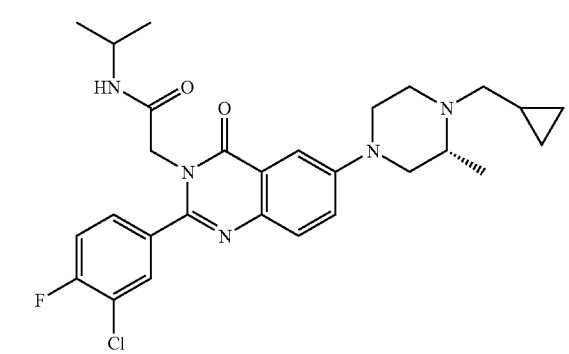

MS (ESI) m/z: 526/528 ([M+H]$^+$) (from EXAMPLE 3x)

Example 5m

N-tert-Butyl-2-[2-(3-chloro-4-fluorophenyl)-6-(4-ethylperhydro-1,4-diazepin-1-yl)-4-oxo-4H-quinazolin-3-yl]acetamide

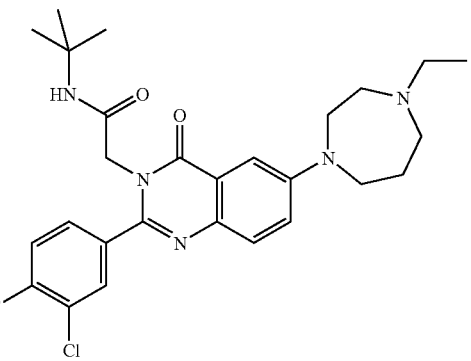

MS (ESI) m/z: 514/516 ([M+H]$^+$) (from EXAMPLE 1c)

Example 5n

N-tert-Butyl-2-[2-(3-chloro-4-fluorophenyl)-6-(4-methylperhydro-1,4-diazepin-1-yl)-4-oxo-4H-quinazolin-3-yl]acetamide

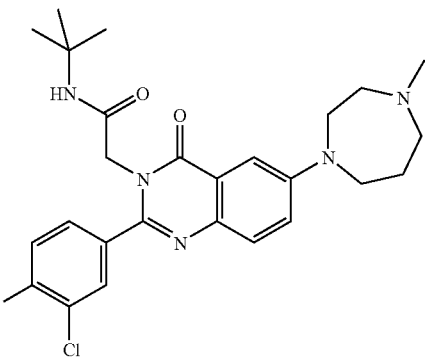

MS (ESI) m/z: 500/502 ([M+H]$^+$) (from EXAMPLE 1c)

Example 5o

N-tert-Butyl-2-[6-(4-ethylperhydro-1,4-diazepin-1-yl)-2-(4-fluoro-3-methoxyphenyl)-4-oxo-4H-quinazolin-3-yl]acetamide

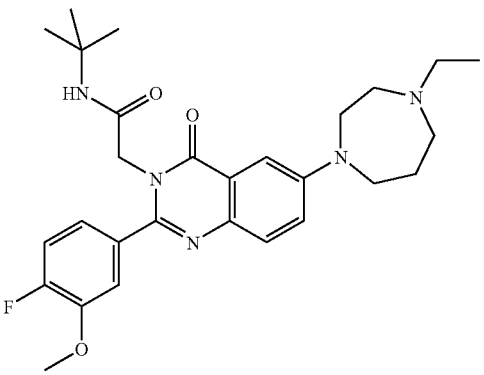

MS (ESI) m/z: 510 ([M+H]$^+$) (from EXAMPLE 1d)

Example 5p

N-tert-Butyl-2-[6-(4-cyclopentylperhydro-1,4-diazepin-1-yl)-2-(4-fluoro-3-methoxyphenyl)-4-oxo-4H-quinazolin-3-yl]acetamide

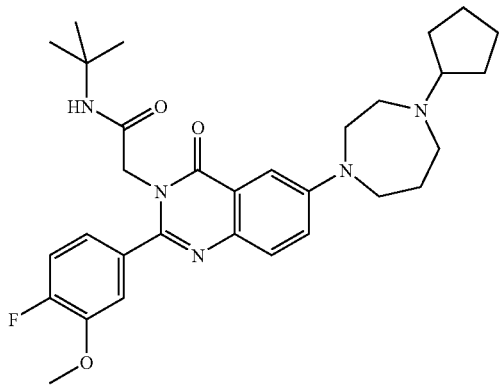

MS (ESI) m/z: 550 ([M+H]$^+$) (from EXAMPLE 1d)

Example 5q

N-tert-Butyl-2-[2-(4-fluoro-3-methoxyphenyl)-6-(4-methylperhydro-1,4-diazepin-1-yl)-4-oxo-4H-quinazolin-3-yl]acetamide

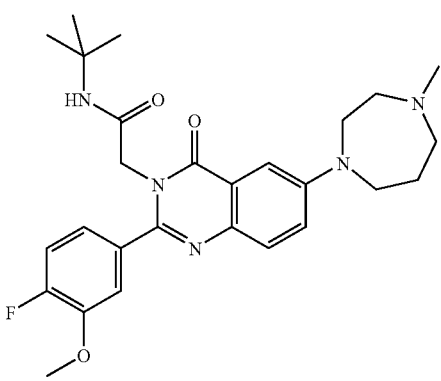

MS (ESI) m/z: 496 ([M+H]$^+$) (from EXAMPLE 1d)

Example 5r

2-[2-(3-Chloro-4-fluorophenyl)-6-(4-isobutylperhydro-1,4-diazepin-1-yl)-4-oxo-4H-quinazolin-3-yl]-N-isopropylacetamide

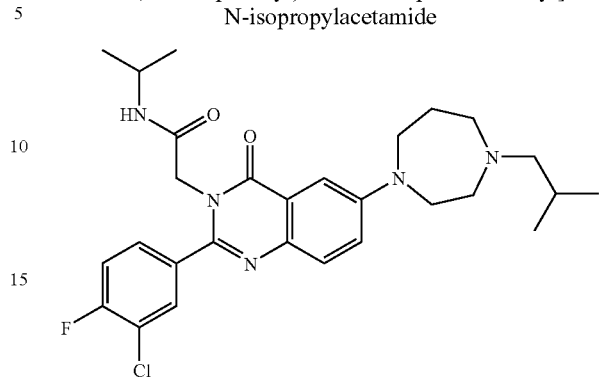

MS (ESI) m/z: 528 ([M+H]$^+$) (from EXAMPLE 1e)

Example 5s

2-[2-(3-Chloro-4-fluorophenyl)-4-oxo-6-(4,6,6-trimethylperhydro-1,4-diazepin-1-yl)-4H-quinazolin-3-yl]-N-isopropylacetamide

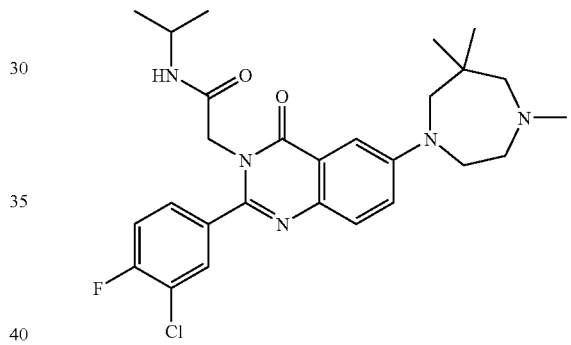

MS (ESI) m/z: 514/516 ([M+H]$^+$) (from EXAMPLE 1k).

Example 5t

2-[2-(4-Fluoro-3-methoxyphenyl)-4-oxo-6-(4,6,6-trimethylperhydro-1,4-diazepin-1-yl)-4H-quinazolin-3-yl]-N-isopropylacetamide

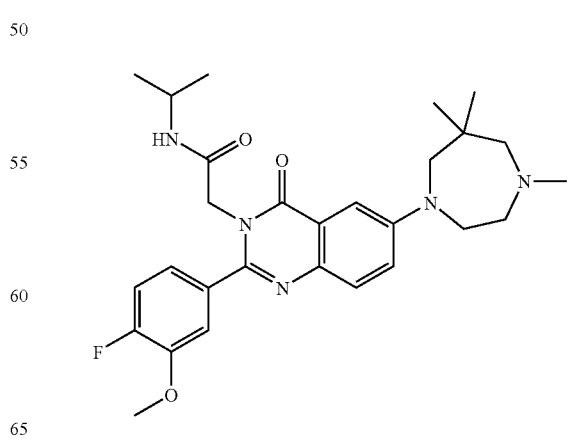

MS (ESI) m/z: 510 ([M+H]$^+$) (from EXAMPLE 1l).

Example 5u

2-[6-[4-(1,2-Dimethylpropyl)perhydro-1,4-diazepin-1-yl]-2-(4-fluoro-3-methoxyphenyl)-4-oxo-4H-quinazolin-3-yl]-N-isopropylacetamide

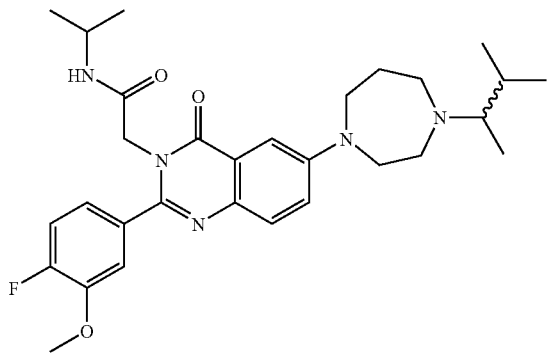

MS (ESI) m/z: 538 ([M+H]$^+$) (from EXAMPLE 1i).

Example 5v

2-[2-(3-Chlorophenyl)-6-(4-ethylperhydro-1,4-diazepin-1-yl)-4-oxo-4H-quinazolin-3-yl]-N-isopropylacetamide

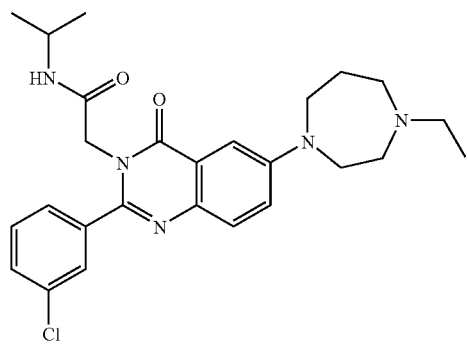

MS (ESI) m/z: 482 ([M+H]$^+$) (from EXAMPLE 1b)

Example 5w

2-[6-(4-sec-Butylperhydro-1,4-diazepin-1-yl)-2-(3-chlorophenyl)-4-oxo-4H-quinazoline-3-yl]-N-isopropylacetamide

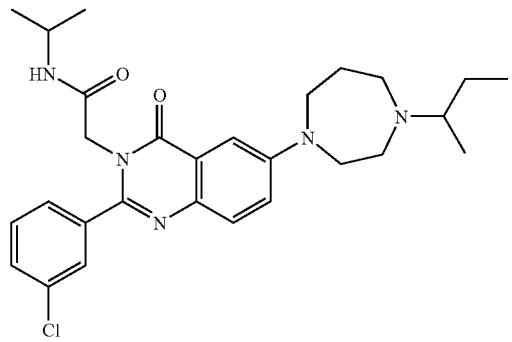

MS (ESI) m/z: 510 ([M+H]$^+$) (from EXAMPLE 1b)

Example 5x

2-[2-(3-Chlorophenyl)-6-(4-cyclopentylmethylperhydro-1,4-diazepin-1-yl)-4oxo-4H-quinazolin-3-yl]-N-isopropylacetamide

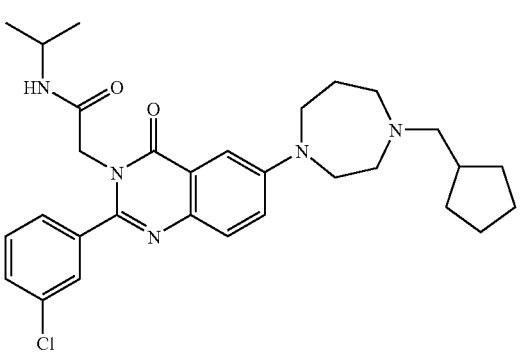

MS (ESI) m/z: 536 ([M+H]$^+$) (from EXAMPLE 1b)

Example 5y

2-{2-(3-Chlorophenyl)-6-[4-dimethylamino-1-methylethyl)perhydro-1,4-diazepin-1-yl]-4-oxo-4H-quinazolin-3-yl}-N-isopropylacetamide

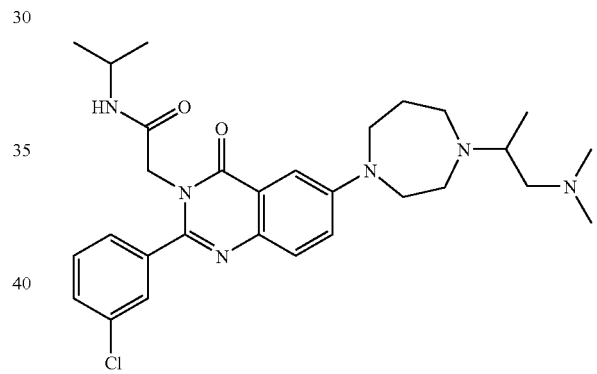

MS (ESI) m/z: 540 ([M+H]$^+$) (from EXAMPLE 1b)

Example 5z

2-{2-(3-Chlorophenyl)-6-[4-(3-methylethyl)perhydro-1,4-diazepin-1-yl]-4-oxo-4H-quinazolin-3-yl}-N-isopropylacetamide

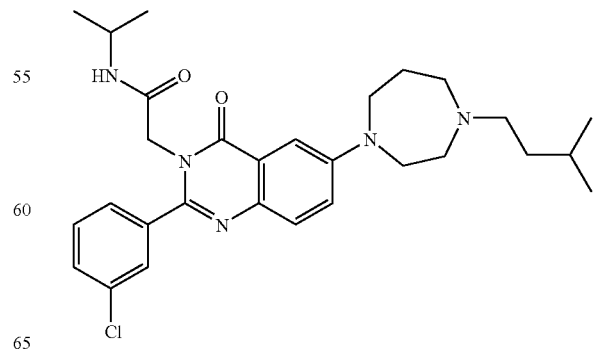

MS (ESI) m/z: 524 ([M+H]$^+$) (from EXAMPLE 1b)

Example 5Aa

2-{2-(3-Chlorophenyl)-6-[4-(2-methyoxy-1-methylethyl)perhydro-1,4-diazepin-1-yl]-4-oxo-4H-quinazolin-3-yl}-N-isopropylacetamide

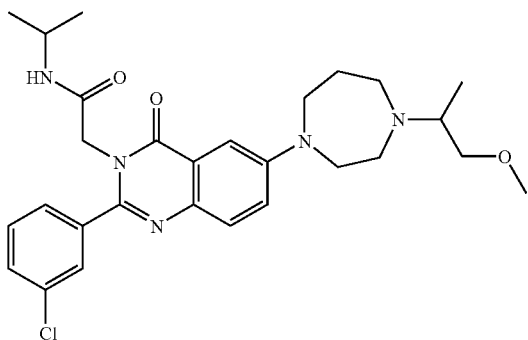

Example 5Ab

2-{2-(3-Chloro-4-fluorophenyl)-6-[(1-cyclopropylethyl)perhydro-1,4-diazepin-1-yl]-4-oxo-4H-quinazolin-3-yl}-N-isopropylacetamide

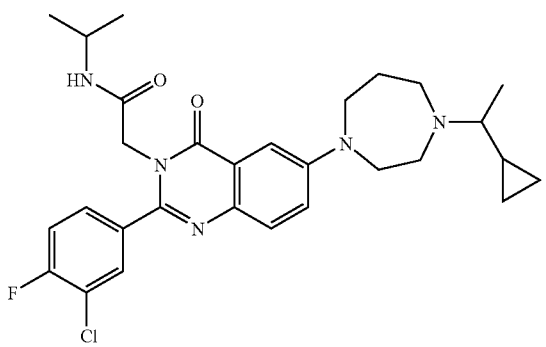

MS (ESI) m/z: 540/542 ([M+H]$^+$) (from EXAMPLE 1e).

Example 5Ac

2-{2-(3-Chloro-4-fluorophenyl)-6-[4-(2,2-dimethylpropyl)perhydro-1,4-diazepin-1-yl]-4-oxo-4H-quinazolin-3-yl}-N-isopropylacetamide

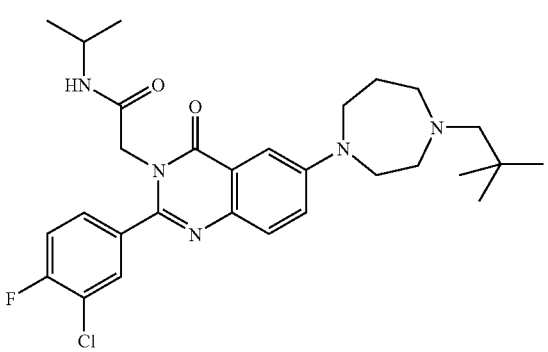

MS (ESI) m/z: 542 ([M+H]$^+$) (from EXAMPLE 1e).

Example 5Ad

2-[2-(3-Chloro-4-fluorophenyl)-6-(4-cyclopentylperhydro-1,4-diazepin-1-yl)-4-oxo-4H-quinazolin-3-yl]-N-isopropylacetamide

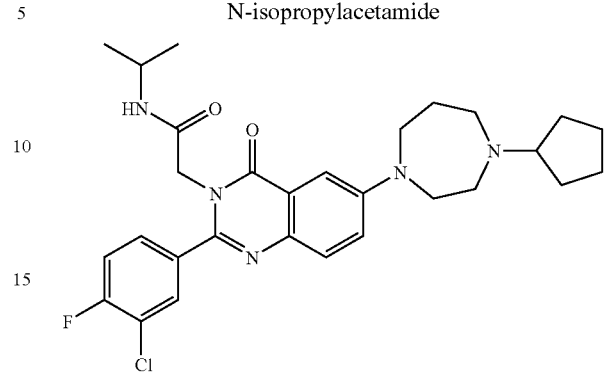

MS (ESI) m/z: 540 ([M+H]$^+$) (from EXAMPLE 1e).

Example 5Ae

2-[6-[4-(1-Ethylpropyl)perhydro-1,4-diazepin-1-yl]-2-(4-fluoro-3-methoxyphenyl)-4-oxo-4H-quinazolin-3-yl]-N-isopropylacetamide

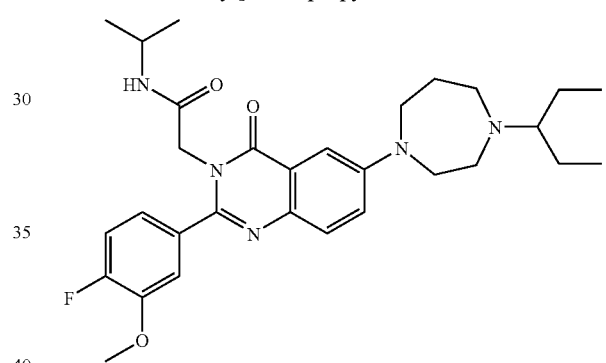

MS (ESI) m/z: 538 ([M+H]$^+$) (from EXAMPLE 1i).

Example 5Af

2-[6-(4-Cyclopentylmethylperhydro-1,4-diazepin-1-yl)-2-(4-fluoro-3-methoxyphenyl)-4-oxo-4H-quinazolin-3-yl]-N-isopropylacetamide

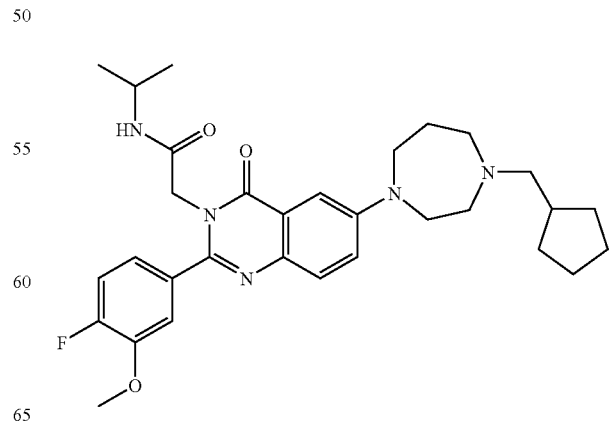

MS (ESI) m/z: 550 ([M+H]$^+$) (from EXAMPLE 1i).

Example 5Ag

2-[6-(4-Cyclobutylperhydro-1,4-diazepin-1-yl)-2-(4-fluoro-3-methoxyphenyl)-4-oxo-4H-quinazolin-3-yl]-N-isopropylacetamide

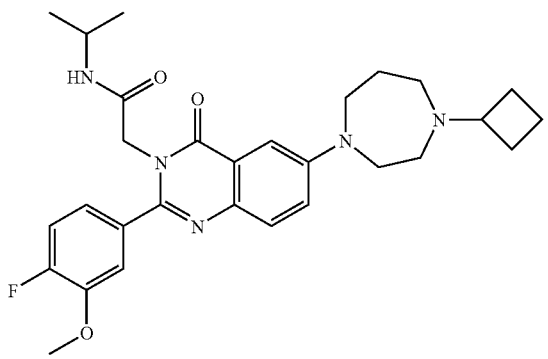

MS (ESI) m/z: 522 ([M+H]$^+$) (from EXAMPLE 1i).

Example 5Ah

2-[6-(4-Ethylperhydro-1,4-diazepin-1-yl)-2-(4-fluoro-3-methoxyphenyl)-4-oxo-4H-quinazolin-3-yl]-N-isopropylacetamide

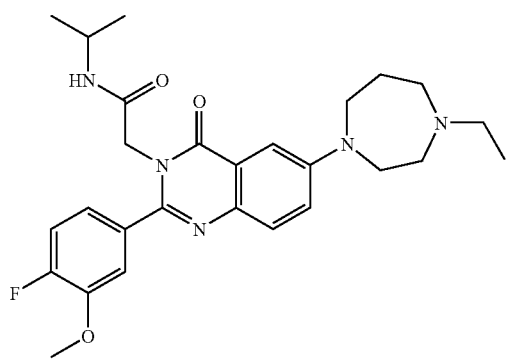

MS (ESI) m/z: 496 ([M+H]$^+$) (from EXAMPLE 1i).

Example 5Ai

2-[2-(4-Fluoro-3-methoxyphenyl)-4-oxo-6-(4-propylperhydro-1,4-diazepin-1-yl)-4H-quinazolin-3-yl]-N-isopropylacetamide

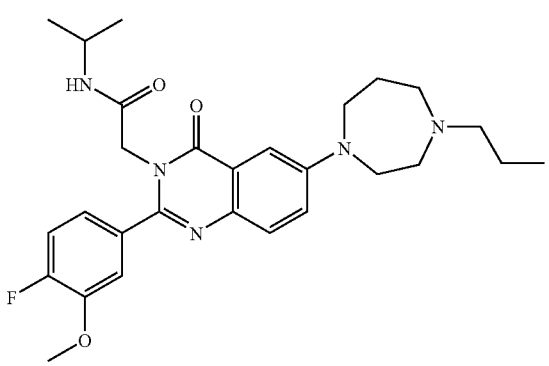

MS (ESI) m/z: 510 ([M+H]$^+$) (from EXAMPLE 1i).

Example 5Aj

2-[6-(4-Butylperhydro-1,4-diazepin-1-yl)-2-(4-fluoro-3-methoxyphenyl)-4-oxo-4H-quinazolin-3-yl]-N-isopropylacetamide

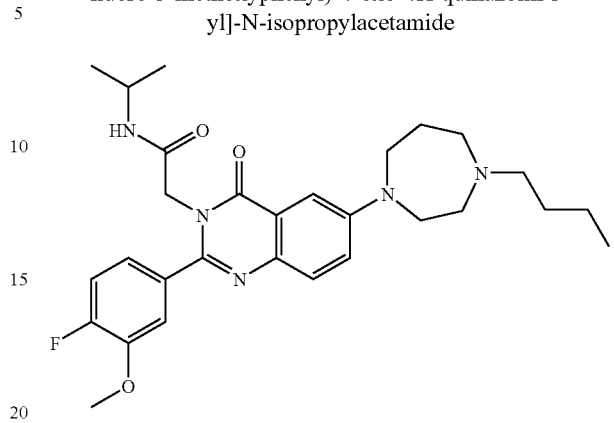

MS (ESI) m/z: 525 ([M+H]$^+$) (from EXAMPLE 1i).

Example 5Ak

2-{2-(4-Fluoro-3-methoxyphenyl)-6-[4-(1-methylbutyl)perhydro-1,4-diazepin-1-yl]-4-oxo-4H-quinazolin-3-yl}-N-isopropylacetamide

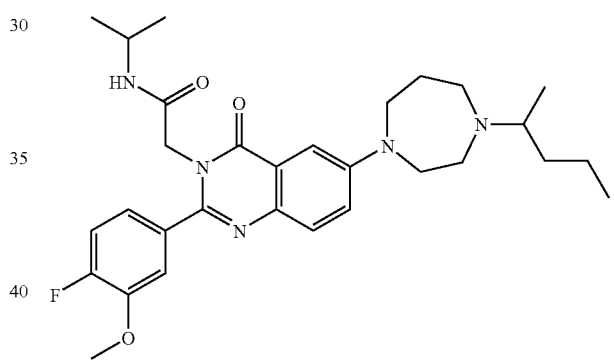

MS (ESI) m/z: 538 ([M+H]$^+$) (from EXAMPLE 1i).

Example 5Al

2-[2-(4-Fluoro-3-methoxyphenyl)-6-(4-methylperhydro-1,4-diazepin-1-yl)-4-oxo-4H-quinazolin-3-yl]-N-isopropylacetamide

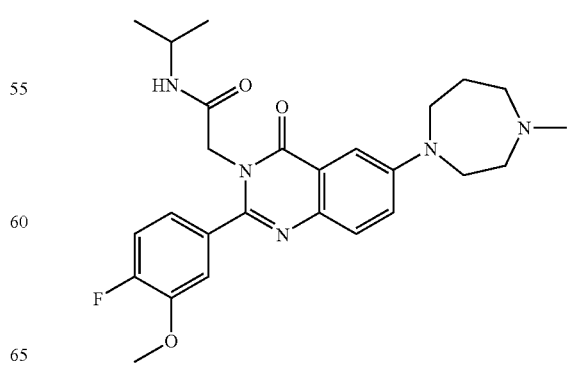

MS (ESI) m/z: 482 ([M+H]$^+$) (from EXAMPLE 1i).

Example 5Am

2-[2-(3-Chloro-4-fluorophenyl)-6-(4-ethylperhydro-1,4-diazepin-1-yl)-4-oxo-4H-quinazolin-3-yl]-N-isopropylacetamide

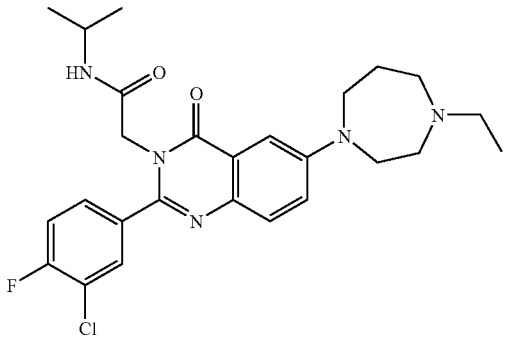

MS (ESI) m/z: 500 ([M+H]⁺) (from EXAMPLE 1e).

Example 5An

2-[2-(3-Chloro-4-fluorophenyl)-4-oxo-6-(4-propylperhydro-1,4-diazepin-1-yl)-4H-quinazolin-3-yl]-N-isopropyl-cetamide

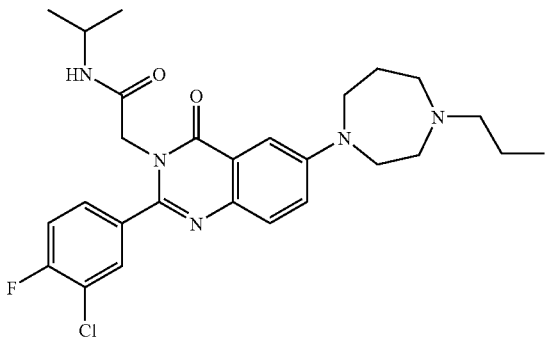

MS (ESI) m/z: 514 ([M+H]⁺) (from EXAMPLE 1e).

Example 5Ao

2-[2-(3-Chloro-4-fluorophenyl)-6-(4-isopropyl-3-methylperhydro-1,4-diazepin-1-yl)-4-oxo-4H-quinazolin-3-yl]-N-isopropylacetamide

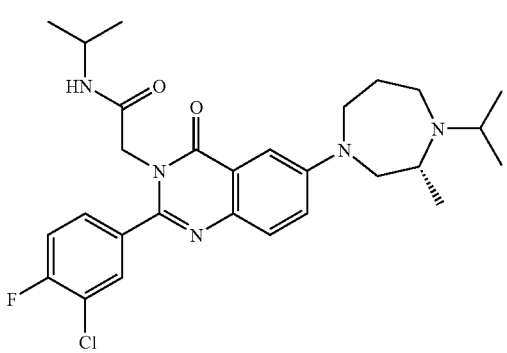

MS (ESI) m/z: 528/530 ([M+H]⁺) (from EXAMPLE 1h).

Example 6a

2-[2-(3-Chloro-4-fluorophenyl)-6-(3-ethylperhydro-1,4-diazepin-1-yl)-4-oxo-4H-quinazolin-3-yl]-N-isopropylacetamide

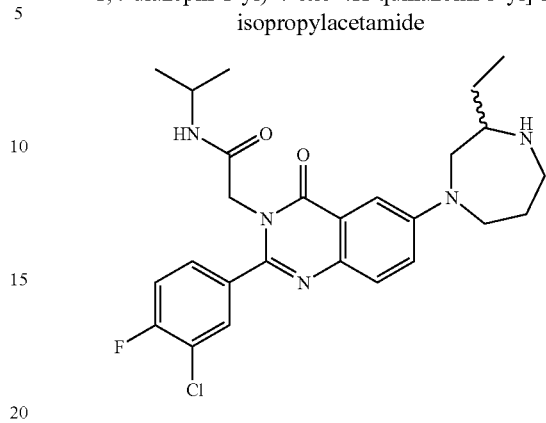

2-Amino-5-(3-ethylperhydro-1,4-diazepin-1-yl)-N-(isopropylcarbamoylmethyl)benzamide (INTERMEDIATE V.26) (100 mg, 0.277 mmol), 3-chloro-4-fluorobenzaldehyde (51 mg, 0.332 mmol) and acetic acid (4 drops, catalytic) (0.33 mmol) were dissolved in ethanol (4 mL) in a microwave vial and the vial sealed. The reaction mixture was stirred at 90° C. for 16 h. The reaction mixture was evaporated to dryness, re-dissolved in DCM and manganese dioxide (105 mg, 1.11 mmol) was added. The reaction mixture was stirred in a sealed vial at 60° C. for 3 h. Solvent was evaporated under reduced pressure and crude product purified by chromatography on silica gel with a gradient of DCM to MeOH:DCM (1:4, v/v) as eluent. This afforded 2-[2-(3-chloro-4-fluorophenyl)-6-(3-ethylperhydro-1,4-diazepin-1-yl)-4-oxo-4H-quinazolin-3-yl]-N-isopropylacetamide (EXAMPLE 6a) (95 mg, 0.192 mmol, 69%). Data for 2-[2-(3-chloro-4-fluorophenyl)-6-(3-ethylperhydro-1,4-diazepin-1-yl)-4-oxo-4H-quinazolin-3-yl]-N-isopropylacetamide (EXAMPLE 6a): MS (ESI) m/z: 500/502 ([M+H]⁺).

Similarly prepared from INTERMEDIATES V were:

Example 6b

2-[2-(3-Chlorophenyl)-6-(hexahydropyrrolo[1,2-a]pyrazin-2-yl)-4-oxo-4H-quinazolin-3-yl]-N-isopropylacetamide

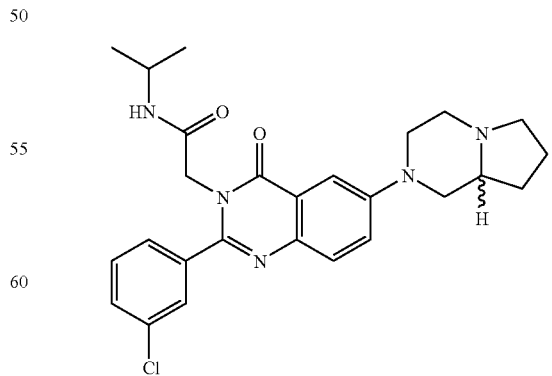

MS (ESI) m/z: 480/482 ([M+H]⁺) (from INTERMEDIATE V.48)

Example 6c

2-[2-(3-Chloro-4-fluorophenyl)-6-(hexahydropyrrolo [1,2-a]pyrazin-2-yl)-4-oxo-4H-quinazolin-3-yl]-N-isopropylacetamide

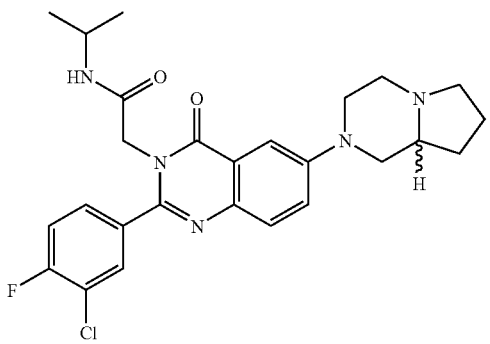

MS (ESI) m/z: 498/500 ([M+H]$^+$) (from INTERMEDIATE V.48)

Example 6d

2-[2-(3-Chloro-4-fluorophenyl)-6-(3-fluoromethylpiperazin-1-yl)-4-oxo-4H-quinazolin-3-yl]-N-isopropylacetamide

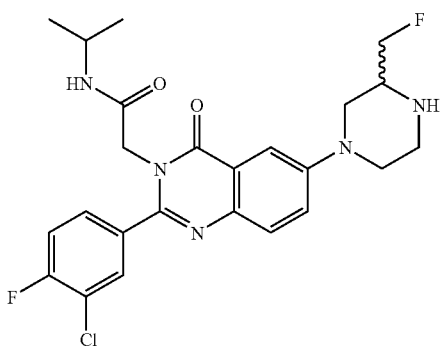

MS (ESI) m/z: 490/492 ([M+H]$^+$) (from INTERMEDIATE V.27)

Example 6e

2-[2-(3-Chloro-4-fluorophenyl)-6-(dimethylpiperazin-1-yl)-4-oxo-4H-quinazolin-3-yl]-N-isopropylacetamide

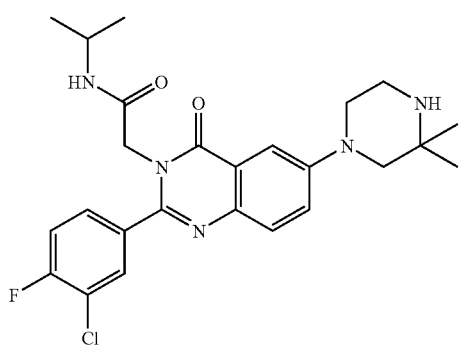

MS (ESI) m/z: 486/488 ([M+H]$^+$) (from INTERMEDIATE V.19)

Example 6f

2-[6-(3-Ethylperhydro-1,4-diazepin-1-yl)-2-(4-fluoro-3-methoxyphenyl)-4-oxo-4H-quinazolin-3-yl]-N-isopropylacetamide

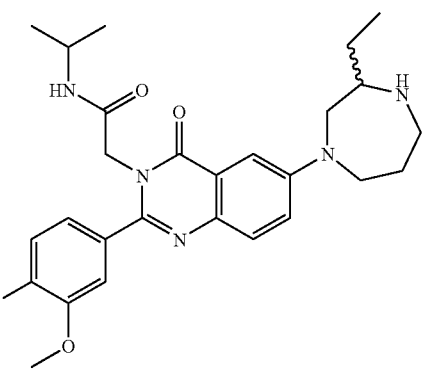

MS (ESI) m/z: 496 ([M+H]$^+$) (from INTERMEDIATE V.26)

Example 6g

2-[2-(3-Chlorophenyl)-6-(3-ethylperhydro-1,4-diazepin-1-yl)-4-oxo-4H-quinazolin-3-yl]-N-isopropylacetamide

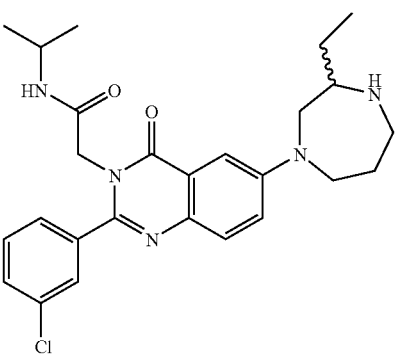

MS (ESI) m/z: 482/484 ([M+H]$^+$) (from INTERMEDIATE V.26)

Example 6h

2-[6-(1,4-Diazabicyclo[3.2.2]non-4-yl)-2-(3-methoxyphenyl)-4-oxo-4H-quinazolin-3-yl]-N-isopropylacetamide

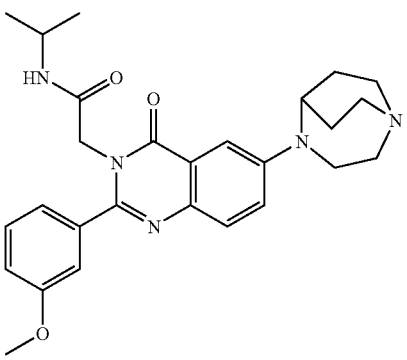

MS (ESI) m/z: 476 ([M+H]$^+$) (from INTERMEDIATE V.47)

Example 6i

2-[2-(3-Chlorophenyl)-4-oxo-6-((S)-2-pyrrolidin-1-ylmethylpyrrolidin-1-yl)-4H-quinazolin-3-yl]-N-isopropylacetamide

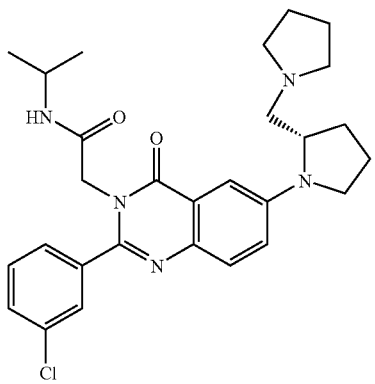

MS (ESI) m/z: 508/510 ([M+H]$^+$) (from INTERMEDIATE V.28)

Example 6j

2-[2-(4-Fluoro-3-methoxyphenyl)-6-((R)-3-methylpiperazin-1-yl)-4-oxo-4H-quinazolin-3-yl]-N-isopropylacetamide

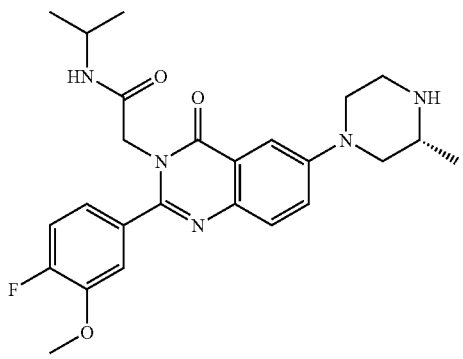

MS (ESI) m/z: 468 ([M+H]$^+$) (from INTERMEDIATE V.25)

Example 6k

2-[2-(3-Chloro-4-fluorophenyl)-6-(4-isopropylperhydro-1,4-diazepin-1-yl)-4-oxo-4H-quinazolin-3-yl]-N-isopropylacetamide

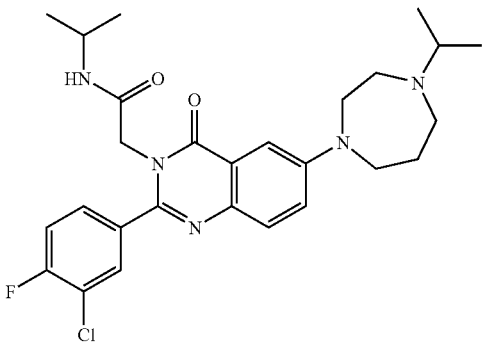

2-Amino-5-(4-isopropyl-1,4-diazepan-1-yl)-N-(2-(isopropylamino)-2-oxoethyl)benzamide (INTERMEDIATE V.31) (400 mg, 1.07 mmol), 3-chloro-4-fluorobenzaldehyde (253 mg, 1.60 mmol) and acetic acid (0.01 mL) were dissolved in ethanol (12 mL). The reaction mixture was heated at 90° C. overnight. The reaction mixture was filtered, the residue washed with EtOAc, and the filtrate evaporated under reduced pressure. Crude product was purified by SCX eluting with 2N NH$_3$/MeOH to give a purple solid.

This solid was dissolved in toluene (12.00 mL) and potassium hexacyanoferrate (III) (3.51 g, 10.65 mmol) added followed by water (12 mL) and 10M KOH (aq.) (4 mL). The reaction mixture was stirred at room temperature overnight. The reaction mixture was acidified with conc. HCl, diluted with MeOH (10 mL) and filtered. The residue was washed with MeOH and the filtrate purified by SCX, eluting with 2N NH$_3$/MeOH. Crude product was purified by chromatography on silica gel with a gradient of DCM to DCM:MeOH:NH$_3$ (94:5:1, v/v) as eluent to afford 2-[2-(3-chloro-4-fluorophenyl)-6-(4-isopropylperhydro-1,4-diazepin-1-yl)-4-oxo-4H-quinazolin-3-yl]-N-isopropylacetamide (EXAMPLE 6k) (155 mg, 0.302 mmol, 28%). Data for 2-[2-(3-chloro-4-fluorophenyl)-6-(4-isopropylperhydro-1,4-diazepin-1-yl)-4-oxo-4H-quinazolin-3-yl]-N-isopropylacetamide (EXAMPLE 6k): MS (ESI) m/z: 515/517 ([M+H]$^+$).

Example 6l

2-[2-(3-Chloro-4-fluorophenyl)-6-(5-methylperhydro-1,4-diazepin-1-yl)-4-oxo-4H-quinazolin-3-yl]-N-isopropylacetamide

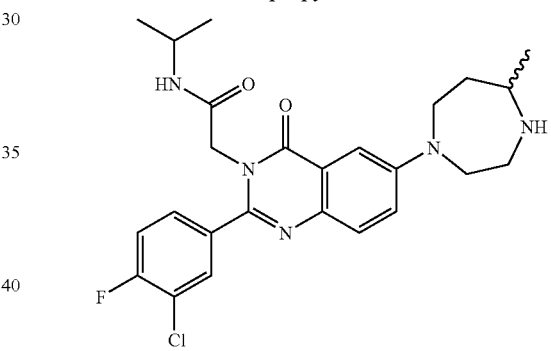

MS (ESI) m/z: 486/488 ([M+H]$^+$) (from INTERMEDIATE V.29).

Example 6m

2-[2-(3,5-Dimethoxyphenyl)-4-oxo-6-perhydro-1,4-diazepin-1-yl-4H-quinazolin-3-yl]-N-isopropylacetamide

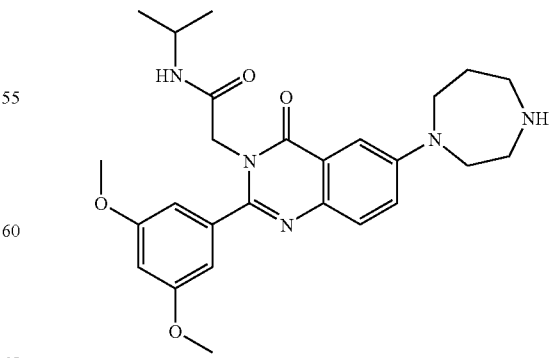

MS (ESI) m/z: 480 ([M+H]$^+$) (from INTERMEDIATE V.2)

Example 6n

2-[2-(3-Chloro-5-trifluoromethylphenyl)-4-oxo-6-perhydro-1,4-diazepin-1-yl-4H-quinazolin-3-yl]-N-isopropylacetamide

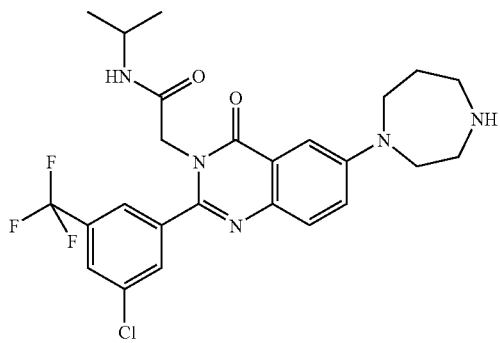

MS (ESI) m/z: 522/524 ([M+H]$^+$) (from INTERMEDIATE V.2).

Example 6o

2-[2-(3,5-Difluorophenyl)-6-(4-isopropylperhydro-1,4-diazepin-1-yl)-4-oxo-4H-quinazolin-3-yl]-N-isopropylacetamide

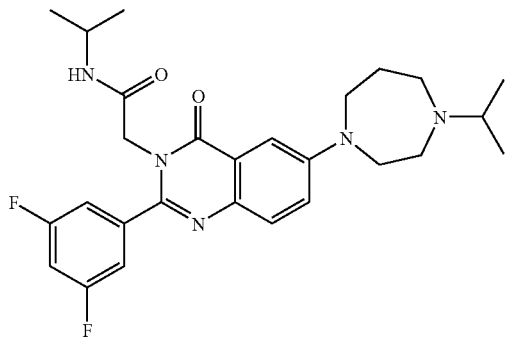

MS (ESI) m/z: 498 ([M+H]$^+$) (from INTERMEDIATE V.31).

Example 6p

2-[2-(3,5-Dichlorophenyl)-6-(4-isopropyl-perhydro-1,4-diazepin-1-yl)-4-oxo-4H-quinazolin-3-yl]-N-isopropylacetamide

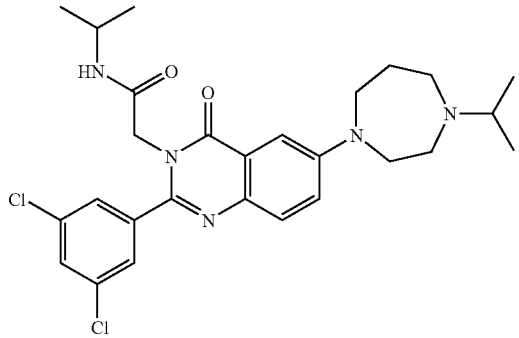

MS (ESI) m/z: 530/532/534 ([M+H]$^+$) (from INTERMEDIATE V.31).

Example 6q

2-[2-(3-Chloro-5-fluorophenyl)-6-(4-isopropylperhydro-1,4-diazepin-1-yl)-4-oxo-4H-quinazolin-3-yl]-N-isopropylacetamide

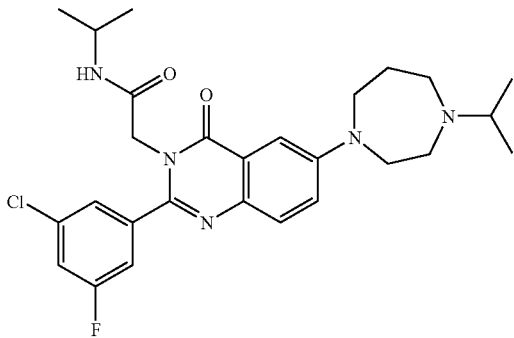

MS (ESI) m/z: 514/516 ([M+H]$^+$) (from INTERMEDIATE V.31).

Example 6r

2-[2-(3-Fluoro-5-trifluoromethylphenyl)-6-(4-isopropylperhydro-1,4-diazepin-1-yl)-4-oxo-4H-quinazolin-3-yl]-N-isopropylacetamide

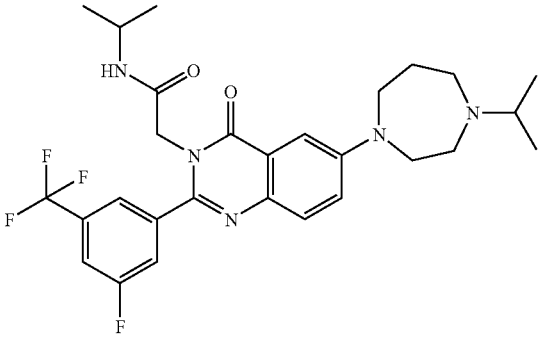

MS (ESI) m/z: 548 ([M+H]$^+$) (from INTERMEDIATE V.31).

Example 6s

N-Isopropyl-2-[6-(4-isopropylperhydro-1,4-diazepin-1-yl)-2-(3-methoxy-5-trifluoromethylphenyl)-4-oxo-4H-quinazolin-3-yl]acetamide

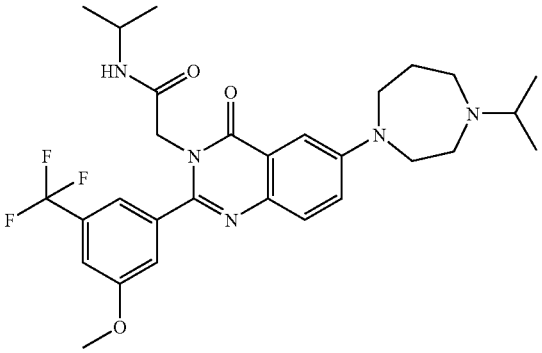

MS (ESI) m/z: 560 ([M+H]$^+$) (from INTERMEDIATE V.31).

Example 6t

2-[2-(3,5-Dimethylphenyl)-6-(4-isopropylperhydro-1,4-diazepin-1-yl)-4-oxo-4H-quinazolin-3-yl]-N-isopropylacetamide

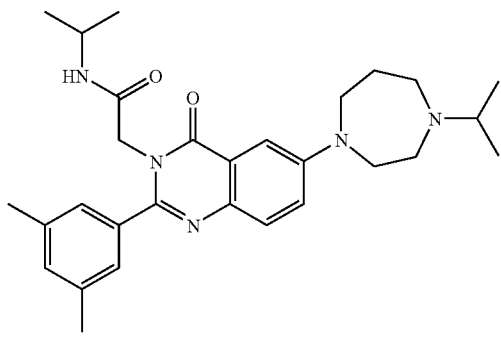

MS (ESI) m/z: 490 ([M+H]$^+$) (from INTERMEDIATE V.31).

Example 6u

2-[2-(3,5-Dimethoxyphenyl)-6-(4-isopropylperhydro-1,4-diazepin-1-yl)-4-oxo-4H-quinazolin-3-yl]-N-isopropylacetamide

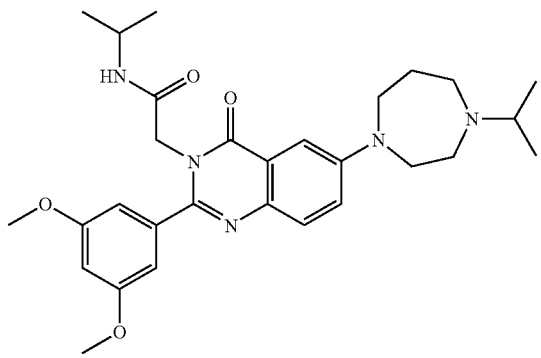

MS (ESI) m/z: 522 ([M+H]$^+$) (from INTERMEDIATE V.31).

Example 6v

2-[2-(3-Chloro-5-trifluoromethylphenyl)-6-(4-isopropylperhydro-1,4-diazepin-1-yl)-4-oxo-4H-quinazolin-3-yl]-N-isopropylacetamide

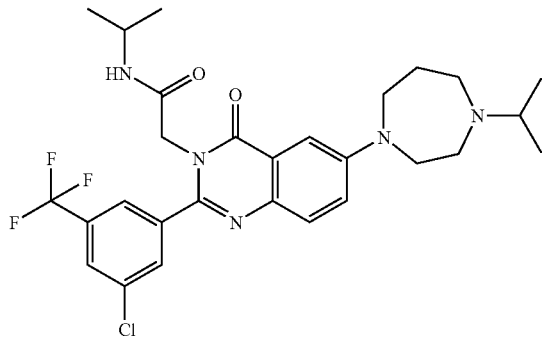

MS (ESI) m/z: 564/566 ([M+H]$^+$) (from INTERMEDIATE V.31).

Example 6w

2-[2-(3-Chloro-5-trifluoromethoxyphenyl)-6-(4-isopropylperhydro-1,4-diazepin-1-yl)-4-oxo-4H-quinazolin-3-yl]-N-isopropylacetamide

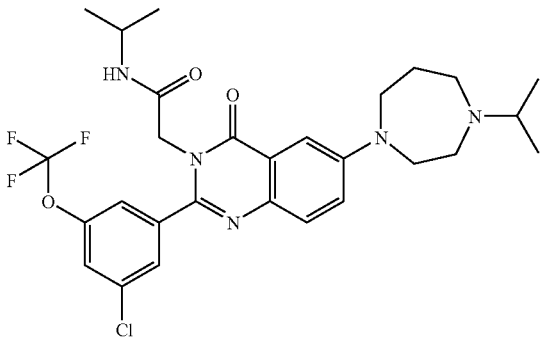

MS (ESI) m/z: 580/582 ([M+H]$^+$) (from INTERMEDIATE V.31).

Example 6x

2-[2-(2-Fluoro-3-methoxyphenyl)-6-(4-isopropylperhydro-1,4-diazepin-1-yl)-4-oxo-4H-quinazolin-3-yl]-N-isopropylacetamide

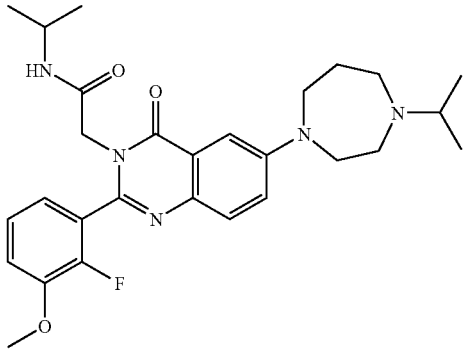

MS (ESI) m/z: 510 ([M+H]$^+$) (from INTERMEDIATE V.31).

Example 6y

2-[2-(2-Fluoro-3-trifluoromethylphenyl)-6-(4-isopropylperhydro-1,4-diazepin-1-yl)-4-oxo-4H-quinazolin-3-yl]-N-isopropylacetamide

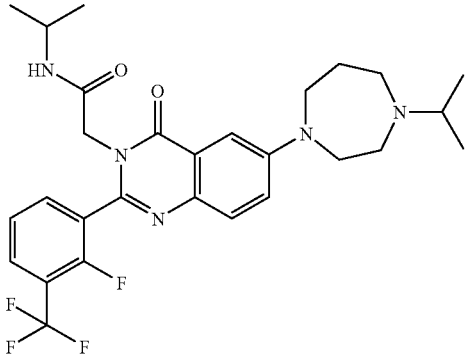

MS (ESI) m/z: 548 ([M+H]$^+$) (from INTERMEDIATE V.31).

Example 6z

2-[2-(2,3-Dichlorophenyl)-6-(4-isopropylperhydro-1,4-diazepin-1-yl)-4-oxo-4H-quinazolin-3-yl]-N-isopropylacetamide

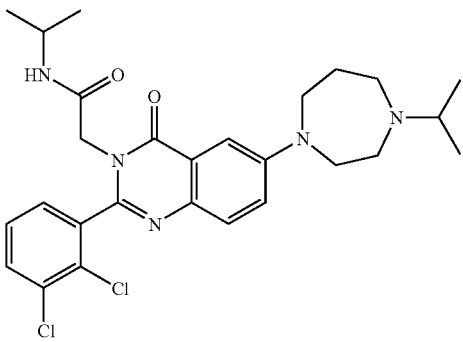

MS (ESI) m/z: 530/532 ([M+H]⁺) (from INTERMEDIATE V.31).

Example 6Aa

2-{2-(3-Chloro-4-fluorophenyl)-6-[3-(2-methanesulfonylethyl)perhydro-1,4-diazepin-1-yl]-4-oxo-4H-quinazolin-3-yl}-N-isopropylacetamide

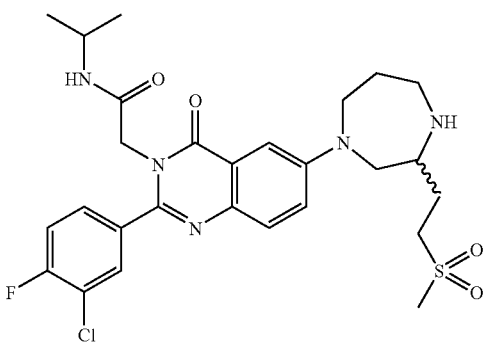

MS (ESI) m/z: 578/580 ([M+H]⁺) (from INTERMEDIATE V.33).

Example 6Ab

2-{2-(3-Chlorophenyl)-6-[3-(2-methanesulfonylethyl)perhydro-1,4-diazepin-1-yl]-4-oxo-4H-quinazolin-3-yl}-N-isopropylacetamide

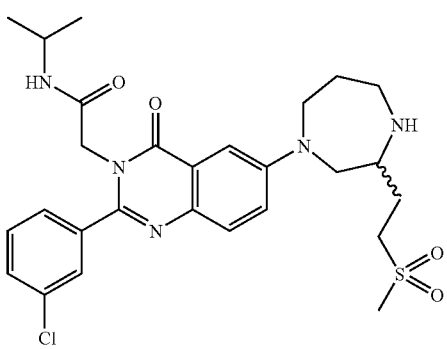

MS (ESI) m/z: 560/562 ([M+H]⁺) (from INTERMEDIATE V.33).

Example 6Ac

2-{2-(4-Fluoro-3-methoxyphenyl)-6-[3-(2-methanesulfonylethyl)perhydro-1,4-diazepin-1-yl]-4-oxo-4H-quinazolin-3-yl}-N-isopropylacetamide

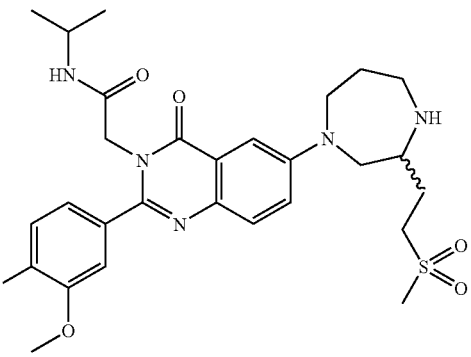

MS (ESI) m/z: 574 ([M+H]⁺) (from INTERMEDIATE V.33).

Example 6Ad

2-[2-(3-Chloro-4-fluorophenyl)-6-((S)-3-isopropylperhydro-1,4-diazepin-1-yl)-4-oxo-4H-quinazolin-3-yl]-N-isopropylacetamide

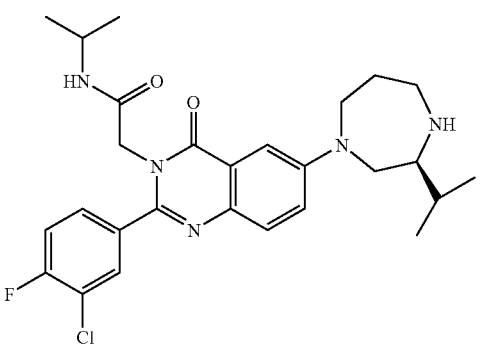

MS (ESI) m/z: 514/516 ([M+H]⁺) (from INTERMEDIATE V.34).

Example 6Ae

2-[2-(3-Chlorophenyl)-6-((S)-3-isopropylperhydro-1,4-diazepin-1-yl)-4-oxo-4H-quinazolin-3-yl]-N-isopropylacetamide

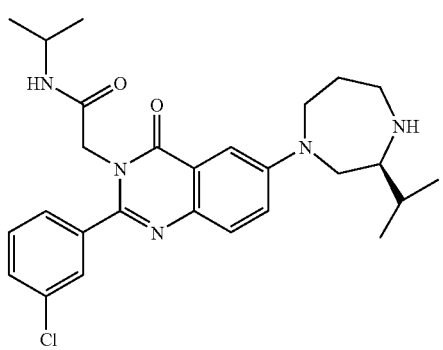

MS (ESI) m/z: 496/498 ([M+H]⁺) (from INTERMEDIATE V.34).

Example 6Af

2-[2-(4-Fluoro-3-methoxyphenyl)-6-((S)-3-isopropylperhydro-1,4-diazepin-1-yl)-4-oxo-4H-quinazolin-3-yl]-N-isopropylacetamide

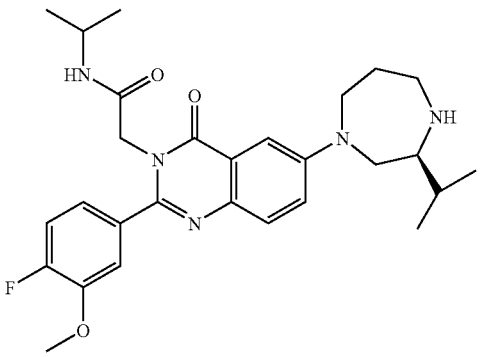

MS (ESI) m/z: 510 ([M+H]$^+$) (from INTERMEDIATE V.34).

Example 6Ag

2-[2-(3-Chloro-4-fluorophenyl)-6-((R)-3-isopropylperhydro-1,4-diazepin-1-yl)-4-oxo-4H-quinazolin-3-yl]-N-isopropylacetamide

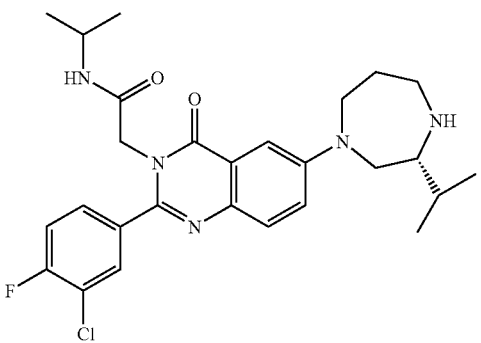

MS (ESI) m/z: 514/516 ([M+H]$^+$) (from INTERMEDIATE V.35).

Example 6Ah

2-[2-(3-Chlorophenyl)-6-((R)-3-isopropylperhydro-1,4-diazepin-1-yl)-4-oxo-4H-quinazolin-3-yl]-N-isopropylacetamide

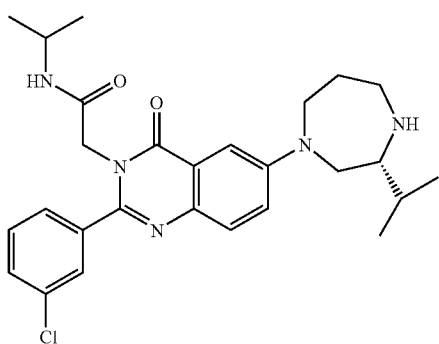

MS (ESI) m/z: 496/498 ([M+H]$^+$) (from INTERMEDIATE V.35).

Example 6Ai

2-[2-(4-Fluoro-3-methoxyphenyl)-6-((R)-3-isopropylperhydro-1,4-diazepin-1-yl)-4-oxo-4H-quinazolin-3-yl]-N-isopropylacetamide

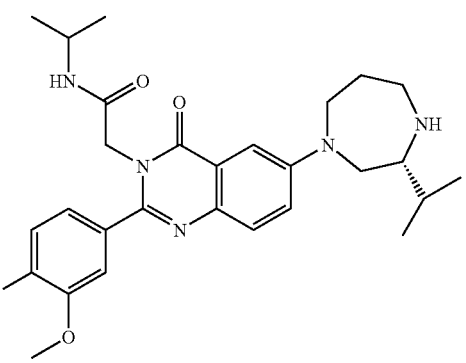

MS (ESI) m/z: 510 ([M+H]$^+$) (from INTERMEDIATE V.35).

Example 6Aj

2-[2-(4-Chloro-3-fluorophenyl)-6-(4-isopropylperhydro-1,4-diazepin-1-yl)-4-oxo-4H-quinazolin-3-yl]-N-isopropylacetamide

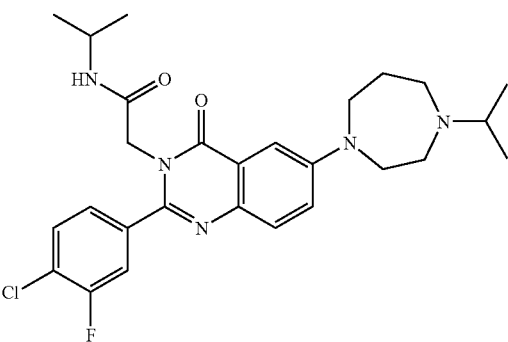

MS (ESI) m/z: 514/516 ([M+H]$^+$) (from INTERMEDIATE V.31).

Example 6Ak

2-[2-(4-Fluoro-3-trifluoromethylphenyl)-6-(4-isopropylperhydro-1,4-diazepin-1-yl)-4-oxo-4H-quinazolin-3-yl]-N-isopropylacetamide

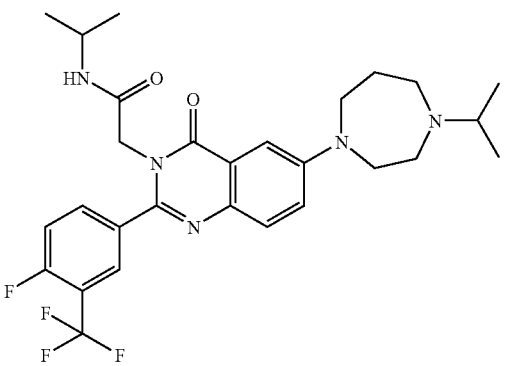

MS (ESI) m/z: 548 ([M+H]$^+$) (from INTERMEDIATE V.31).

Example 6Al

N-Isopropyl-2-[6-(4-isopropylperhydro-1,4-diazepin-1-yl)-2-(3-methoxy-4-methylphenyl)-4-oxo-4H-quinazolin-3-yl]acetamide

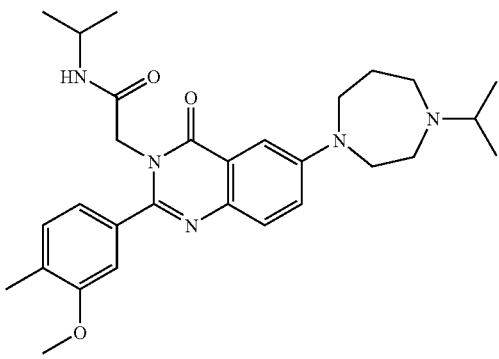

MS (ESI) m/z: 506 ([M+H]$^+$) (from INTERMEDIATE V.31).

Example 6Am

2-[2-(3-Fluoro-4-methylphenyl)-6-(4-isopropylperhydro-1,4-diazepin-1-yl)-4-oxo-4H-quinazolin-3-yl]-N-isopropylacetamide

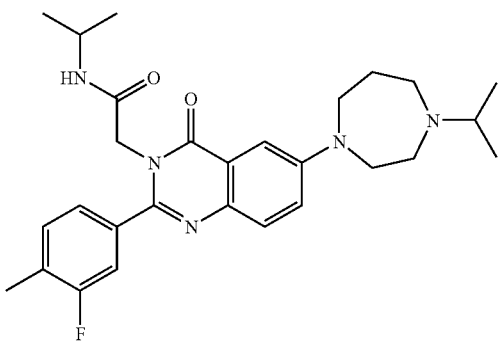

MS (ESI) m/z: 494 ([M+H]$^+$) (from INTERMEDIATE V.31).

Example 6An

2-[2-(3,4-Dichlorophenyl)-6-(4-isopropylperhydro-1,4-diazepin-1-yl)-4-oxo-4H-quinazolin-3-yl]-N-isopropylacetamide

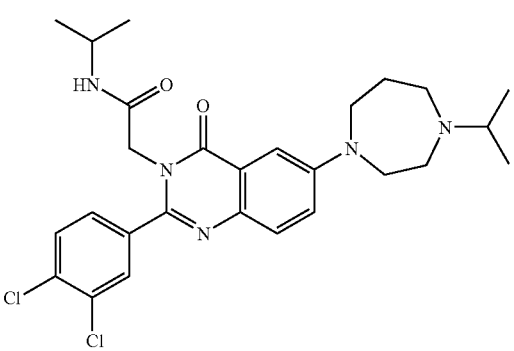

MS (ESI) m/z: 530/532/534 ([M+H]$^+$) (from INTERMEDIATE V.31).

Example 6Ao

2-[2-(3,4-Dimethylphenyl)-6-(4-isopropylperhydro-1,4-diazepin-1-yl)-4-oxo-4H-quinazolin-3-yl]-N-isopropylacetamide

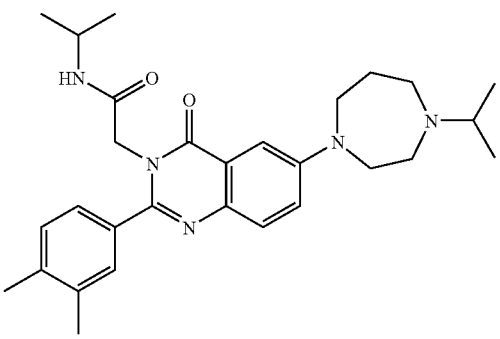

MS (ESI) m/z: 490 ([M+H]$^+$) (from INTERMEDIATE V.31).

Example 6Ap

2-[2-(3-Chloro-4-fluorophenyl)-6-((R)-3-isopropylpiperazin-1-yl)-4-oxo-4H-quinazolin-3-yl]-N-isopropylacetamide

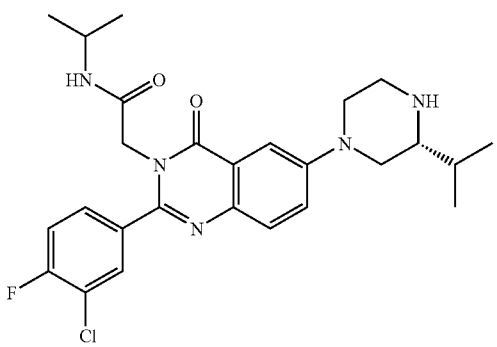

MS (ESI) m/z: 500/502 ([M+H]$^+$) (from INTERMEDIATE V.36).

Example 6Aq

2-[2-(3-Chloro-4-fluorophenyl)-6-((S)-3-isopropylpiperazin-1-yl)-4-oxo-4H-quinazolin-3-yl]-N-isopropylacetamide

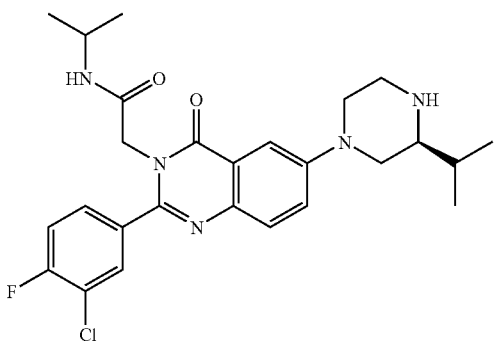

MS (ESI) m/z: 500/502 ([M+H]$^+$) (from INTERMEDIATE V.37).

Example 6Ar

N-Isopropyl-2-[6-(4-isopropyl perhydro-1,4-diazepin-1-yl)-2-(6-methylpyridin-2-yl)-4-oxo-4H-quinazolin-3-yl]acetamide

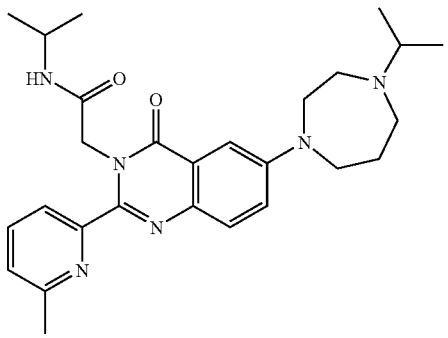

MS (ESI) m/z: 477 ([M+H]$^+$) (from INTERMEDIATE V.31).

Example 6As

2-[2-(2-Fluoro-4-trifluoromethylphenyl)-6-(4-isopropylperhydro-1,4-diazepin-1-yl)-4-oxo-4H-quinazolin-3-yl]-N-isopropylacetamide acetamide

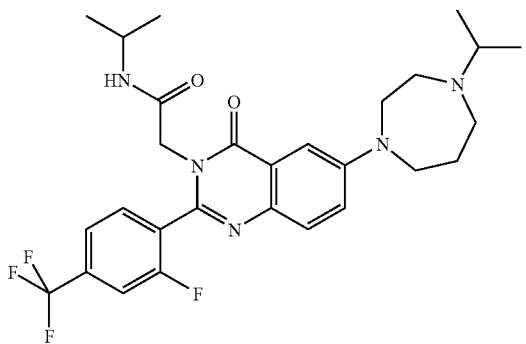

MS (ESI) m/z: 548 ([M+H]$^+$) (from INTERMEDIATE V.31).

Example 6At

2-[2-(3-Chlorophenyl)-6-(6,6-dimethylperhydro-1,4-diazepin-1-yl)-4-oxo-4H-quinazolin-3-yl]-N-isopropylacetamide

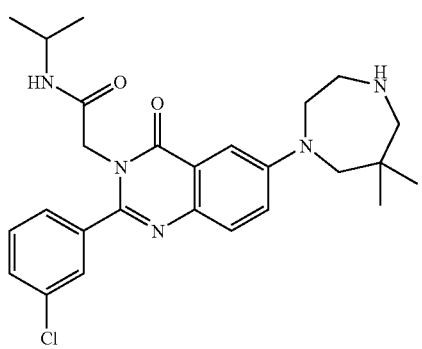

2-Amino-5-(6,6-dimethyl-1,4-diazepan-1-yl)-N-(2-(isopropylamino)-2-oxoethyl)benzamide (INTERMEDIATE V.54) (110 mg, 0.304 mmol), 3-chlorobenzaldehyde (58 mg, 0.365 mmol) and acetic acid (10 mg, 0.0003 mmol) were dissolved in ethanol (3 mL) and stirred at 90° C. for 16 h. The reaction mixture was evaporated to dryness, crude product dissolved in DCM (3 mL) and 4,5-dichloro-3,6-dioxocyclohexa-1,4-diene-1,2-dicarbonitrile (138 mg, 0.609 mmol) added. The reaction mixture was stirred at room temperature for 4 h. The crude mixture was dissolved in MeOH and purified by SCX eluting with 2N NH$_3$/MeOH. Solvent was evaporated under reduced pressure and the crude material purified by chromatography on silica gel with a gradient of DCM to DCM:MeOH (3:1, v/v) as eluent. This afforded 2-[2-(3-chlorophenyl)-6-(6,6-dimethylperhydro-1,4-diazepin-1-yl)-4-oxo-4H-quinazolin-3-yl]-N-isopropylacetamide (EXAMPLE 6At) (17 mg, 0.034 mmol, 11%).

Data for 2-[2-(3-chlorophenyl)-6-(6,6-dimethylperhydro-1,4-diazepin-1-yl)-4-oxo-4H-quinazolin-3-yl]-N-isopropylacetamide (EXAMPLE 6At): MS (ESI) m/z: 482/484 ([M+H]$^+$).

Example 6Au

2-[2-(4-Fluoro-3-methoxyphenyl)-4-oxo-6-(3-propylperhydro-1,4-diazepin-1-yl)-4H-quinazolin-3-yl]-N-isopropylacetamide

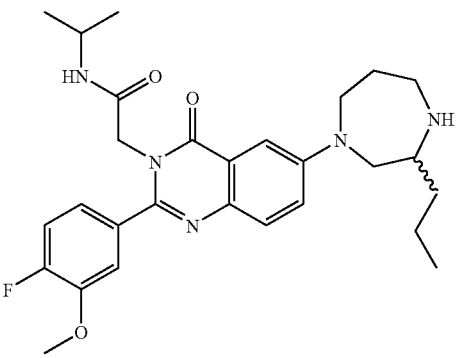

MS (ESI) m/z: 510 ([M+H]$^+$) (from INTERMEDIATE V.32).

Example 6Av

2-[2-(3-Chloro-4-fluorophenyl-4-oxo-6-(3-propylperhydro-1,4-diazepin-1-yl)-4H-quinazolin-3-yl]-N-isopropylacetamide

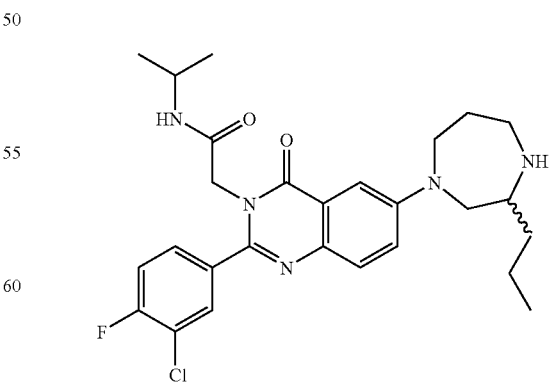

MS (ESI) m/z: 514/516 ([M+H]$^+$) (from INTERMEDIATE V.32).

Example 6Aw

2-[2-(3-Chlorophenyl)-4-oxo-6-(3-propylperhydro-1,4-diazepin-1-yl)-4H-quinazolin-3-yl]-N-isopropylacetamide

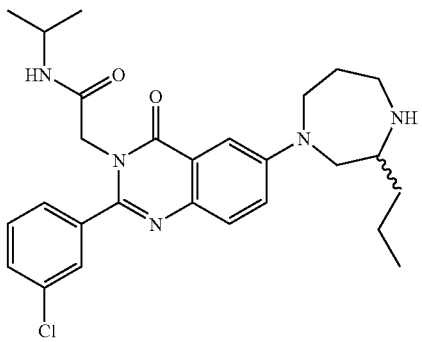

MS (ESI) m/z: 496/498 ([M+H]$^+$) (from INTERMEDIATE V.32).

Example 7a

N-tert-Butyl-2-(2-cyclopentyl-4-oxo-6-perhydro-1,4-diazepin-1-yl-4H-quinazolin-3-yl-acetamide

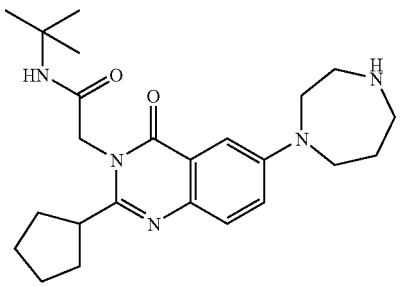

Pyridine (21 mg, 0.022 mL, 0.268 mmol) and cyclopentanecarbonyl chloride (30 mg, 0.223 mmol) were added to an ice-water cooled solution of 4-{4-amino-3-[(tert-butylcarbamoylmethyl)carbamoyl]phenyl}perhydro-1,4-diazepine-1-carboxylic acid tert-butyl ester (INTERMEDIATE V.38) (100 mg, 0.223 mmol) in THF (1 mL) and the reaction mixture stirred for 15 min. Solvent was removed in vacuo and the residue partitioned between DCM (10 mL) and water (10 mL). The organic phase was dried (Na$_2$SO$_4$) and concentrated in vacuo. The crude material was dissolved in 1,2-dichloroethane (5 mL) and triethylamine (1.04 g, 1.39 mL, 10.28 mmol) and trimethylsilyl chloride (364 mg, 0.428 mL, 3.35 mmol) added. The reaction mixture was heated at reflux temperature for 3 h. The reaction mixture was diluted with EtOAc (10 mL), washed with 1M HCl (aq.) and sodium bicarbonate (aq.) solution. The organic phase was dried (MgSO$_4$) and solvent removed in vacuo. Crude product was purified by chromatography on silica gel with a gradient of DCM to DCM:EtOAc (1:4, v/v) as eluent. The product was dissolved in DCM (5 mL), TFA (0.5 mL) added and the reaction stirred at room temperature for 2 h. The solution was poured directly onto an SCX cartridge and product eluted with 2N NH$_3$/MeOH. Solvent was removed under reduced pressure to afford N-tert-butyl-2-(2-cyclopentyl-4-oxo-6-perhydro-1,4-diazepin-1-yl-4H-quinazolin-3-yl-acetamide (EXAMPLE 7a) (35 mg, 0.082 mmol, 37%).

Data for N-tert-butyl-2-(2-cyclopentyl-4-oxo-6-perhydro-1,4-diazepin-1-yl-4H-quinazolin-3-yl-acetamide (EXAMPLE 7a): MS (ESI) m/z: 426 ([M+H]$^+$).

Similarly prepared from INTERMEDIATES V were:

Example 7b

N-tert-Butyl-2-(4-oxo-6-perhydro-1,4-diazepin-1-yl-2-phenyl-4H-quinazolin-3-yl)acetamide

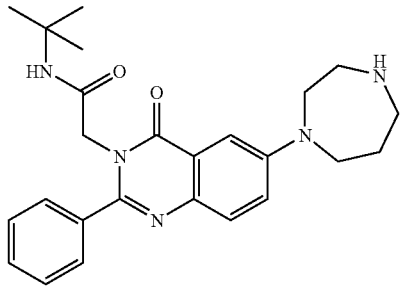

MS (ESI) m/z: 434 ([M+H]$^+$) (from INTERMEDIATE V.38).

Example 7c

N-tert-Butyl-2-[2-(3-fluorophenyl)-4-oxo-6-perhydro-1,4-diazepin-1-yl-4H-quinazolin-3-yl]acetamide

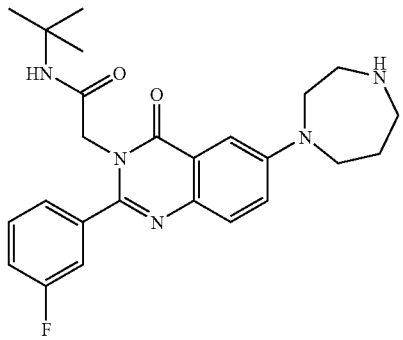

MS (ESI) m/z: 452 ([M+H]$^+$) (from INTERMEDIATE V.38).

Example 7d

N-tert-Butyl-2-[2-(3-fluorophenyl)-6-(4-isopropylperhydro-1,4-diazepin-1-yl)-4-oxo-4H-quinazolin-3-yl]acetamide

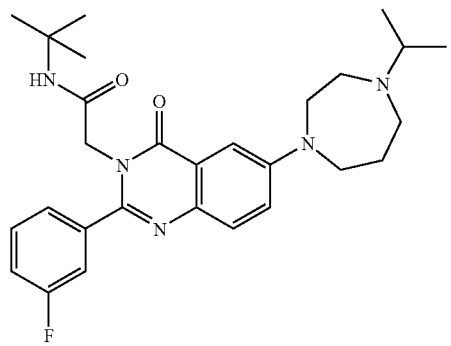

3-Fluorobenzoyl chloride (24 mg, 0.154 mmol, 0.019 mL) was added to an ice-water cooled solution of 2-amino-N-(tert-butylcarbamoylmethyl)-5-(4-isopropylperhydro-1,4-diazepin-1-yl)benzamide (INTERMEDIATE V.49) (60 mg, 0.154 mmol) and triethylamine (716 mg, 0.96 mL, 7.09 mmol) in DCM (2 mL). Stirring was continued for 15 min. Trimethylsilyl chloride (251 mg, 0.295 mL, 2.31 mmol) was added and the reaction mixture heated in the microwave at 150° C. for 7 min. The reaction mixture was diluted with DCM (10 mL) and washed with water. The organic phase was dried (MgSO$_4$) and concentrated in vacuo. Crude product was purified by chromatography on silica gel with a gradient of DCM to DCM:MeOH:NH$_3$ (95:4:1, v/v) as eluent. Further purification by preparative HPLC afforded N-tert-butyl-2-[2-(3-fluorophenyl)-6-(4-isopropylperhydro-1,4-diazepin-1-yl)-4-oxo-4H-quinazolin-3-yl]acetamide (EXAMPLE 7d) (5 mg, 10 μmol, 7%).

Data for N-tert-butyl-2-[2-(3-fluorophenyl)-6-(4-isopropylperhydro-1,4-diazepin-1-yl)-4-oxo-4H-quinazolin-3-yl]acetamide (EXAMPLE 7d): MS (ESI) m/z: 494 ([M+H]$^+$).

Example 7e

2-[2-(3-Fluorophenyl)-6-(4-isopropylperhydro-1,4-diazepin-1-yl)-4-oxo-4H-quinazolin-3-yl]-N-isopropylacetamide

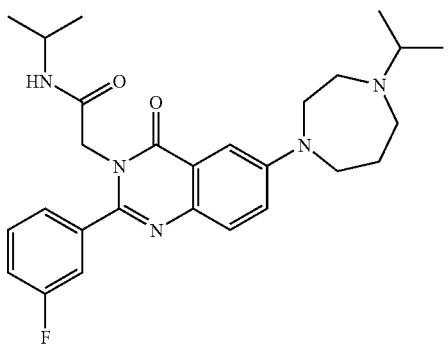

MS (ESI) m/z: 480 ([M+H]$^+$) (from INTERMEDIATE V.31).

Example 7f

2-[2-Cyclopentyl-6-(4-isopropylperhydro-1,4-diazepin-1-yl)-4-oxo-4H-quinazolin-3-yl]-N-isopropylacetamide

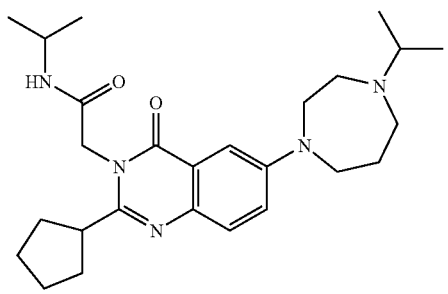

MS (ESI) m/z: 454 ([M+H]$^+$) (from INTERMEDIATE V.31).

Example 7g

2-[2-(2-Fluorophenyl)-6-(4-isopropylperhydro-1,4-diazepin-1-yl)-4-oxo-4H-quinazolin-3-yl]-N-isopropylacetamide

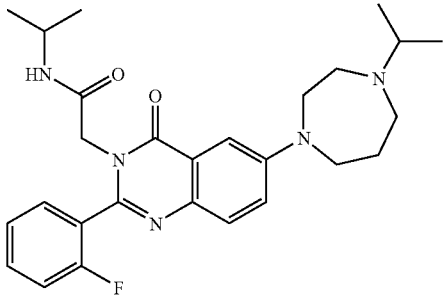

MS (ESI) m/z: 480 ([M+H]$^+$) (from INTERMEDIATE V.31).

Example 7h

2-[2-(3,4-Difluorophenyl)-6-(4-isopropylperhydro-1,4-diazepin-1-yl)-4-oxo-4H-quinazolin-3-yl]-N-isopropylacetamide

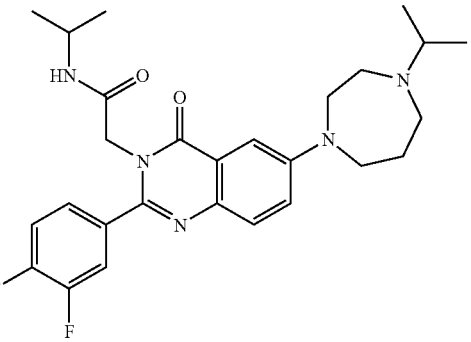

MS (ESI) m/z: 498 ([M+H]$^+$) (from INTERMEDIATE V.31).

Example 7i

2-[2-(4-Fluorophenyl)-6-(4-isopropylperhydro-1,4-diazepin-1-yl)-4-oxo-4H-quinazolin-3-yl]-N-isopropylacetamide

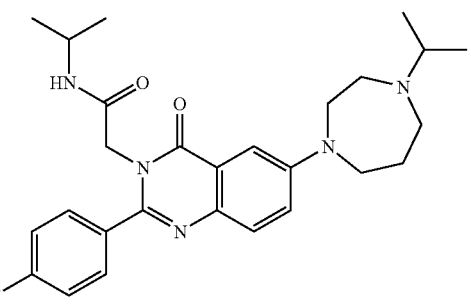

MS (ESI) m/z: 480 ([M+H]$^+$) (from INTERMEDIATE V.31).

Example 7j

N-Isopropyl-2-[6-(4-isopropylperhydro-1,4-diazepin-1-yl)-4-oxo-2-thiophen-2-yl-4H-quinazolin-3-yl]acetamide

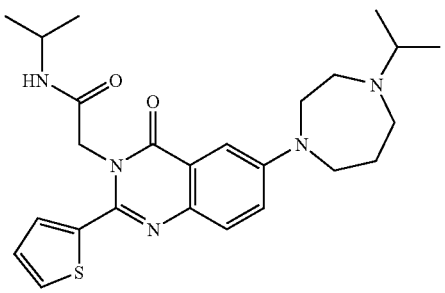

MS (ESI) m/z: 468 ([M+H]$^+$) (from INTERMEDIATE V.31).

Example 8a

2-[2-(4-Fluoro-3-methoxyphenyl)-4-oxo-6-(3,6,6-trimethylperhydro-1,4-diazepan-1-yl)-4H-quinazolin-3-yl]-N-isopropylacetamide

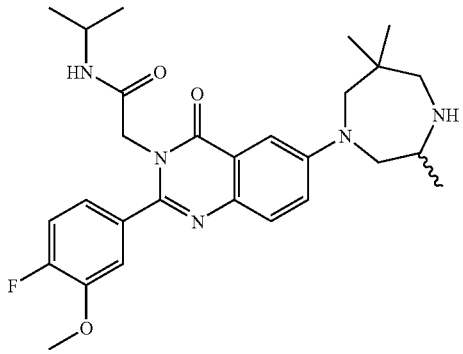

a) 4-[3-Carboxymethyl-2-(4-fluoro-3-methoxyphenyl)-4-oxo-3,4-dihydroquinazolin-6-yl]-2,6,6-trimethylperhydro-1,4-diazepine-1-carboxylic acid tert-butyl ester

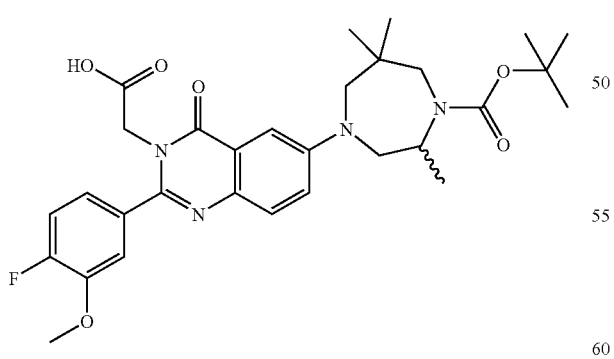

[2-(4-Fluoro-3-methoxyphenyl)-4-oxo-6-(3,6,6-trimethylperhydro-1,4-diazepin-1-yl)-4H-quinazolin-3-yl]acetic acid (INTERMEDIATE IX.1) (160 mg, 0.341 mmol), di-tert-butyldicarbonate (78 mg, 0.359 mmol) and triethylamine (76 mg, 0.751 mmol) were combined and stirred at room temperature in DCM (5 mL) overnight. The crude product mixture was washed with 1N HCl (2×20 mL) and water (40 mL). The organic phase was dried (Na$_2$SO$_4$) and concentrated in vacuo. Crude product was purified by chromatography on silica gel with DCM:MeOH (3:1, v/v) as eluent to afford 4-[3-carboxymethyl-2-(4-fluoro-3-methoxyphenyl)-4-oxo-3,4-dihydroquinazolin-6-yl]-2,6,6-trimethylperhydro-1,4-diazepine-1-carboxylic acid tert-butyl ester (200 mg, 0.352 mmol, 100%).

b) 4-[2-(4-Fluoro-3-methoxyphenyl)-3-(isopropylcarbamoylmethyl)-4-oxo-3,4-dihydroquinazolin-6-yl]-2,6,6-trimethylperhydro-1,4-diazepine-1-carboxylic acid tert-butyl ester

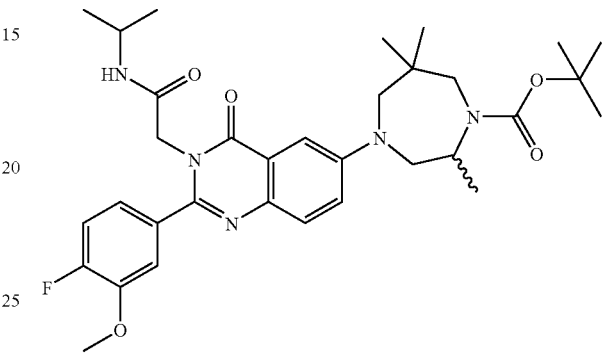

4-[3-Carboxymethyl-2-(4-fluoro-3-methoxyphenyl)-4-oxo-3,4-dihydroquinazolin-6-yl]-2,6,6-trimethylperhydro-1,4-diazepine-1-carboxylic acid tert-butyl ester (200 mg, 0.352 mmol), isopropylamine (208 mg, 299 uL, 3.52 mmol), 1-propanephosphonic acid cyclic anhydride (336 mg, 320 uL, 0.528 mmol) and DIPEA (135 mg, 186 uL, 1.06 mmol) were stirred at room temperature in DCM (15 mL) for 2 h. NaHCO$_3$ (aq.) (15 mL) was added, the organic layer separated, dried (Na$_2$SO$_4$) and evaporated under reduced pressure. Crude product was purified by chromatography on silica gel with a gradient of DCM to DCM:MeOH (4:1, v/v) as eluent to afford 4-[2-(4-fluoro-3-methoxyphenyl)-3-(isopropylcarbamoylmethyl)-4-oxo-3,4-dihydroquinazolin-6-yl]-2,6,6-trimethylperhydro-1,4-diazepine-1-carboxylic acid tert-butyl ester (120 mg, 0.197 mmol, 56%).

c) 2-[2-(4-Fluoro-3-methoxyphenyl)-4-oxo-6-(3,6,6-trimethylperhydro-1,4-diazepin-1-yl)-4H-quinazolin-3-yl]-N-isopropylacetamide 4-[2-(4-Fluoro-3-methoxyphenyl)-3-(isopropylcarbamoylmethyl)-4-oxo-3,4-dihydroquinazolin-6-yl]-2,6,6-trimethylperhydro-1,4-diazepine-1-carboxylic acid tert-butyl ester (120 mg, 0.197 mmol) was dissolved in DCM (6 mL) and TFA (3 mL) added. The reaction was stirred at room temperature for 4 h. Product mixture was poured directly onto an SCX cartridge and product eluted with 2N NH$_3$/MeOH. Solvent was evaporated under reduced pressure to afford a red solid. Product was diluted with MeOH (20 mL) and heated at reflux temperature with activated carbon. The mixture was filtered through a celite pad, solvent evaporated under reduced pressure and the resultant product recrystallised from ethanol:heptane. This afforded 2-[2-(4-fluoro-3-methoxyphenyl)-4-oxo-6-(3,6,6-trimethylperhydro-1,4-diazepin-1-yl)-4H-quinazolin-3-yl]-N-isopropylacetamide (EXAMPLE 8a) (74 mg, 0.145 mmol, 74%). Data for 2-[2-(4-fluoro-3-methoxyphenyl)-4-oxo-6-(3,6,6-trimethylperhydro-1,4-diazepin-1-yl)-4H-quinazolin-3-yl]-N-isopropylacetamide (EXAMPLE 8a): MS (ESI) m/z: 510 ([M+H]$^+$).

Similarly prepared were:

Example 8b

2-[6-(3-Ethyl-6,6-dimethylperhydro-1,4-diazepin-1-yl)-2-(4-fluoro-3-methoxyphenyl)-4-oxo-4H-quinazolin-3-yl]-N-isopropylacetamide

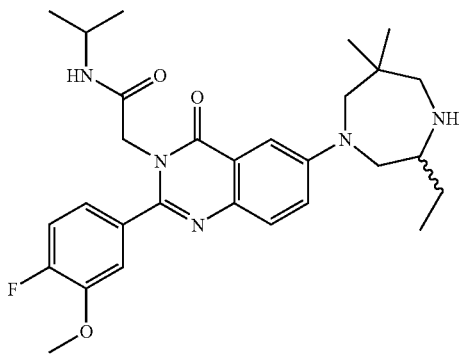

MS (ESI) m/z: 524 ([M+H]$^+$) (from INTERMEDIATE IX.3).

Example 8c

2-[2-(4-Fluoro-3-methoxyphenyl)-6-((S)-3-isopropyl-6,6-dimethylperhydro-1,4-diazepin-1-yl)-4-oxo-4H-quinazolin-3-yl]-N-isopropylacetamide

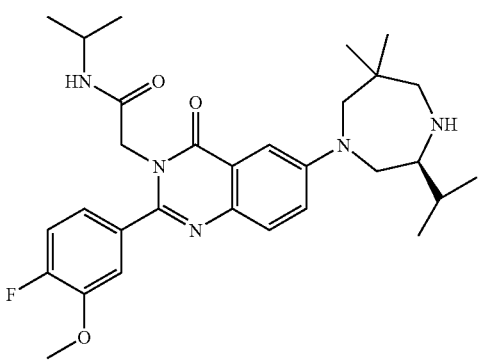

MS (ESI) m/z: 538 ([M+H]$^+$) (from INTERMEDIATE IX.6).

Example 8d

2-[2-(3-Chloro-4-fluorophenyl)-6-(dimethylperhydro-1,4-diazepin-1-yl)-4-oxo-4H-quinazolin-3-yl]-N—((S)-2,2,2-trifluoro-1-methylethyl)acetamide

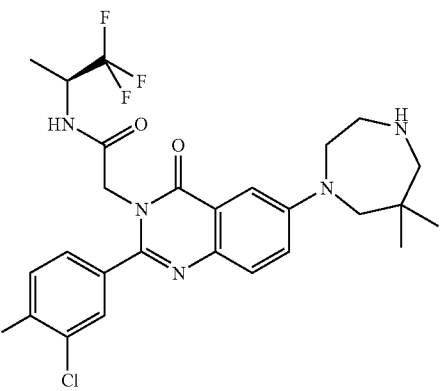

MS (ESI) m/z: 554 ([M+H]$^+$) (from INTERMEDIATE IX.4).

Example 8e

2-[2-(3-Chloro-4-fluorophenyl)-6-(dimethylperhydro-1,4-diazepin-1-yl)-4-oxo-4H-quinazolin-3-yl]-N—((R)-2,2,2-trifluoro-1-methylethyl)acetamide

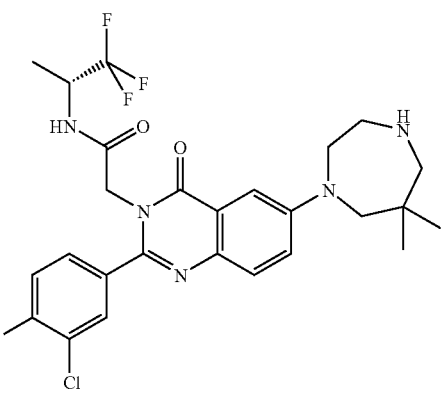

MS (ESI) m/z: 554 ([M+H]$^+$) (from INTERMEDIATE IX.4).

Example 8f

N-tert-Butyl-2-[2-(3-chloro-4-fluorophenyl)-6-(dimethylperhydro-1,4-diazepin-1-yl)-4-oxo-4H-quinazolin-3-yl]acetamide

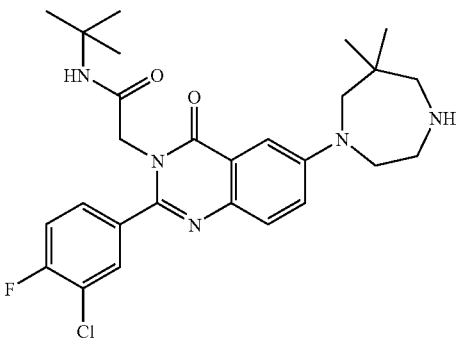

MS (ESI) m/z: 514 ([M+H]$^+$) (from INTERMEDIATE IX.4).

Example 8g

2-[6-(6,6-Dimethyl-3-propylperhydro-1,4-diazepin-1-yl)-2-(4-fluoro-3-methoxyphenyl)-4-oxo-4H-quinazolin-3-yl]-N-isopropylacetamide

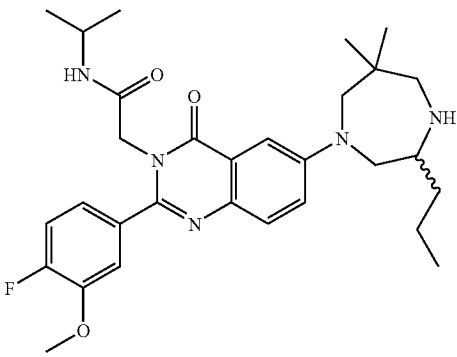

MS (ESI) m/z: 538 ([M+H]$^+$) (from INTERMEDIATE IX.5).

Example 9a

N-tert-Butyl-2-[6-(1,4-diazabicyclo[3.2.2]non-4-yl)-2-(4-fluoro-3-methoxyphenyl)-4-oxo-4H-quinazolin-3-yl]acetamide

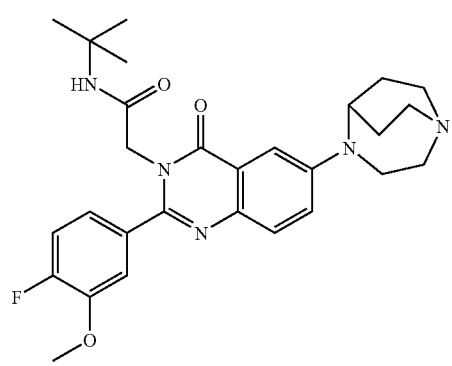

[6-(1,4-Diazabicyclo[3.2.2]non-4-yl)-2-(4-fluoro-3-methoxyphenyl)-4-oxo-4H-quinazolin-3-yl]acetic acid (INTERMEDIATE IX.7) (20 mg, 0.44 mmol) was dissolved in DCM (5 mL). Tert-butylamine (6.5 mg, 0.088 mmol) and N,N-diisopropylethylamine (7 mg, 0.053 mmol) were added followed by 1-propanephosphonic acid cyclic anhydride (21 mg, 0.02 mL, 0.066 mmol). The reaction mixture was stirred at room temperature for 12 h. Methanol (5 mL) was added and the solution poured directly onto an SCX cartridge. Elution with 2N NH$_3$/MeOH followed further purification by preparative HPLC afforded N-tert-butyl-2-[6-(1,4-diazabicyclo[3.2.2]non-4-yl)-2-(4-fluoro-3-methoxyphenyl)-4-oxo-4H-quinazolin-3-yl]acetamide (EXAMPLE 9a) (7.3 mg, 0.014 mmol, 33%).

Data for N-tert-butyl-2-[6-(1,4-diazabicyclo[3.2.2]non-4-yl)-2-(4-fluoro-3-methoxyphenyl)-4-oxo-4H-quinazolin-3-yl]acetamide (EXAMPLE 9a): MS (ESI) m/z: 508 ([M+H]$^+$).

Similarly prepared were:

Example 9b

2-[2-(3-Chloro-4-fluorophenyl)-6-((R)-3-methylpiperazin-1-yl)-4-oxo-4H-quinazolin-3-yl]-N-(2,2,2-trifluoro-1,1-dimethylethyl)acetamide

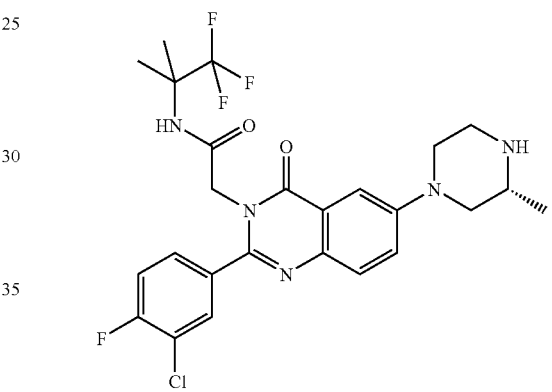

MS (ESI) m/z: 540/542 ([M+H]$^+$) (from INTERMEDIATE IX.8).

Example 9c

2-[2-(3-Chloro-4-fluorophenyl)-6-(hexahydropyrrolo[1,2-a]pyrazin-2-yl)-4-oxo-4H-quinazolin-3-yl]-N—((R)-2,2,2-trifluoro-1-methylethyl)acetamide

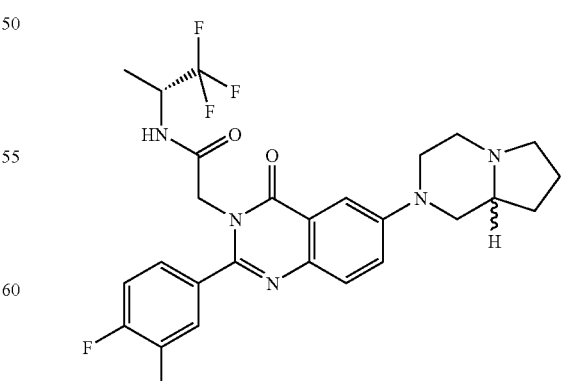

MS (ESI) m/z: 552/554 ([M+H]$^+$) (from INTERMEDIATE IX.9).

Example 9d

2-[2-(3-Chloro-4-fluorophenyl)-6-(hexahydropyrrolo[1,2-a]pyrazin-2-yl)-4-oxo-4H-quinazolin-3-yl]-N—((S)-2,2,2-trifluoro-1-methylethyl)acetamide

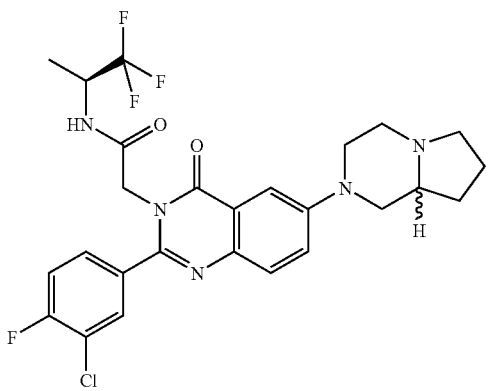

MS (ESI) m/z: 552/554 ([M+H]$^+$) (from INTERMEDIATE IX.9).

Example 9e

2-[2-(3-Chloro-4-fluorophenyl)-6-(4-isopropylperhydro-1,4-diazepin-1-yl)-4-oxo-4H-quinazolin-3-yl]-N-(2,2,2-trifluoro-1,1-dimethylethyl)acetamide

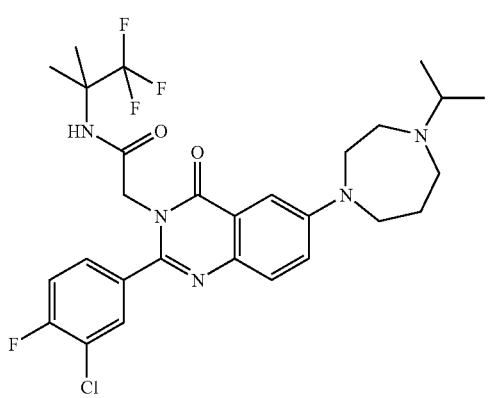

MS (ESI) m/z: 582/584 ([M+H]$^+$) (from INTERMEDIATE IX.10).

Example 9f

2-[2-(3-Chloro-4-fluorophenyl)-6-(4-isopropylperhydro-1,4-diazepin-1-yl)-4-oxo-4H-quinazolin-3-yl]-N-(2,2,2-trifluoro-1-methylethyl)acetamide

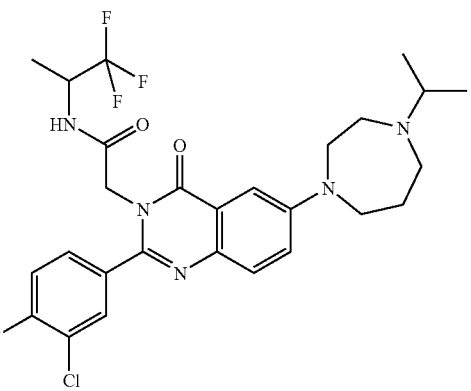

MS (ESI) m/z: 568 ([M+H]$^+$) (from INTERMEDIATE IX.10).

Example 9g

2-[2-(3-Chloro-4-fluorophenyl)-6-(4-isopropylperhydro-1,4-diazepin-1-yl)-4-oxo-4H-quinazolin-3-yl]-N-isobutylacetamide

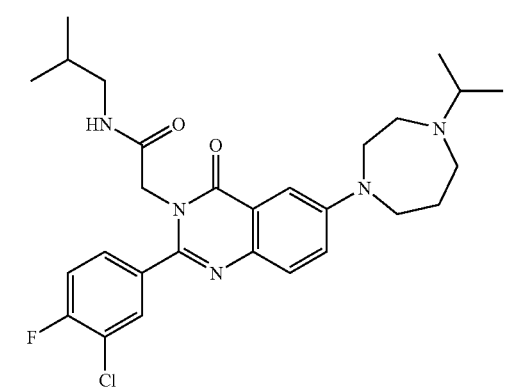

MS (ESI) m/z: 528 ([M+H]$^+$) (from INTERMEDIATE IX.10).

Example 9h

2-[6-(4-Ethylperhydro-1,4-diazepin-1-yl)-2-(4-fluoro-3-methoxyphenyl)-4-oxo-4H-quinazolin-3-yl]-N-(2,212-trifluoro-1,1-dimethylethyl)acetamide

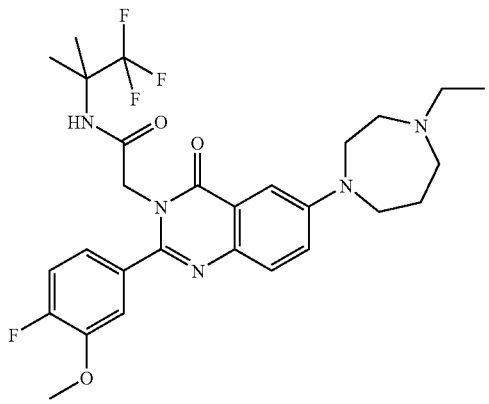

MS (ESI) m/z: 564 ([M+H]$^+$) (from INTERMEDIATE IX.11).

Example 9i

2-[6-(4-Ethylperhydro-1,4-diazepin-1-yl)-2-(4-fluoro-3-methoxyphenyl)-4-oxo-4H-quinazolin-3-yl]-N—((S)-2,2,2-trifluoro-1-methylethyl)acetamide

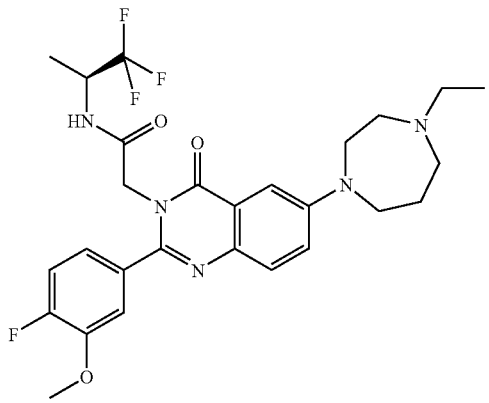

MS (ESI) m/z: 550 ([M+H]$^+$) (from INTERMEDIATE IX.11).

Example 9j

2-[6-(4-Ethylperhydro-1,4-diazepin-1-yl)-2-(4-fluoro-3-methoxyphenyl)-4-oxo-4H-quinazolin-3-yl]-N—((R)-2,2,2-trifluoro-1-methylethyl)acetamide

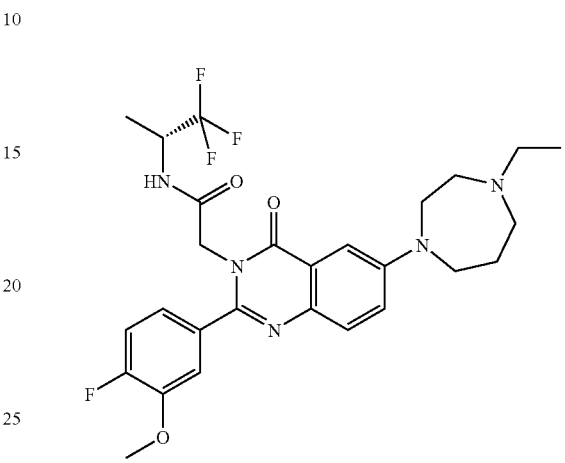

MS (ESI) m/z: 550 ([M+H]$^+$) (from INTERMEDIATE IX.11).

Example 9k

N-Cyclobutyl-2-[6-(4-ethylperhydro-1,4-diazepin-1-yl)-2-(4-fluoro-3-methoxyphenyl)-4-oxo-4H-quinazolin-3-yl]acetamide

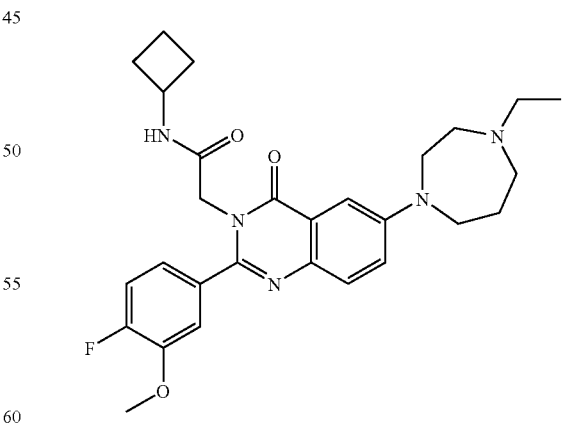

MS (ESI) m/z: 508 ([M+H]$^+$) (from INTERMEDIATE IX.11).

Example 9l

2-[6-(4-Ethylperhydro-1,4-diazepin-1-yl)-2-(4-fluoro-3-methoxyphenyl)-4-oxo-4H-quinazolin-3-yl]-N-isobutylacetamide

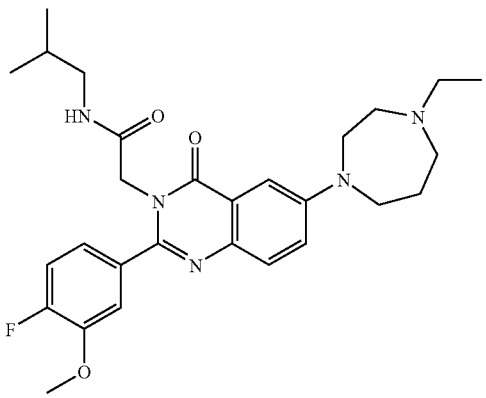

MS (ESI) m/z: 510 ([M+H]$^+$) (from INTERMEDIATE IX.11).

Example 9m

2-[2-(3-Chloro-4-fluorophenyl)-6-(4-ethylperhydro-1,4-diazepin-1-yl)-4-oxo-4H-quinazolin-3-yl]-N—((S)-2,2,2-trifluoro-1-methylethyl)acetamide

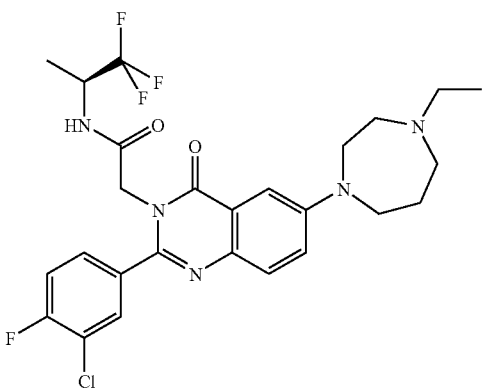

MS (ESI) m/z: 554/556 ([M+H]$^+$) (from INTERMEDIATE IX.12).

Example 9n

2-[2-(3-Chloro-4-fluorophenyl)-6-(4-ethylperhydro-1,4-diazepin-1-yl)-4-oxo-4H-quinazolin-3-yl]-N—((R)-2,2,2-trifluoro-1-methylethyl)acetamide

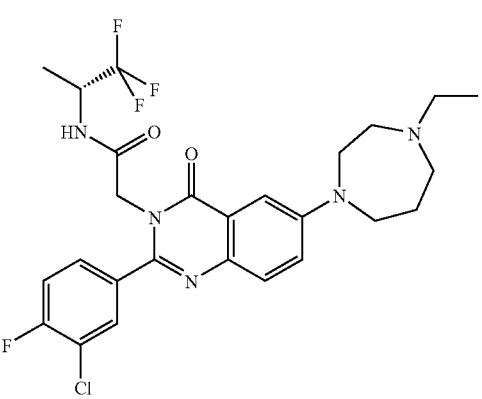

MS (ESI) m/z: 554 ([M+H]$^+$) (from INTERMEDIATE IX.12).

Example 9o

2-[2-(3-Chloro-4-fluorophenyl)-6-(4-ethyl-perhydro-1,4-diazepin-1-yl)-4-oxo-4H-quinazolin-3-yl]-N-cyclobutylacetamide

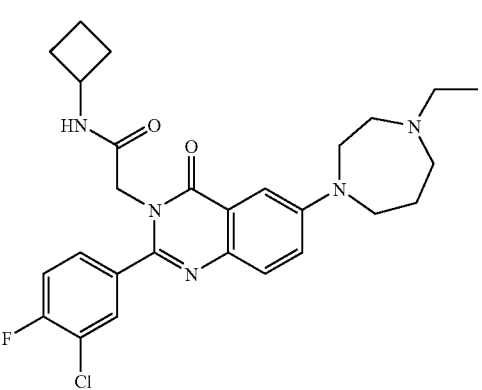

MS (ESI) m/z: 512/514 ([M+H]$^+$) (from INTERMEDIATE IX.12).

Example 9p

2-[2-(3-Chloro-4-fluorophenyl)-6-(4-ethylperhydro-1,4-diazepin-1-yl)-4-oxo-4H-quinazolin-3-yl]-N-isobutylacetamide

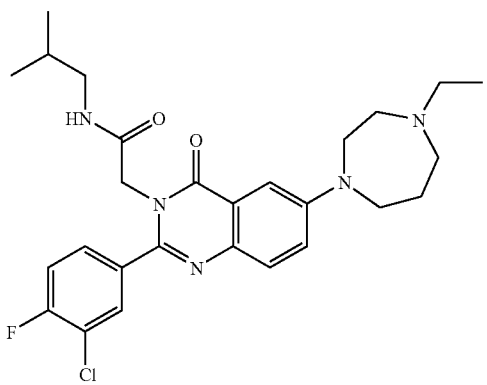

MS (ESI) m/z: 514/516 ([M+H]$^+$) (from INTERMEDIATE IX.12).

Example 9q

2-{2-(4-Fluoro-3-methoxyphenyl)-6-[4-(2-hydroxyethyl)perhydro-1,4-diazepin-1-yl]-4-oxo-4H-quinazolin-3-yl}-N—((S)-2,2,2-trifluoro-1-methylethyl)acetamide

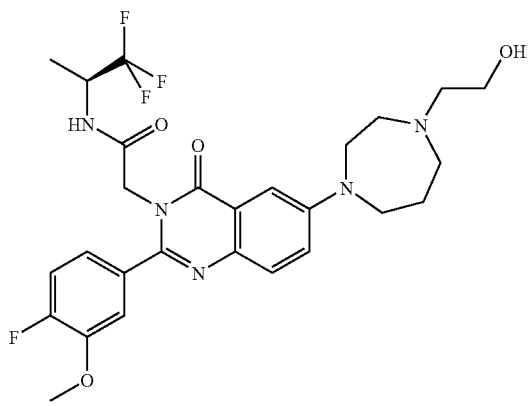

MS (ESI) m/z: 566 ([M+H]$^+$) (from INTERMEDIATE IX.13).

Example 9r

2-{2-(4-Fluoro-3-methoxyphenyl)-6-[4-(2-hydroxyethyl)perhydro-1,4-diazepin-1-yl]-4-oxo-4H-quinazolin-3-yl}-N—((R)-2,2,2-trifluoro-1-methylethyl)acetamide

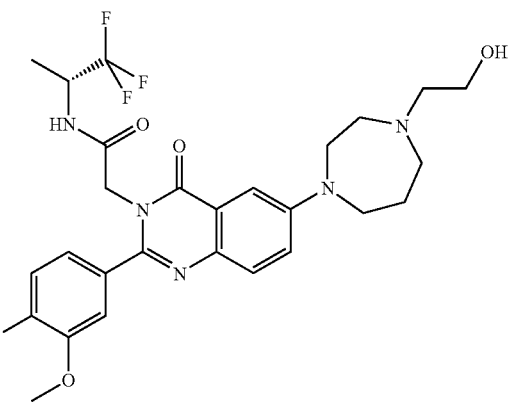

MS (ESI) m/z: 566 ([M+H]$^+$) (from INTERMEDIATE IX.13).

Example 9s

N-Cyclobutyl-2-[2-(4-fluoro-3-methoxyphenyl)-6-[4-(2-hydroxyethyl)perhydro-1,4-diazepin-1-yl]-4-oxo-4H-quinazolin-3-yl]acetamide

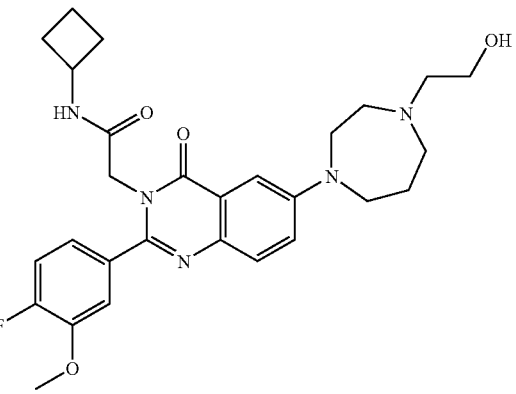

MS (ESI) m/z: 524 ([M+H]$^+$) (from INTERMEDIATE IX.13).

Example 9t

2-[2-(4-Fluoro-3-methoxyphenyl)-6-[4-(2-hydroxyethyl)perhydro-1,4-diazepin-1-yl]-4-oxo-4H-quinazolin-3-yl]-N-isobutylacetamide

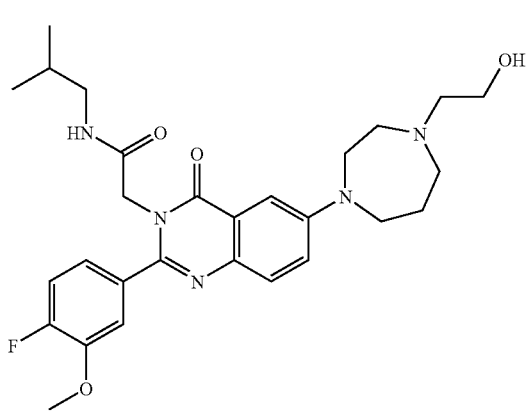

MS (ESI) m/z: 526 ([M+H]+) (from INTERMEDIATE IX.13).

Example 9u

2-[2-(3-Chlorophenyl)-6-(4-isopropylperhydro-1,4-diazepin-1-yl)-4-oxo-4H-quinazolin-3-yl]-N-isopropyl-N-methylacetamide

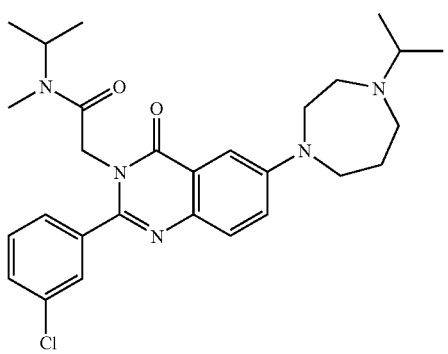

MS (ESI) m/z: 510/512 ([M+H]+) (from INTERMEDIATE IX.14).

Example 9v

2-[2-(3-Chlorophenyl)-6-(4-isopropylperhydro-1,4-diazepin-1-yl)-4-oxo-4H-quinazolin-3-yl]-N-ethylacetamide

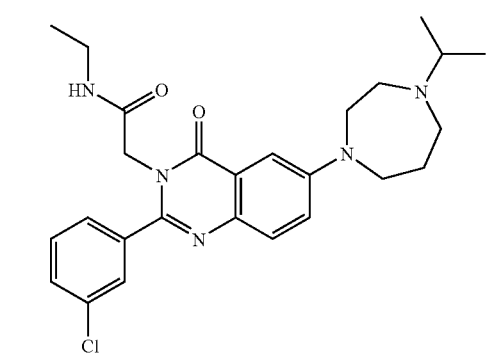

MS (ESI) m/z: 482/484 ([M+H]+) (from INTERMEDIATE IX.14).

Example 9w

2-[2-(3-Chlorophenyl)-6-(4-isopropylperhydro-1,4-diazepin-1-yl)-4-oxo-4H-quinazolin-3-yl]-N-cyclobutylacetamide

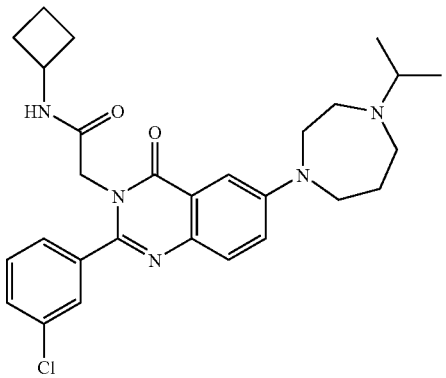

MS (ESI) m/z: 508/510 ([M+H]+) (from INTERMEDIATE IX.14).

Example 9x

2-[2-(3-Chlorophenyl)-6-(4-isopropylperhydro-1,4-diazepin-1-yl)-4-oxo-4H-quinazolin-3-yl]-N-(2,2,2-trifluoro-1-methylethyl)acetamide

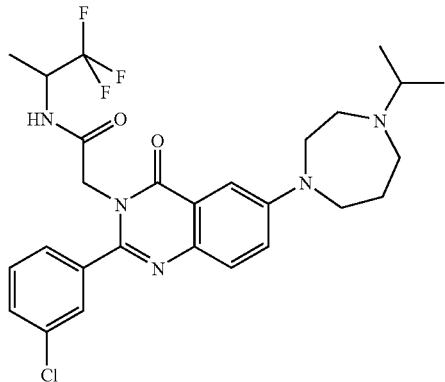

MS (ESI) m/z: 550/552 ([M+H]⁺) (from INTERMEDIATE IX.14).

Example 9y

2-[2-(3-Chlorophenyl)-6-(4-isopropylperhydro-1,4-diazepin-1-yl)-4-oxo-4H-quinazolin-3-yl]-N-isobutylacetamide

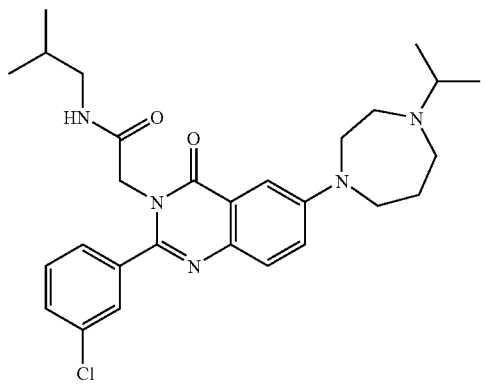

MS (ESI) m/z: 510/512 ([M+H]⁺) (from INTERMEDIATE IX.14).

Example 9z

2-[2-(3-Chlorophenyl)-6-(4-isopropylperhydro-1,4-diazepin-1-yl)-4-oxo-4H-quinazolin-3-yl]-N-(2,2,2-trifluoro-1,1-dimethylethyl)acetamide

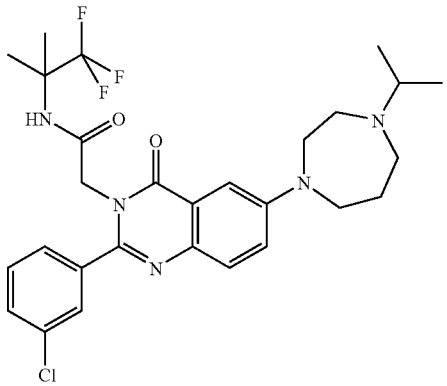

MS (ESI) m/z: 564/566 ([M+H]⁺) (from INTERMEDIATE IX.14).

Example 9Aa

2-[2-(3-Chloro-4-fluorophenyl)-6-((R)-3-methylpiperazin-1-yl)-4-oxo-4H-quinazolin-3-yl]-N-isopropylacetamide

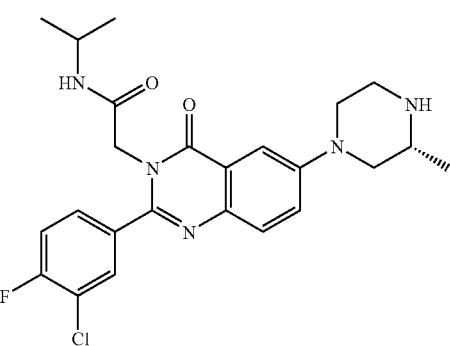

MS (ESI) m/z: 472/474 ([M+H]⁺) (from INTERMEDIATE IX.8).

Example 9Ab

2-[2-(3-Chloro-4-fluorophenyl)-6-(1,4-diazabicyclo[3.2.2]non-4-yl)-4-oxo-4H-quinazolin-3-yl]-N-isopropylacetamide

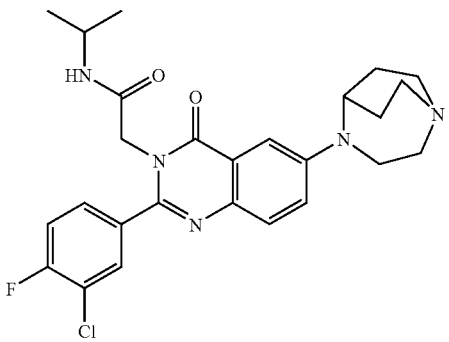

MS (ESI) m/z: 498/500 ([M+H]$^+$) (from INTERMEDIATE IX.15).

Example 9Ac

2-[6-(1,4-Diazabicyclo[3.2.2]non-4-yl)-2-(4-fluoro-3-methoxyphenyl)-4-oxo-4H-quinazolin-3-yl]-N-isopropylacetamide

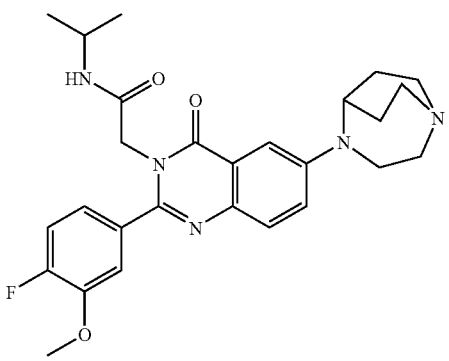

MS (ESI) m/z: 494 ([M+H]$^+$) (from INTERMEDIATE IX.7).

Example 9Ad

2-[6-(1,4-Diazabicyclo[3.2.2]non-4-yl)-2-(4-fluoro-3-methoxyphenyl)-4-oxo-4H-quinazolin-3-yl]-N-isobutylacetamide

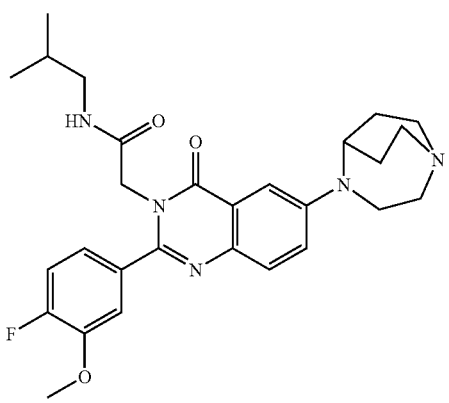

MS (ESI) m/z: 508 ([M+H]$^+$) (from INTERMEDIATE IX.7).

Example 9Ae

N—((R)-sec-Butyl)-2-[6-(1,4-diazabicyclo[3.2.2]non-4-yl)-2-(4-fluoro-3-methoxyphenyl)-4-oxo-4H-quinazolin-3-yl]acetamide

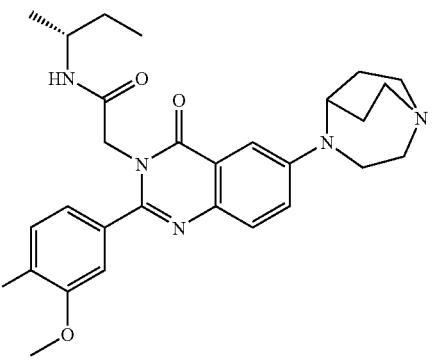

MS (ESI) m/z: 508 ([M+H]$^+$) (from INTERMEDIATE IX.7).

Example 9Af

2-[6-(1,4-Diazabicyclo[3.2.2]non-4-yl)-2-(4-fluoro-3-methoxyphenyl)-4-oxo-4H-quinazolin-3-yl]-N-(1-trifluoromethylpropyl)acetamide

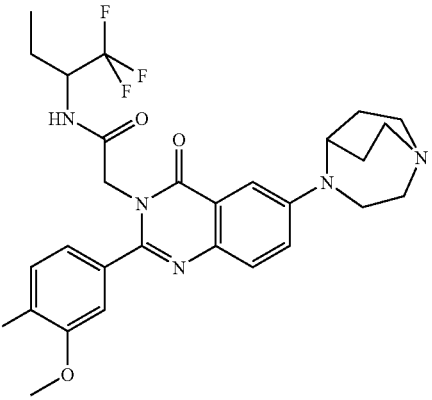

MS (ESI) m/z: 562 ([M+H]$^+$) (from INTERMEDIATE IX.7).

Example 9Ag

2-[6-(1,4-Diazabicyclo[3.2.2]non-4-yl)-2-(4-fluoro-3-methoxyphenyl)-4-oxo-4H-quinazolin-3-yl]-N-(2,2,2-trifluoro-1,1-dimethylethyl)acetamide

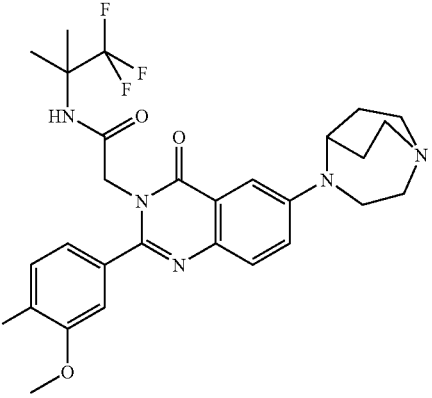

MS (ESI) m/z: 562 ([M+H]$^+$) (from INTERMEDIATE IX.7).

Example 9Ah

2-[6-(1,4-Diazabicyclo[3.2.2]non-4-yl)-2-(4-fluoro-3-methoxyphenyl)-4-oxo-4H-quinazolin-3-yl]-N-(2-methoxy-1-methylethyl)acetamide

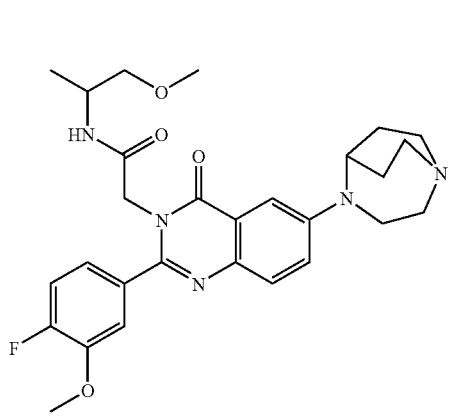

MS (ESI) m/z: 524 ([M+H]⁺) (from INTERMEDIATE IX.7).

Example 9Ai

N-(Cyanodimethyl-methyl)-2-[6-(1,4-diazabicyclo[3.2.2]non-4-yl)-2-(4-fluoro-3-methoxyphenyl)-4-oxo-4H-quinazolin-3-yl]acetamide

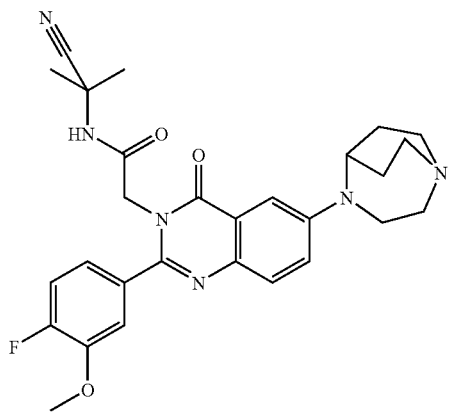

MS (ESI) m/z: 519 ([M+H]⁺) (from INTERMEDIATE IX.7).

Example 9Aj

N-Cyclopropylmethyl-2-[6-(1,4-diazabicyclo[3.2.2]non-4-yl)-2-(4-fluoro-3-methoxyphenyl)-4-oxo-4H-quinazolin-3-yl]acetamide

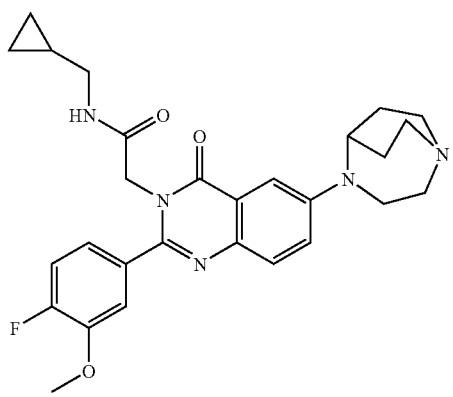

MS (ESI) m/z: 506 ([M+H]⁺) (from INTERMEDIATE IX.7).

Example 9Ak

2-[6-(1,4-Diazabicyclo[3.2.2]non-4-yl)-2-(3,5-dimethoxyphenyl)-4-oxo-4H-quinazolin-3-yl]-N-isopropylacetamide

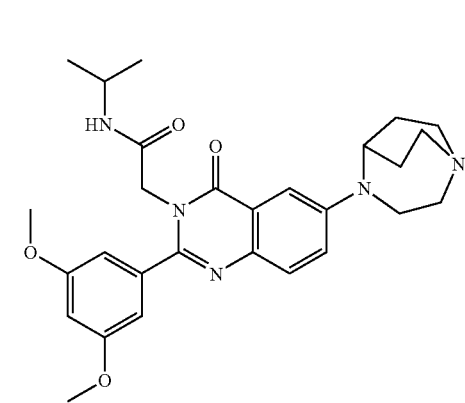

MS (ESI) m/z: 506 ([M+H]⁺) (from INTERMEDIATE IX.2).

Example 10a

2-[6-(4-Cyclopropylperhydro-1,4-diazepin-1-yl)-2-(4-fluoro-3-methoxyphenyl)-4-oxo-4H-quinazolin-3-yl]-N-isopropylacetamide

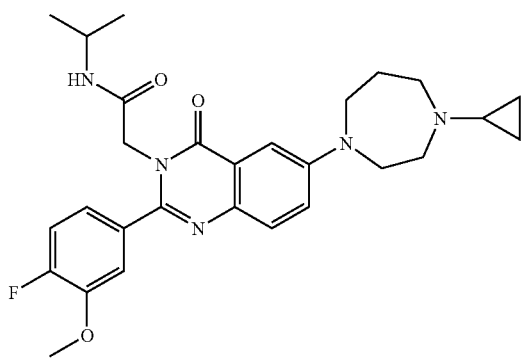

2-(6-(1,4-Diazepan-1-yl)-2-(4-fluoro-3-methoxyphenyl)-4-oxoquinazolin-3(4H)-yl)-N-isopropylacetamide (EXAMPLE 1i) (50 mg, 0.107 mmol), macroporous triethylammonium methylpolystyrene cyanoborohydride (70 mg, 0.107 mmol), acetonitrile (1.5 mL) and AcOH (0.3 mL) were combined under a nitrogen atmosphere. (1-Ethoxycyclopropoxy)trimethylsilane (19 mg, 0.04 mL, 0.107 mmol) was added and the reaction mixture stirred at room temperature for 48 h. Solvent was evaporated under reduced pressure. The residue was dissolved in 2M NH₃/MeOH and purified by preparative HPLC. This afforded 2-[6-(4-cyclopropylperhydro-1,4-diazepin-1-yl)-2-(4-fluoro-3-methoxyphenyl)-4-oxo-4H-quinazolin-3-yl]-N-isopropylacetamide (EXAMPLE 10a) (3 mg, 0.0039 mmol, 6%).

Data for 2-[6-(4-cyclopropylperhydro-1,4-diazepin-1-yl)-2-(4-fluoro-3-methoxyphenyl)-4-oxo-4H-quinazolin-3-yl]-N-isopropylacetamide (EXAMPLE 10a): MS (ESI) m/z: 508 ([M+H]⁺).

Similarly prepared were:

Example 10b

2-[2-(3-Chloro-4-fluorophenyl)-6-(4-cyclopropylperhydro-1,4-diazepin-1-yl)-4-oxo-4H-quinazolin-3-yl]-N-isopropylacetamide

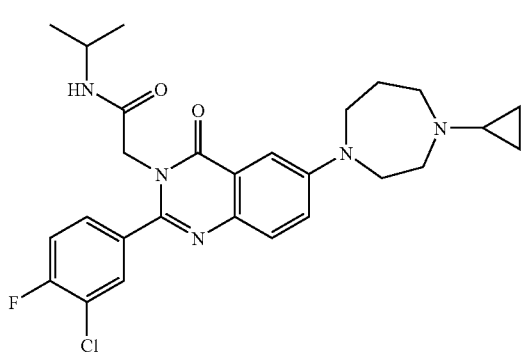

MS (ESI) m/z: 512/514 ([M+H]⁺) (from EXAMPLE 1e).

Example 10c

2-[2-(3-Chlorophenyl)-6-(4-cyclopropylperhydro-1,4-diazepin-1-yl)-4-oxo-4H-quinazolin-3-yl]-N-isopropylacetamide

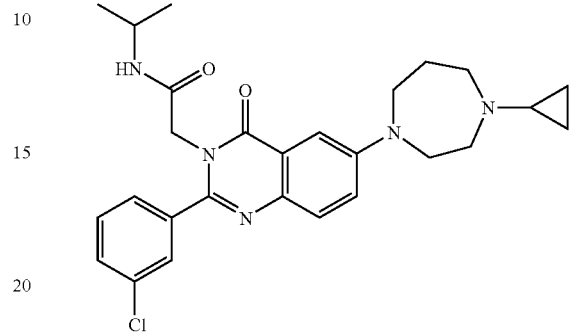

MS (ESI) m/z: 495/497 ([M+H]⁺) (from EXAMPLE 1b).

Example 11a

2-{2-(4-Fluoro-3-methoxyphenyl)-4-oxo-6-[4-(tetrahydropyran-4-ylmethyl)perhydro-1,4-diazepin-1-yl]-4H-quinazolin-3-yl}-N-isopropylacetamide

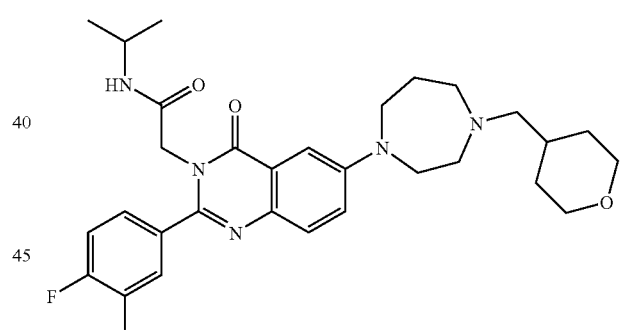

2-(6-(1,4-Diazepan-1-yl)-2-(4-fluoro-3-methoxyphenyl)-4-oxoquinazolin-3(4H)-yl)-N-isopropylacetamide (EXAMPLE 1i) (30 mg, 0.064 mmol), (tetrahydro-2H-pyran-4-yl)methyl 4-methylbenzenesulfonate (35 mg, 0.128 mmol) and DIPEA (17 mg, 21 µl, 0.128 mmol) were dissolved in DMF (1 mL) and stirred at room temperature overnight. Purification by preparative HPLC afforded 2-{2-(4-fluoro-3-methoxyphenyl)-4-oxo-6-[4-(tetrahydropyran-4-ylmethyl)perhydro-1,4-diazepin-1-yl]-4H-quinazolin-3-yl}-N-isopropylacetamide (EXAMPLE 11a) (5 mg, 0.0088 mmol, 14%).

Data for 2-{2-(4-fluoro-3-methoxyphenyl)-4-oxo-6-[4-(tetrahydropyran-4-ylmethyl) perhydro-1,4-diazepin-1-yl]-4H-quinazolin-3-yl}-N-isopropylacetamide (EXAMPLE 11a): MS (ESI) m/z: 566 ([M+H]⁺).

Similarly prepared were:

Example 11b

2-[2-(3-Chlorophenyl)-4-oxo-6-[4-(tetrahydropyran-4-ylmethyl)perhydro-1,4-diazepin-1-yl]-4H-quinazolin-3-yl]-N-isopropylacetamide

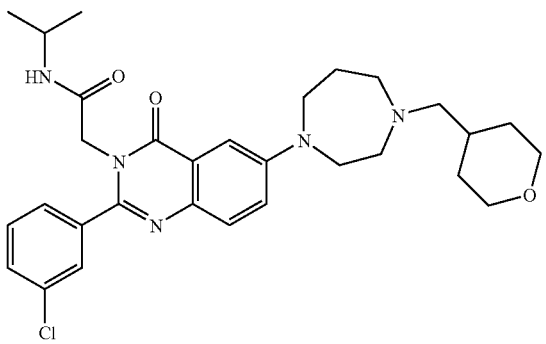

MS (ESI) m/z: 553/555 ([M+H]$^+$) (from EXAMPLE 1b).

Example 11c

2-{2-(3-Chlorophenyl)-6-[4-(1,1-dioxohexahydro-1λ$^6$-thiopyran-4-ylmethyl)Perhydro-1,4-diazepin-1-yl]-4-oxo-4H-quinazolin-3-yl}-N-isopropylacetamide

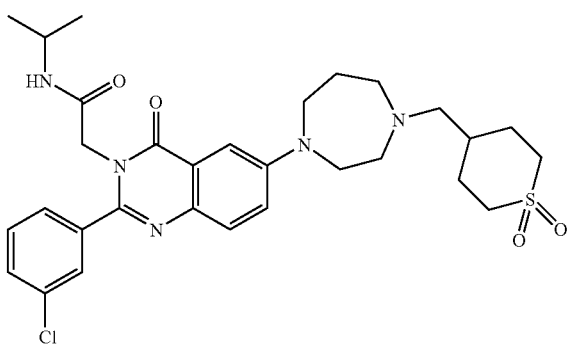

MS (ESI) m/z: 600/602 ([M+H]$^+$) (from EXAMPLE 1b).

Example 11d

2-{2-(3-Chloro-4-fluorophenyl)-6-[4-(1-dioxohexahydro-1λ$^6$-thiopyran-4-ylmethyl)Perhydro-1,4-diazepin-1-yl]-4-oxo-4H-quinazolin-3-yl}-N-isopropylacetamide

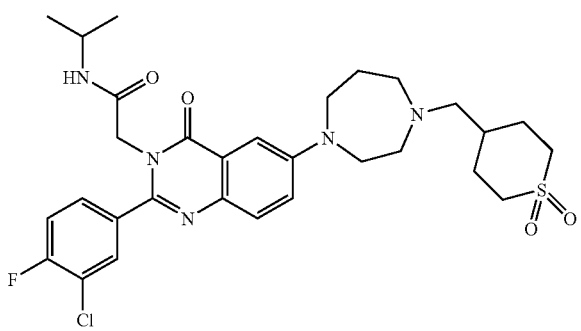

MS (ESI) m/z: 619/621 ([M+H]$^+$) (from EXAMPLE 1e).

Example 11e

2-{2-(4-Fluoro-3-methoxyphenyl)-6-[4-(1,1-dioxohexahydro-1λ$^6$-thiopyran-4-ylmethyl)perhydro-1,4-diazepin-1-yl]-4-oxo-4H-quinazolin-3-yl}-N-isopropylacetamide

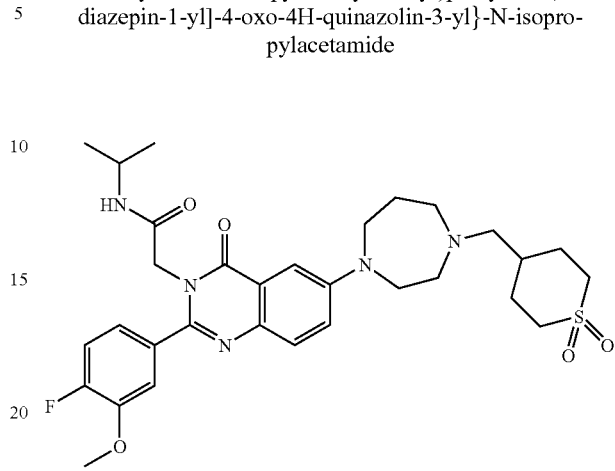

MS (ESI) m/z: 615/617 ([M+H]$^+$) (from EXAMPLE 1i).

Example 12a 4-(2-(3-Chloro-4-fluorophenyl)-3-(2-(isopropylamino)-2-oxoethyl)-4-oxo-3,4-dihydroquinazolin-6-yl)-1-isopropyl-1,4-diazepane 1-oxide

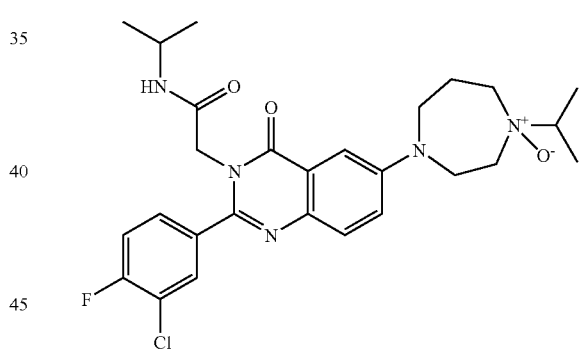

3-Chloroperoxybenzoic acid (19 mg, 0.078 mmol) was added to a stirred solution of 2-[2-(3-chloro-4-fluorophenyl)-6-(4-isopropylperhydro-1,4-diazepin-1-yl)-4-oxo-4H-quinazolin-3-yl]-N-isopropylacetamide (EXAMPLE 6k) (40 mg, 0.078 mmol) in DCM (5 mL). The reaction mixture was stirred for 10 min at room temperature. The reaction mixture was diluted with DCM (10 mL) and washed with aqueous sodium bicarbonate solution (10 mL). The organic phase was dried (Na$_2$SO$_4$), concentrated under reduced pressure and purified by chromatography on silica gel with a gradient of DCM to DCM:MeOH (4:1, v/v) as eluent to afford 4-(2-(3-chloro-4-fluorophenyl)-3-(2-(isopropylamino)-2-oxoethyl)-4-oxo-3,4-dihydroquinazolin-6-yl)-1-isopropyl-1,4-diazepane 1-oxide (EXAMPLE 12a) (25 mg, 0.047 mmol, 61%).

Data for 2-(4-(2-(3-chloro-4-fluorophenyl)-3-(2-(isopropylamino)-2-oxoethyl)-4-oxo-3,4-dihydroquinazolin-6-yl)-1-isopropyl-1,4-diazepane 1-oxide (EXAMPLE 12a): MS (ESI) m/z: 530 (M$^+$).

Example 13a

2-[3-(4-Fluoro-3-methoxyphenyl)-1-oxo-7-perhydro-1,4-diazepin-1-yl-1H-isoquinolin-2-yl]-N-isopropylacetamide

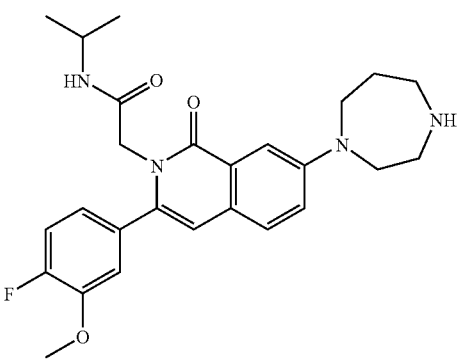

a) 5-Chloro-2,N-dimethylbenzamide

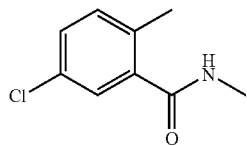

5-Chloro-2-methylbenzoic acid (9.16 g, 53.7 mmol) and thionyl chloride (25.6 g, 15.7 ml, 215 mmol) were heated at reflux temperature for 1.5 h. Solvent was evaporated under reduced pressure and the residue dissolved in DCM (55 mL). Methylamine (aq.) (40%) (12.51 g, 13.90 mL, 161 mmol) was added dropwise at 0° C. The reaction mixture was allowed to warm to room temperature overnight. The reaction mixture was extracted with EtOAc (50 mL), washed with brine (50 mL), dried (Na$_2$SO$_4$) and evaporated in vacuo to afford 5-chloro-2,N-dimethylbenzamide (8.79 g, 47.9 mmol, 89%) as a white solid. This was used directly in the next stage without purification Data for 5-chloro-2,N-dimethylbenzamide: MS (ESI) m/z: 184 ([M+H]$^+$).

b) 7-Chloro-3-(4-fluoro-3-methoxyphenyl)-2H-isoquinolin-1-one

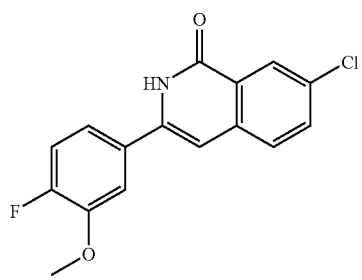

A solution of 5-chloro-2,N-dimethylbenzamide (5.0 g, 27.2 mmol) in THF (28 mL) was cooled to −78° C. and a solution of 2M lithium diisopropylamide in THF (40.8 mL, 82 mmol) diluted with THF (68 mL) added. 4-Fluoro-3-methoxybenzonitrile (4.12 g, 27.2 mmol) in THF (28 mL) was added and the mixture stirred at −78° C. for 2.5 h. Sat. NH$_4$Cl (aq.) was added and the mixture extracted with EtOAc (2×50 mL). A precipitate formed in the aqueous which was collected by filtration to afford 7-chloro-3-(4-fluoro-3-methoxyphenyl)-2H-isoquinolin-1-one (3.74 g, 12.3 mmol, 45%).

c) [7-Chloro-3-(4-fluoro-3-methoxyphenyl)-1-oxo-1H-isoquinolin-2-yl]acetic acid methyl ester

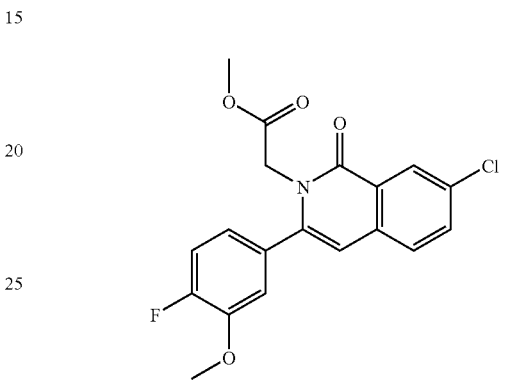

7-Chloro-3-(4-fluoro-3-methoxyphenyl)-2H-isoquinolin-1-one (500 mg, 1.646 mmol) and potassium carbonate (455 mg, 3.29 mmol) were combined and DMF (5 mL) added to give a white suspension. The reaction mixture was stirred for 30 min at room temperature. Methyl bromoacetate (756 mg, 0.456 mL, 4.94 mmol) was added and stirring continued for a further 2 h. The reaction mixture was diluted with EtOAc (50 mL) and washed with water (2×10 mL), brine (10 mL) and the organic layer dried (MgSO$_4$) and concentrated under reduced pressure. This afforded [7-chloro-3-(4-fluoro-3-methoxyphenyl)-1-oxo-1H-isoquinolin-2-yl]acetic acid methyl ester still containing DMF (~2 mL). This solution was taken onto the next step without further purification.

Data for [7-chloro-3-(4-fluoro-3-methoxyphenyl)-1-oxo-1H-isoquinolin-2-yl]acetic acid methyl ester: MS (ESI) m/z: 376/378 ([M+H]$^+$).

d) 2-[7-Chloro-3-(4-fluoro-3-methoxyphenyl)-1-oxo-1H-isoquinolin-2-yl]-N-isopropylacetamide

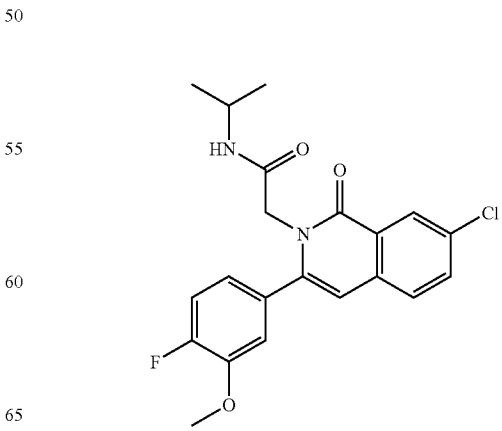

[7-Chloro-3-(4-fluoro-3-methoxyphenyl)-1-oxo-1H-isoquinolin-2-yl]acetic acid methyl ester (crude product from the previous experiment) was dissolved in NMP (4 mL). Propan-2-amine (973 mg, 1.402 mL, 16.46 mmol) was added dropwise with stirring and an exotherm was observed. LCMS analysis indicated that the reaction had gone to about 75% completion. Further propan-2-amine (348 mg, 0.5 mL, 5.88 mmol) was added and the reaction mixture heated at reflux temperature for 5 min followed by stirring at room temperature overnight. The resultant precipitate was filtered and washed with diethyl ether (150 mL). This afforded product contaminated with isopropylamine. The solid was dissolved in DCM (50 mL) and washed with water (2×10 mL). The organics were dried (MgSO4) and concentrated to afford 2-[7-chloro-3-(4-fluoro-3-methoxyphenyl)-1-oxo-1H-isoquinolin-2-yl]-N-isopropylacetamide (300 mg, 0.745 mmol).

Data for 2-[7-chloro-3-(4-fluoro-3-methoxyphenyl)-1-oxo-1H-isoquinolin-2-yl]-N-isopropylacetamide: MS (ESI) m/z: 404/406 ([M+H]$^+$).

e) 2-[3-(4-Fluoro-3-methoxyphenyl)-1-oxo-7-Perhydro-1,4-diazepin-1-yl-1H-isoquinolin-2-yl]-N-isopropylacetamide

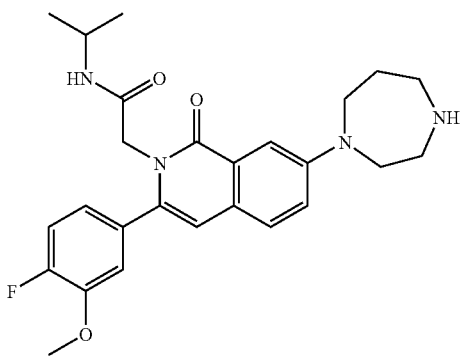

Tert-butyl 1-homopiperazinecarboxylate (66 mg, 0.07 mL, 0.330 mmol) was added to potassium tert-butoxide (67 mg, 0.601 mmol), [1,3-bis(2,6-diisopropylphenyl)imidazol-2-ylidene](3-chloropyridyl)palladium(II) dichloride (PEPPSI-IPr catalyst) (20 mg, 0.030 mmol) and 2-[7-chloro-3-(4-fluoro-3-methoxyphenyl)-1-oxo-1H-isoquinolin-2-yl]-N-isopropylacetamide (121 mg, 0.300 mmol) in toluene (3 mL). The reaction mixture was heated at 100° C. for 2 h, after which time the reaction mixture was cooled and quenched by addition of sat. NH$_4$Cl (aq.) (0.2 mL). Stirring was continued for 1 h at room temperature. MeOH (3 mL) was added and stirring continued for a further 30 min.

This solution was added to a pre-acidified SCX cartridge and eluted with MeOH, followed by 2M NH$_3$/MeOH. TLC analysis indicated that the desired product was present in the basic fractions, as well as de-boc'ed material. Solvent was evaporated under reduced pressure. The resultant greenish gum was dissolved in DCM (10 mL), cooled to 0° C. and trifluoroacetic acid (0.2 mL) added.

The reaction mixture was stirred at 0° C. for 3 h. Solvent was evaporated under reduced pressure and crude product purified on SCX eluting product with 2M NH$_3$/MeOH. Crude product was further purified by preparative LCMS (basic conditions) to afford 2-[3-(4-fluoro-3-methoxyphenyl)-1-oxo-7-perhydro-1,4-diazepin-1-yl-1H-isoquinolin-2-yl]-N-isopropylacetamide (2 mg, 0.004 mmol, 13%).

Data for 2-[3-(4-fluoro-3-methoxyphenyl)-1-oxo-7-perhydro-1,4-diazepin-1-yl-1H-isoquinolin-2-yl]-N-isopropylacetamide: MS (ESI) m/z: 467 ([M+H]$^+$).

Example 14

Chinese Hamster Ovary (CHO) cells stably expressing the human V$_3$ receptor were incubated to equilibrium with the test compound (at a final assay concentration of $10^{-10}$ mol.L$^{-1}$ to $10^{-5}$ mol.L$^{-1}$) and [$^3$H]AVP (at a final assay concentration of $2.5 \times 10^{-9}$ mol.L$^{-1}$). Throughout the concentration of dimethylsulphoxide (DMSO) did not exceed 0.1% (v/v). After washing with ice-cold phosphate buffered saline (PBS), scintillation fluid was added and the plates counted on a Topcount NXT apparatus.

A sigmoidal dose response curve (non-linear regression, variable slope) was plotted as concentration of test compound (mol.L$^{-1}$) against percentage specific binding of [$^3$H]AVP and a K$_i$ value was calculated. Each determination was carried out in triplicate and repeated on at least 3 separate occasions Table 1 shows the binding activity obtained for some representative compounds of the invention.

TABLE 1

V$_3$ binding activity for compounds according to the invention

| | | |
|---|---|---|
| EXAMPLE 1b: 2-[2-(3-Chlorophenyl)-4-oxo-6-perhydro-1,4-diazepin-1-yl-4H-quinazolin-3-yl]-N-isopropylacetamide | 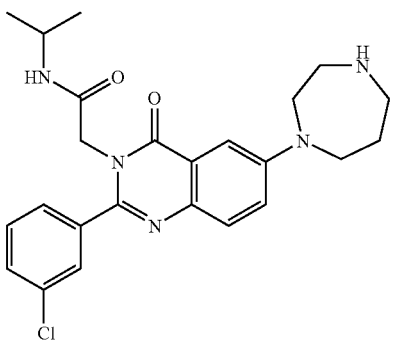 | +++ |

TABLE 1-continued

V₃ binding activity for compounds according to the invention

EXAMPLE 2b: N-Isopropyl-2-[2-(3-methoxyphenyl)-4-oxo-6-piperazin-1-yl-4H-quinazolin-3-yl]acetamide

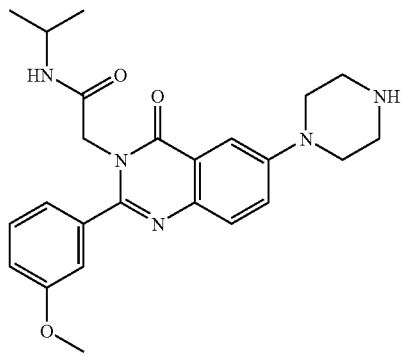

++

EXAMPLE 3c: 2-[6-(3-Dimethylaminomethylpiperidin-1-yl)-2-(3-methoxyphenyl)-4-oxo-4H-quinazolin-3-yl]-N-isopropylacetamide

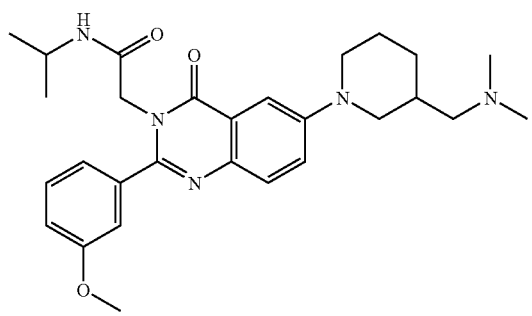

++

EXAMPLE 3f: N-Isopropyl-2-[2-(3-methoxyphenyl)-4-oxo-6-((R)-3-piperidin-1-ylmethylpiperidin-1-yl)-4H-quinazolin-3-yl]acetamide

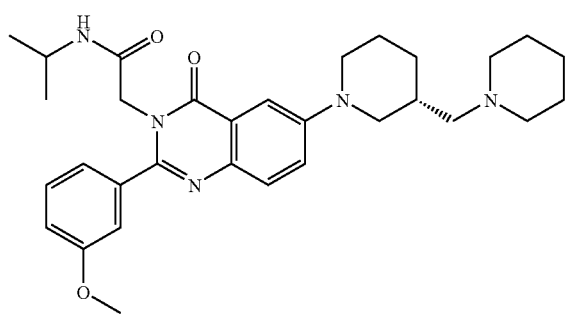

+++

EXAMPLE 4c: N-Isopropyl-2-{2-(3-methoxyphenyl)-4-oxo-6-[4-(2,2,2-trifluoroethyl)perhydro-1,4-diazepin-1-yl]-4H-quinazolin-3-yl}acetamide

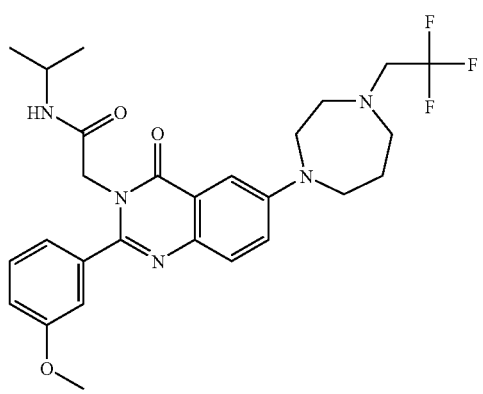

+

TABLE 1-continued

V₃ binding activity for compounds according to the invention

EXAMPLE 4d: N-Isopropyl-2-[6-[4-(2-methoxyethyl)perhydro-1,4-diazepin-1-yl]-2-(3-methoxyphenyl)-4-oxo-4H-quinazolin-3-yl]acetamide

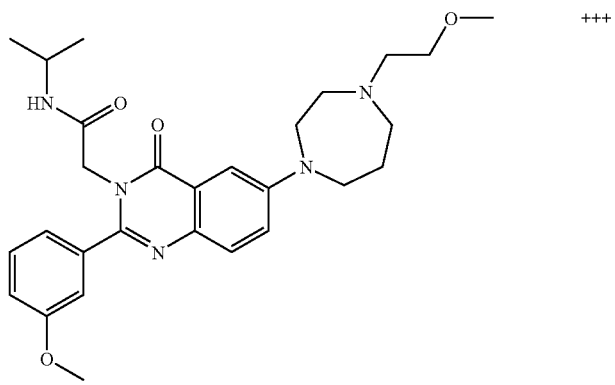

+++

EXAMPLE 5s: 2-[2-(3-Chloro-4-fluorophenyl)-4-oxo-6-(4,6,6-trimethylperhydro-1,4-diazepin-1-yl)-4H-quinazolin-3-yl]-N-isopropylacetamide

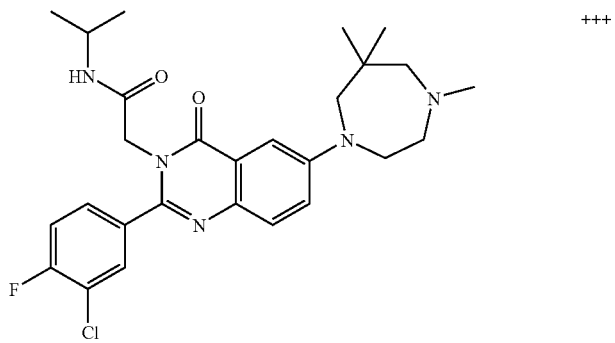

+++

EXAMPLE 5Ac: 2-{2-(3-Chloro-4-fluorophenyl)-6-[4-(2,2-dimethylpropyl)perhydro-1,4-diazepin-1-yl]-4-oxo-4H-quinazolin-3-yl}-N-isopropylacetamide

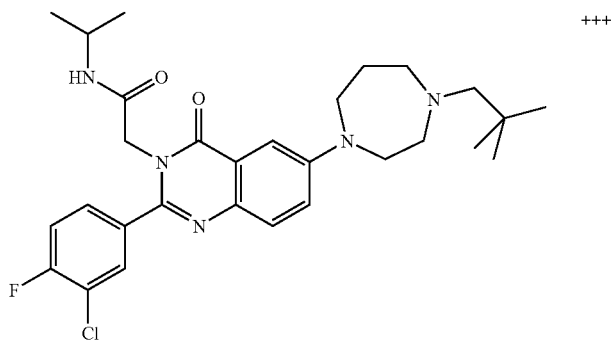

+++

EXAMPLE 6w: 2-[2-(3-Chloro-5-trifluoromethoxyphenyl)-6-(4-isopropylperhydro-1,4-diazepin-1-yl)-4-oxo-4H-quinazolin-3-yl]-N-isopropylacetamide

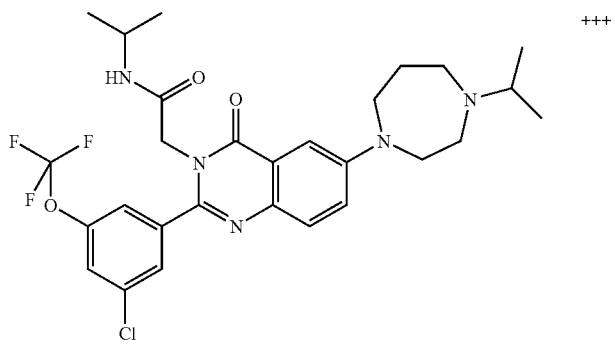

+++

TABLE 1-continued

V₃ binding activity for compounds according to the invention

| | | |
|---|---|---|
| EXAMPLE 7a: N-tert-Butyl-2-(2-cyclopentyl-4-oxo-6-perhydro-1,4-diazepin-1-yl-4H-quinazolin-3-yl-acetamide | 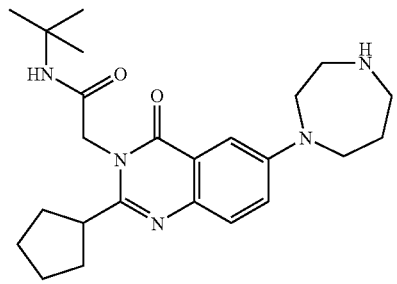 | ++ |
| EXAMPLE 9h: 2-[6-(4-Ethylperhydro-1,4-diazepin-1-yl)-2-(4-fluoro-3-methoxyphenyl)-4-oxo-4H-quinazolin-3-yl]-N-(2,2,2-trifluoro-1,1-dimethylethyl)acetamide | 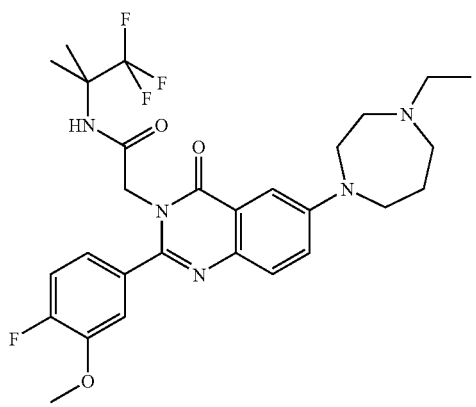 | +++ |
| EXAMPLE 9u: 2-[2-(3-Chlorophenyl)-6-(4-isopropylperhydro-1,4-diazepin-1-yl)-4-oxo-4H-quinazolin-3-yl]-N-isopropyl-N-methylacetamide | 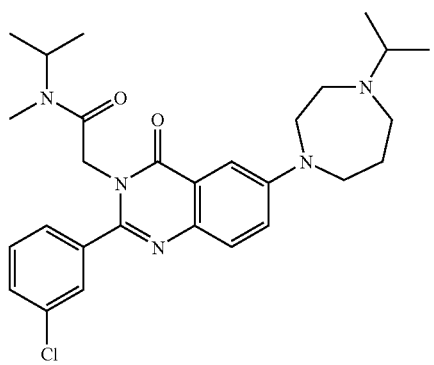 | ++ |
| EXAMPLE 9Ah: 2-[6-(1,4-Diazabicyclo[3.2.2]non-4-yl)-2-(4-fluoro-3-methoxyphenyl)-4-oxo-4H-quinazolin-3-yl]-N-(2-methoxy-1-methylethyl) acetamide | 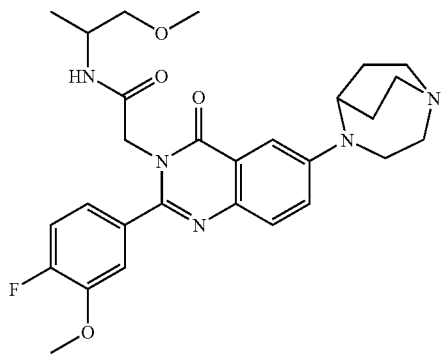 | ++ |

+++ 0-10 nM
++ 10-100 nM
+ 100 nM-1 uM

The ability of compounds of the invention to act as $V_3$ antagonists in a physiologically relevant system was determined by measuring their ability to block the release of adrenocorticotropic hormone (ACTH) from anterior pituitary corticotrophs in response to treatment with arginine vasopressin (AVP).

Anterior pituitary corticotrophs were prepared from adult female Sprague-Dawley rats and seeded into 48 well plates. The cells were cultured for 4 days prior to exposure to compound. Test compounds were prepared at $10^{-5}$ mol.L$^{-1}$ in 100% DMSO. Cells were exposed to a dose response of test compounds for 20 minutes ($10^{-8}$ mol.L$^{-1}$-$10^{-5}$ mol.L$^{-1}$). The final concentration of DMSO in the assay was kept constant at 0.3%. The cells were then exposed to $3 \times 10^{-9}$ mol.L$^{-1}$ AVP for 120 minutes. Supernatants were harvested and stored at $-20°$ C. ACTH levels were subsequently measured by ELISA following the manufacturer's instructions (Immunodiagnostic systems, UK (Cat No. DX-SDX018)). Each treatment was carried out in quadruplicate and a mean value obtained for the amount of ACTH released. The degree of antagonism was then calculated as a percentage of the amount of ACTH released by agonist alone after adjustment for basal levels of ACTH. A pIC$_{50}$ was calculated by fitting a Sigmoidal dose response (variable slope) curve with a non-linear (fit) to the data using the software package GraphPad prism. Each determination was repeated on at least 3 separate occasions Table 2 shows the activity obtained for some representative compounds of the invention.

TABLE 2

$V_3$ receptor antagonism in isolated rat anterior pituitary cells for compounds according to the invention

| | | |
|---|---|---|
| EXAMPLE 4b: N-Isopropyl-2-[6-(4-isopropylperhydro-1,4-diazepin-1-yl)-2-(3-methoxyphenyl)-4-oxo-4H-quinazolin-3-yl]acetamide | 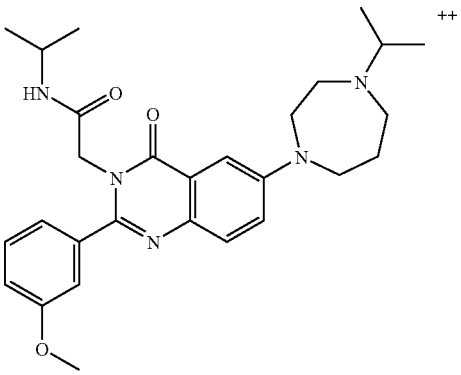 | ++ |

++ 10-100 nM
+ 100 nM-1 uM

What is claimed:

1. A compound of formula I,

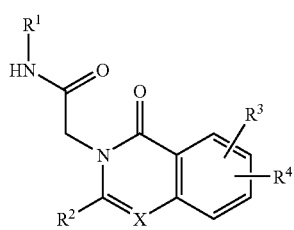

formula I

formula II wherein

R$^1$ is C$_{1-6}$alkyl, C$_{3-6}$cycloalkyl, C$_{3-6}$cycloalkylC$_{1-3}$alkyl, C$_{2-6}$alkenyl, C$_{2-6}$alkynyl, said C$_{1-6}$alkyl, C$_{3-6}$cycloalkyl and C$_{3-6}$cycloalkylC$_{1-3}$alkyl being optionally substituted with hydroxy, C$_{1-6}$ alkyloxy, cyano or one or more halogens;

R$^2$ is C$_{6-10}$aryl optionally substituted with one to three substituents selected from halogen, hydroxy, cyano, C$_{1-6}$alkyl, C$_{3-6}$cycloalkyl, C$_{1-6}$alkyloxy and C$_{3-6}$cycloalkyloxy, said C$_{1-6}$alkyl, C$_{3-6}$ cycloalkyl, alkyloxy and C$_{3-6}$cycloalkyloxy being optionally substituted with one or more halogens;

or R$^2$ is a 5-10 membered heteroaryl ring system comprising a heteroatom selected from N, O and S and optionally substituted with a substituent selected from methyl, C$_{1-6}$alkyloxy and halogen;

or R$^2$ is C$_{4-7}$cycloalkyl;

R$^3$ is an optional substituent selected from C$_{1-6}$alkyl, C$_{1-6}$alkyloxy and halogen, said C$_{1-6}$alkyl and C$_{1-6}$alkyloxy being optionally substituted with one or more halogens;

R$^4$ is a group located at the 6- or 7-position of the quinazolinone or isoquinolinone ring having the formula II wherein R$^5$ is joined together with one of R$^7$ and R$^8$ to have the structure of formula II form a 1,4-diazepine ring optionally substituted with one or two substituents selected from methyl, halogen, hydroxy and oxo;

Each $R^6$ is independently H, halogen or $C_{1-4}$alkyl optionally substituted with halogen or $SO_2CH_3$;

$R^7$ and $R^8$ are independently H, $C_{1-6}$alkyl, $C_{3-6}$cycloalkyl, $C_{3-6}$cycloalkyl$C_{1-3}$alkyl, cyano$C_{1-3}$alkyl, $C_{6-10}$aryl, $C_{6-10}$aryl$C_{1-3}$alkyl, $C_{1-3}$alkyloxy$C_{1-3}$alkyl or $C_{1-6}$acyl said $C_{1-6}$alkyl, $C_{3-6}$cycloalkyl and $C_{3-6}$cycloalkyl$C_{1-3}$alkyl being optionally substituted with hydroxy, 1 or more halogens or di$C_{1-2}$alkylamino;

Each $R^{12}$ is independently H or $C_{1-4}$alkyl;

m is 2 or 3; and

X is N or CH, or a pharmaceutically acceptable salt thereof.

2. The compound according to claim 1, wherein $R^1$ is isopropyl, isobutyl, tertiary-butyl, cyclopropylmethyl, cyclobutyl, 2,2,2-trifluoro-1-methylethyl or 2,2,2-trifluoro-1,1-dimethylethyl.

3. The compound according to claim 1, wherein $R^2$ is a substituted phenyl ring selected from 3-chlorophenyl, 3-fluorophenyl, 3-methoxyphenyl, 3-trifluoromethoxyphenyl, 3-chloro-4-fluorophenyl, 4-fluoro-3-methoxyphenyl and 3,5-dimethoxyphenyl.

4. The compound according to claim 1, wherein $R^4$ is a group selected from

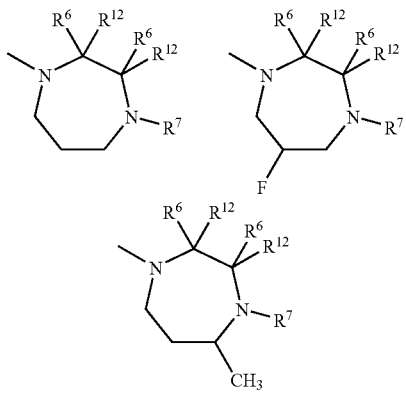

wherein $R^6$, $R^7$ and $R^{12}$ have the previously defined meanings.

5. The compound according to claim 1, wherein X is N and $R^4$ is a substituent at the 6-position.

6. The compound according to claim 1, wherein X is N.

7. A compound selected from:

2-[2-(3-Chlorophenyl)-4-oxo-6-perhydro-1,4-diazepin-1-yl-4H-quinazolin-3-yl]-N-isopropylacetamide;

N-tert-Butyl-2-[2-(3-chlorophenyl)-4-oxo-6-perhydro-1,4-diazepin-1-yl-4H-quinazolin-3-yl]acetamide;

N-tert-Butyl-2-(2-(3-chloro-4-fluorophenyl)-6-(1,4-diazepan-1-yl)-4-oxoquinazolin-3(4H)-yl)acetamide;

2-(2-(3-Chloro-4-fluorophenyl)-6-(1,4-diazepan-1-yl)-4-oxoquinazolin-3(4H)-yl)-N-isopropylacetamide;

2-(2-(3-Chloro-4-fluorophenyl)-6-(3-methyl-1,4-diazepan-1-yl)-4-oxoquinazolin-3(4H)-yl)-N-isopropylacetamide;

2-[2-(3-Chloro-4-fluorophenyl)-6-(3-ethylperhydro-1,4-diazepin-1-yl)-4-oxo-4H-quinazolin-3-yl]-N-isopropylacetamide;

2-[2-(3-Chloro-4-fluorophenyl)-6-(dimethylperhydro-1,4-diazepin-1-yl)-4-oxo-4H-quinazolin-3-yl]-N-isopropylacetamide;

2-[6-(Dimethylperhydro-1,4-diazepin-1-yl)-2-(4-fluoro-3-methoxyphenyl)-4-oxo-4H-quinazolin-3-yl]-N-isopropylacetamide;

2-[2-(3-Chloro-4-fluorophenyl)-6-((S)-3-isopropylperhydro-1,4-diazepin-1-yl)-4-oxo-4H-quinazolin-3-yl]-N-isopropylacetamide;

2-[2-(3-Chlorophenyl)-6-((S)-3-isopropylperhydro-1,4-diazepin-1-yl)-4-oxo-4H-quinazolin-3-yl]-N-isopropylacetamide;

2-[2-(4-Fluoro-3-methoxyphenyl)-6-((S)-3-isopropylperhydro-1,4-diazepin-1-yl)-4-oxo-4H-quinazolin-3-yl]-N-isopropylacetamide;

2-[2-(3-Chloro-4-fluorophenyl)-6-((R)-3-isopropylperhydro-1,4-diazepin-1-yl)-4-oxo-4H-quinazolin-3-yl]-N-isopropylacetamide;

2-[2-(3-Chlorophenyl)-6-((R)-3-isopropylperhydro-1,4-diazepin-1-yl)-4-oxo-4H-quinazolin-3-yl]-N-isopropylacetamide;

2-[2-(4-Fluoro-3-methoxyphenyl)-6-((R)-3-isopropylperhydro-1,4-diazepin-1-yl)-4-oxo-4H-quinazolin-3-yl]-N-isopropylacetamide;

2-[2-(3-Chlorophenyl)-6-(4-methylperhydro-1,4-diazepin-1-yl)-4-oxo-4H-quinazolin-3-yl]-N-isopropylacetamide;

2-[6-(4-Ethylperhydro-1,4-diazepin-1-yl)-2-(3-methoxyphenyl)-4-oxo-4H-quinazolin-3-yl]-N-isopropylacetamide;

2-[2-(3-Chlorophenyl)-4-oxo-6-(4-propylperhydro-1,4-diazepin-1-yl)-4H-quinazolin-3-yl]-N-isopropylacetamide;

N-tert-Butyl-2-[6-(4-ethylperhydro-1,4-diazepin-1-yl)-2-(4-fluoro-3-methoxyphenyl)-4-oxo-4H-quinazolin-3-yl]acetamide;

2-[2-(3-Chlorophenyl)-6-(4-ethylperhydro-1,4-diazepin-1-yl)-4-oxo-4H-quinazolin-3-yl]-N-isopropylacetamide;

2-[6-(4-Ethylperhydro-1,4-diazepin-1-yl)-2-(4-fluoro-3-methoxyphenyl)-4-oxo-4H-quinazolin-3-yl]-N-isopropylacetamide;

2-[2-(4-Fluoro-3-methoxyphenyl)-4-oxo-6-(4-propylperhydro-1,4-diazepin-1-yl)-4H-quinazolin-3-yl]-N-isopropylacetamide;

2-[2-(3-Chloro-4-fluorophenyl)-6-(4-ethylperhydro-1,4-diazepin-1-yl)-4-oxo-4H-quinazolin-3-yl]-N-isopropylacetamide;

N-Isopropyl-2-[6-(4-isopropylperhydro-1,4-diazepin-1-yl)-2-(3-methoxyphenyl)-4-oxo-4H-quinazolin-3-yl]acetamide;

2-[2-(3-Chloro-4-fluorophenyl)-6-(4-isopropylperhydro-1,4-diazepin-1-yl)-4-oxo-4H-quinazolin-3-yl]-N-isopropylacetamide;

2-[2-(3-Chloro-5-trifluoromethylphenyl)-4-oxo-6-perhydro-1,4-diazepin-1-yl-4H-quinazolin-3-yl]-N-isopropylacetamide;

2-[2-(3,5-Dimethoxyphenyl)-6-(4-isopropylperhydro-1,4-diazepin-1-yl)-4-oxo-4H-quinazolin-3-yl]-N-isopropylacetamide;

2-[2-(3-Chloro-4-fluorophenyl)-6-{4-(1-cyclopropylethyl)perhydro-1,4-diazepin-1-yl]-4-oxo-4H-quinazolin-3-yl}-N-isopropylacetamide;

2-{2-(4-Fluoro-3-methoxyphenyl)-6-[4-(2-hydroxyethyl)perhydro-1,4-diazepin-1-yl]-4-oxo-4H-quinazolin-3-yl}-N-isopropylacetamide;

2-{2-(3-Chloro-4-fluorophenyl)-6-[4-(2-hydroxyethyl)perhydro-1,4-diazepin-1-yl]-4-oxo-4H-quinazolin-3-yl}-N-isopropylacetamide;

2-[2-(3-Chlorophenyl)-6-(4-isopropylperhydro-1,4-diazepin-1-yl)-4-oxo-4H-quinazolin-3-yl]-N-(2,2,2-trifluoro-1,1-dimethylethyl)acetamide;

N-Isopropyl-2-(6-(4-isopropyl-1,4-diazepan-1-yl)-2-(3-methoxyphenyl)-4-oxoquinazolin-3(4H)-yl)acetamide;

2-(2-(3-Chlorophenyl)-6-(4-cyclopropylmethyl-1,4-diazepan-1-yl)-4-oxoquinazolin-3(4H)-yl)-N-isopropylacetamide and N-tert-Butyl-2-(2-(3-chlorophenyl)-6-(4-isopropyl-1,4-diazepan-1-yl)-4-oxoquinazolin-3(4H)-yl)acetamide or a pharmaceutically acceptable salt thereof.

8. A pharmaceutical composition comprising a compound according to claim 1, or a pharmaceutically acceptable salt thereof, in admixture with and one or more pharmaceutically acceptable auxiliaries.

9. A pharmaceutical composition comprising a compound according to claim 7, or a pharmaceutically acceptable salt thereof, and one or more pharmaceutically acceptable auxiliaries.

10. 2-(2-(3-Chlorophenyl)-6-(4-cyclopropylmethyl-1,4-diazepan-1-yl)-4-oxoquinazolin-3(4H)-yl)-N-isopropylacetamide.

11. A pharmaceutical composition comprising a compound according to claim 10, or a pharmaceutically acceptable salt thereof, and one or more pharmaceutically acceptable auxiliaries.

\* \* \* \* \*